US012053387B2

(12) United States Patent
Nguyen et al.

(10) Patent No.: US 12,053,387 B2
(45) Date of Patent: Aug. 6, 2024

(54) KNEE PROSTHESIS

(71) Applicant: Optimotion Implants LLC, Orlando, FL (US)

(72) Inventors: Vuong Binh Nguyen, Windermere, FL (US); Andrew Rynearson, Winter Springs, FL (US); Daniel F. Justin, Orlando, FL (US); Dinesh V. Koka, Winter Springs, FL (US)

(73) Assignee: OPTIMOTION IMPLANTS LLC, Orlando, FL (US)

( * ) Notice: Subject to any disclaimer, the term of this patent is extended or adjusted under 35 U.S.C. 154(b) by 574 days.

(21) Appl. No.: 17/322,273

(22) Filed: May 17, 2021

(65) Prior Publication Data
US 2022/0362029 A1    Nov. 17, 2022

(51) Int. Cl.
*A61F 2/38* (2006.01)
(52) U.S. Cl.
CPC .......... *A61F 2/3886* (2013.01); *A61F 2/3859* (2013.01); *A61F 2/389* (2013.01); *A61F 2002/3863* (2013.01)
(58) Field of Classification Search
CPC ............................................. A61F 2002/30621
See application file for complete search history.

(56) References Cited

U.S. PATENT DOCUMENTS

| 2005/0197710 | A1* | 9/2005 | Naegerl | A61F 2/389 623/20.32 |
|---|---|---|---|---|
| 2008/0009950 | A1 | 1/2008 | Richardson | |
| 2009/0062924 | A1 | 3/2009 | Kito | |
| 2013/0131819 | A1* | 5/2013 | Parisi | A61F 2/389 623/20.33 |
| 2013/0190884 | A1* | 7/2013 | Hashida | A61F 2/3836 623/20.29 |
| 2017/0020674 | A1* | 1/2017 | Walker | A61F 2/38 |
| 2018/0085225 | A1 | 3/2018 | Wentorf | |
| 2020/0268519 | A1* | 8/2020 | White | A61F 2/389 |

OTHER PUBLICATIONS

Haider, H. 7.10 Wear: Knee Joint Arthroplasty. In: Ducheyne, P., Grainger, D.W., Healy, K.E., Hutmacher, D.W., and Kirkpatrick, C.J. (eds.), Comprehensive Biomaterials II, vol. 7, pp. 152-174. (2017) Oxford: Elsevier.

* cited by examiner

*Primary Examiner* — Javier G Blanco
(74) *Attorney, Agent, or Firm* — David Meibos; Maywood IP Law

(57) ABSTRACT

A knee joint prosthesis may be for implantation in a knee of a patient. The knee prosthesis may comprise a tibial component configured to be implanted on the tibia and a femoral component configured to be implanted on the femur. The femoral component may comprise a medial condyle with a medial articulation surface and a lateral condyle with a lateral articulation surface. The medial articulation surface and the lateral articulation surface may be shaped substantially symmetrically to each other across a femoral component plane bisecting the femoral component. The tibial component may comprise an articulation surface with a medial articulation side configured to articulate with the medial articulation surface and a lateral articulation side configured to articulate with the lateral articulation surface. The medial articulation side and the lateral articulation side may be shaped substantially asymmetrically to each other across a tibial component plane bisecting the tibial component.

3 Claims, 50 Drawing Sheets

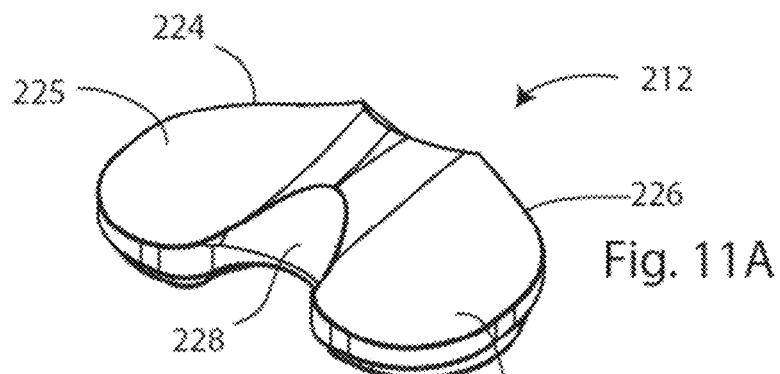
Fig. 11A
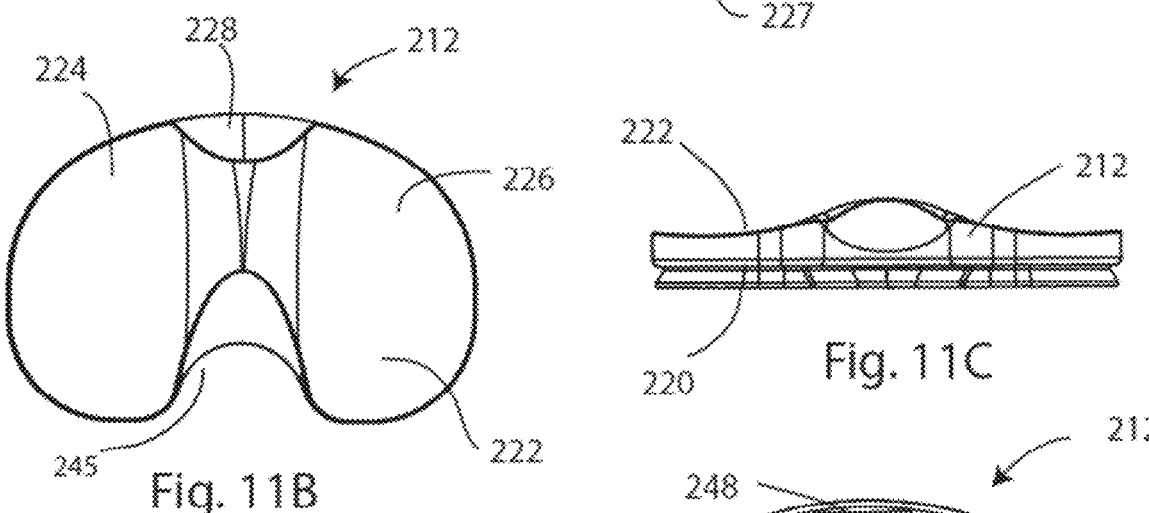
Fig. 11B
Fig. 11C
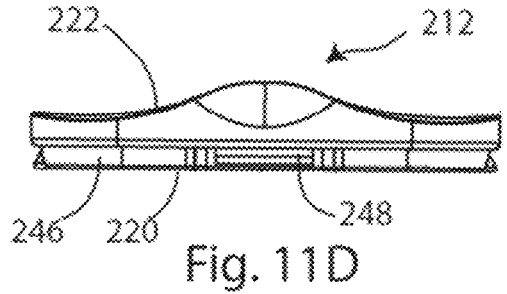
Fig. 11D
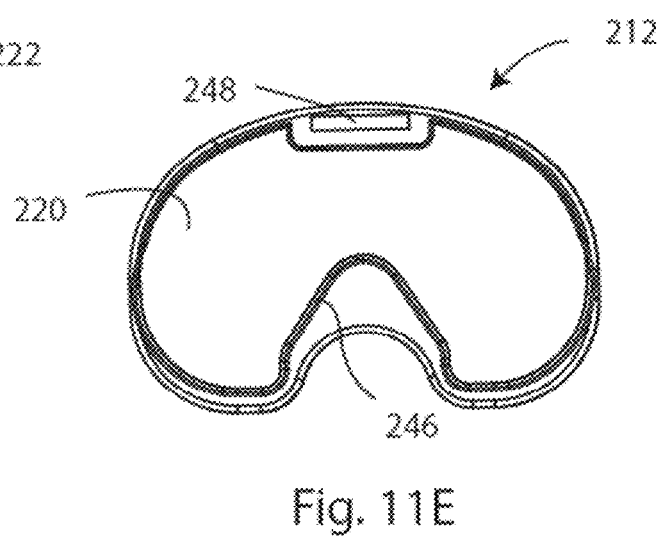
Fig. 11E

|  | Cruciate Retaining Insert | Posterior Stabilizing Insert | Constrained Condylar Knee Insert |
|---|---|---|---|
| Cruciate Retaining Femoral Component | X | X | X |
| Posterior Stabilizing Femoral Component | X | X | X |

Fig. 13

KNEE PROSTHESIS

TECHNICAL FIELD

The present disclosure relates to surgical devices, systems, instruments, and methods. More specifically, the present disclosure relates to orthopedic knee replacement surgical devices, instruments, systems, and methods.

BACKGROUND

A number of knee replacement options exist which may be implemented depending upon the level of compromise of the natural knee anatomy. The knee anatomy complex includes the knee joint between the femur distal end and the tibia proximal end, and the surrounding anterior and posterior cruciate ligaments (ACL, PCL), and medial and lateral collateral ligaments (MCL, LCL), which provide support and stabilization to the knee joint. When one or more ligaments are compromised, for example through injury, disease, or aging, a knee prosthesis system may be implanted to replace the knee joint.

A typical knee prosthesis system includes a tibial bone anchoring component, a tibial articulating component, which may be called a tibial insert, and a femoral bone anchoring component. Prior art knee prostheses do not provide sufficient stability to the knee as it translates from extension to flexion. Existing tibial and femoral components do not adequately allows for the knee to mimic the natural biomechanical movement of the tibia in relation to the femur. Prior art prostheses preclude outward rotation of the tibia and lower leg, which occurs naturally in knee flexion. In the absence of the rotation, tension in the ligaments surrounding the knee is not maintained, and the knee is not properly stabilized.

SUMMARY

The various systems and methods of the present disclosure have been developed in response to the present state of the art, and in particular, in response to the problems and needs in the art that have not yet been fully solved by currently available technology.

In an embodiment a knee joint prosthesis may be for implantation in a knee of a patient, wherein the knee joint defines a junction of a femur of the patient and a tibia of the patient. The knee prosthesis may comprise a tibial component configured to be implanted on the tibia and a femoral component configured to be implanted on the femur. The femoral component may comprise a medial condyle with a medial articulation surface and a lateral condyle with a lateral articulation surface. The medial articulation surface and the lateral articulation surface may be shaped substantially symmetrically to each other across a femoral component plane bisecting the femoral component. The tibial component may comprise an articulation surface with a medial articulation side configured to articulate with the medial articulation surface and a lateral articulation side configured to articulate with the lateral articulation surface. The medial articulation side and the lateral articulation side may be shaped substantially asymmetrically to each other across a tibial component plane bisecting the tibial component.

The medial articulation side may comprise a medial side height differential defined by a posterior edge with a first height, and an anterior side with a second height. The lateral articulation side may comprise a lateral side height differential defined by a posterior side with a third height, and an anterior side with a fourth height. The medial side height differential may be greater than the lateral side height differential.

The medial articulation side may comprise an anterior section with a maximum anterior height and a posterior section with a maximum posterior height. The posterior section may further comprise a posterior ramp. The posterior ramp may have a first height proximate a lateral edge of the posterior section and a second height anterior and/or medial to the lateral edge and wherein the first height may be greater than the second height.

The lateral articulation surface may comprise an anterior section with a maximum anterior height and a posterior section with a maximum posterior height. The maximum posterior height of the medial articulation side may be greater than the maximum posterior height of the lateral articular side.

The femoral component and the tibial component may be shaped such that, after implantation in the knee, the femoral component and the tibial component engage at a medial dwell point and a lateral dwell point. The medial dwell point may migrate medially and/or the lateral dwell point migrates laterally during flexion of the knee.

In an embodiment, the knee joint prosthesis may comprise a tibial component having a base configured to be implanted on a tibia of a patient and a femoral component configured to be implanted on the femur. The femoral component may comprise a medial condyle with a medial articulation surface and a lateral condyle with a lateral articulation surface.

The tibial component may comprise an articulation surface with a medial articulation side, which may comprise a medial perimeter, a medial high point, and a medial low point. The medial high point and medial low point are defined by a medial differential. A lateral articulation side may comprise a lateral perimeter, a lateral high point, and a lateral low point, wherein the lateral high point and the lateral low point are defined by a lateral differential. The medial differential may be greater than the lateral differential.

The medial high point may be on a medial ramp, proximate a posterior section of the medial perimeter. The ramp may extend anteriorly from the medial high point toward the medial low point of the medial articulation side.

The medial articulation side may have a medial thickness, relative to the base of the tibial component. The lateral articulation side may have a lateral thickness, relative to the base of the tibial component. The medial thickness at a lateral, posterior section of the medial perimeter may be greater than the lateral thickness at a medial, posterior section of the lateral perimeter.

The medial articulation side may further comprise a medial edge differential defined by a posterior side with a first height, and an anterior side with a second height. The lateral articulation side may further comprise a lateral side differential defined by a posterior side with a third height, and an anterior side with a fourth height. The medial edge differential may be greater than the lateral edge differential.

The femoral component and the tibial component may be shaped such that, after implantation in the knee, the femoral component and the tibial component engage at a medial dwell point and a lateral dwell point. The medial dwell point may migrate medially and/or the lateral dwell point migrates laterally during flexion of the knee.

The femoral component and the tibial component may be further shaped such that, during flexion, the tibial component pivots medially relative to the femoral component.

The femoral component and the tibial component may be further shaped such that, during flexion, tension is maintained on medial collateral ligaments of the knee.

In an embodiment, a knee joint prosthesis for implantation in the knee of a patient may comprise a tibial component configured to be implanted on the tibia, a femoral component configured to be implanted on the femur, wherein the femoral component comprises a medial condyle with a medial articulation surface and a lateral condyle with a lateral articulation surface. The femoral component and the tibial component may be shaped such that, after implantation in the knee, the femoral component and the tibial component engage at a medial dwell point and a lateral dwell point, wherein the medial dwell point migrates medially and/or the lateral dwell point migrates laterally during flexion of the knee.

The tibial component may comprise a medial articulation side and a lateral articulation side. The medial articulation side may comprise a medial side height differential defined by a posterior side with a first height, and an anterior side with a second height. The lateral articulation side may comprise a lateral side height differential defined by a posterior side with a third height and an anterior side with a fourth height. The medial side height differential may be greater than the lateral side height differential.

The first height may be greater than the third height.

The medial side height differential may be greater than the lateral edge height differential causing a medial pivot of the tibia. During flexion, the medial dwell point may migrate medially to maintain tension of medial collateral ligaments on a medial side of the knee joint.

In an embodiment, a knee joint prosthesis may comprise a tibial component configured to be implanted on the tibia, a femoral component configured to be implanted on the femur. The femoral component may comprise a medial condyle with a medial articulation surface and a lateral condyle with a lateral articulation surface. The tibial component may comprise an articulation surface with a medial articulation side and a lateral articulation side. The medial articulation side and the lateral articulation side may be shaped to articulate with the medial articulation surface and the lateral articulation surface, respectively, such that during flexion, the knee joint may be stabilized by a maintenance of tension of medial collateral ligaments.

The maintenance of tension may further comprise the lateral collateral ligament.

The medial articulation side may comprise a medial height differential defined by a posterior section with a first height and an anterior section with a second height. The lateral articulation side may comprise a lateral height differential defined by a posterior section with a third height and an anterior section with a fourth height. The first height may be greater than the third height and the medial height differential is greater than the lateral height differential.

BRIEF DESCRIPTION OF THE DRAWINGS

The advantages, nature, and additional features of exemplary embodiments of the disclosure will become more fully apparent from the following description and appended claims, taken in conjunction with the accompanying drawings. Understanding that these drawings depict only exemplary embodiments and are, therefore, not to be considered limiting of the disclosure's scope, the exemplary embodiments of the disclosure will be described with additional specificity and detail through use of the accompanying drawings in which:

FIG. 11A is a perspective rear view of another tibial insert of the disclosure; FIG. 11B is a top view of the tibial insert of FIG. 11A; FIG. 11C is a posterior view of the tibial insert of FIG. 11A; FIG. 11D is an anterior view of the tibial insert of FIG. 11A; FIG. 11E is a bottom view of the tibial insert of FIG. 11A;

FIG. 13 is a chart demonstrating the interchangeability of the tibial inserts disclosed herein with various femoral components;

It is to be understood that the drawings are for purposes of illustrating the concepts of the disclosure and may not be to scale. Furthermore, the drawings illustrate exemplary embodiments and do not represent limitations to the scope of the disclosure.

DETAILED DESCRIPTION

Exemplary embodiments of the disclosure will be best understood by reference to the drawings, wherein like parts are designated by like numerals throughout. It will be readily understood that the components of the disclosure, as generally described and illustrated in the Figures herein, could be arranged and designed in a wide variety of different configurations. Thus, the following more detailed description of the embodiments of the apparatus, instruments, systems, and methods, as represented in the Figures, is not intended to limit the scope of the disclosure, as claimed, but is merely representative of exemplary embodiments of the disclosure.

Disclosed herein are components for a modular knee prosthesis system. This system may allow for revision procedures by replacement of only the tibial insert, allowing the originally implanted femoral and tibial anchoring components to remain implanted. The system may include CR tibial inserts, PS tibial inserts, and/or CCK tibial inserts. Any one of these tibial inserts may be interchangeably used with CR and/or PS femoral components disclosed herein to provide the stabilization needed to substitute for compromised or removed ligaments. The system may be used with any suitable tibial baseplate component, or tibial tray, to support the tibial insert. The PS tibial inserts disclosed herein may include tapered posts that permit the inserts to be used with cruciate retaining (CR) femoral components and/or posterior stabilizing (PS) femoral components.

Figure 1A:
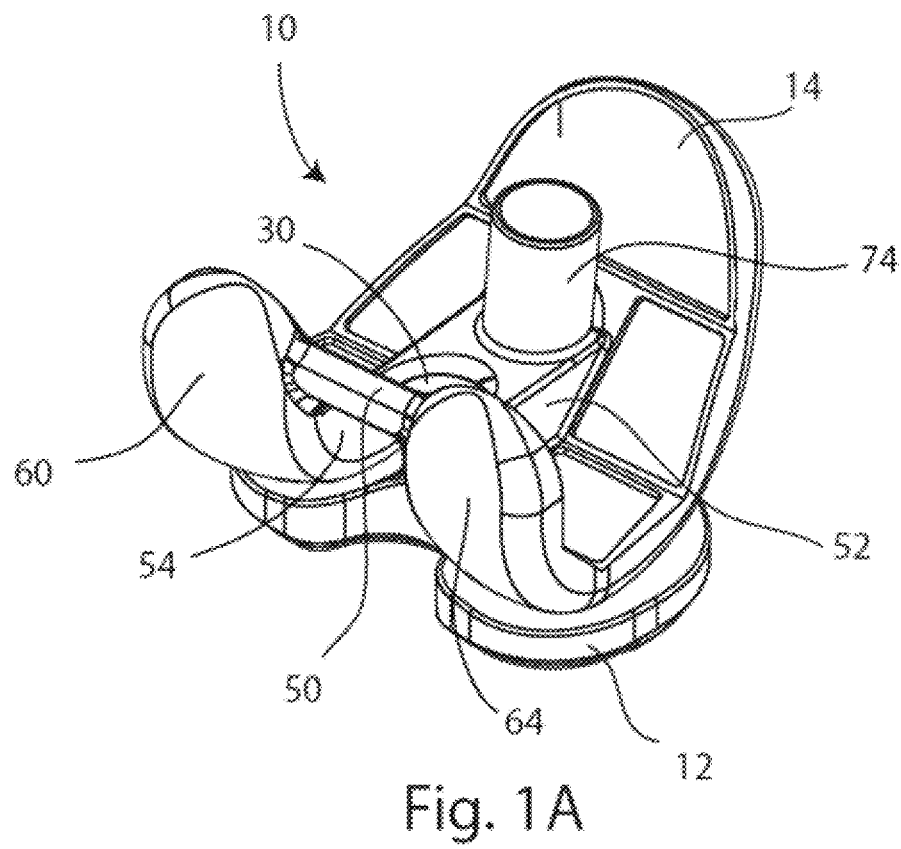
FIG. 1A is a perspective rear view of an assembly of the disclosure, including a posterior stabilizing femoral component and a tibial insert coupled in extension.
Figure 1B:
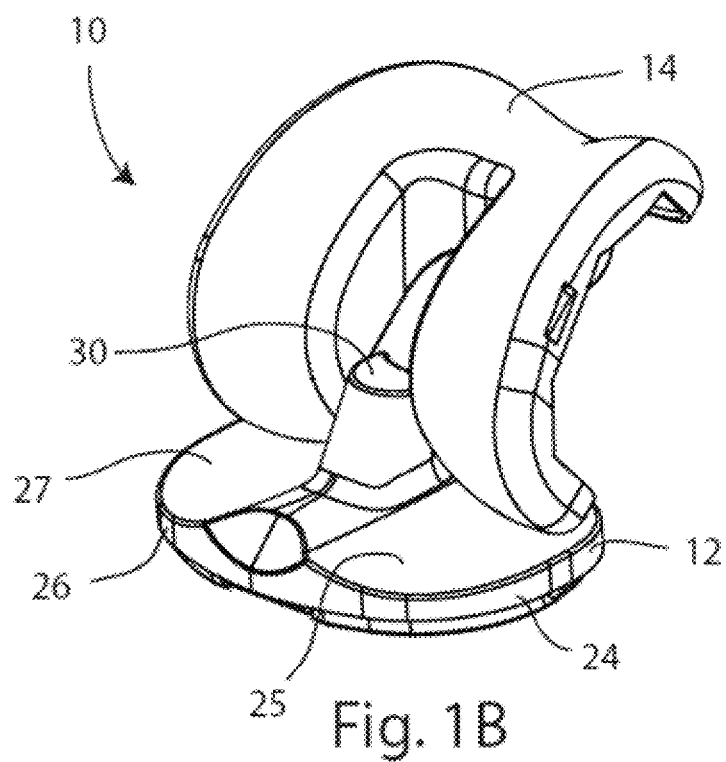
FIG. 1B is a perspective front view of the assembly of FIG. 1A in flexion.
Figure 2:
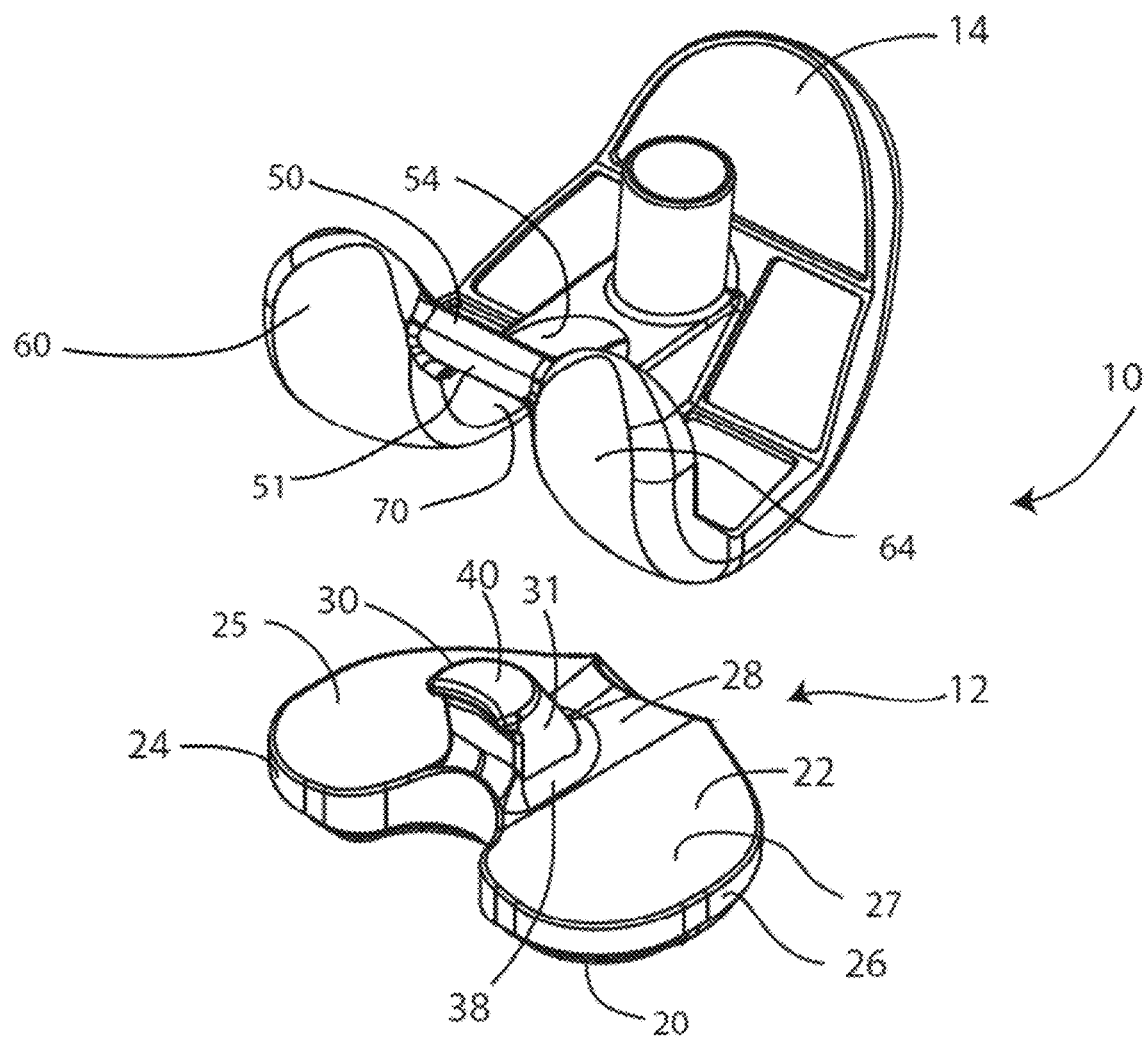
FIG. 2 is an exploded view of the assembly of FIG. 1A.

Referring to FIGS. 1A-2, an assembly 10 for an implantable knee prosthesis is shown including a femoral component 14 and a tibial insert 12. The femoral component 14 and tibial insert 12 are shown coupled in extension in FIG. 1A, coupled in flexion in FIG. 1B, and shown in an exploded view in FIG. 2. The tibial insert 12 may be further coupled to a tibial baseplate component (not shown) which may be implanted in a prepared tibia of a patient (also not shown). The femoral component 14 and tibial insert 12 illustrated in FIGS. 1A-2 are right femoral and tibial insert components. Left femoral and tibial insert components (not shown) would be mirror images of the right femoral and tibial insert components shown in FIGS. 1A-2. The femoral component 14 may also be referred to as a posterior stabilizing femoral component 14 (or "PS femoral component") and the tibial insert 12 may also be referred to as a posterior stabilizing tibial insert (or "PS insert").

FIGS. 3A-3D show the PS insert 12 of FIGS. 1A-2 in isolation. The PS insert 12 may include a fixation side 20, which may be an inferior side, opposite an articulation side 22, which may be a superior side. The articulation side 22 may include a medial articulation portion 24 having a medial condylar articulation surface 25 and a lateral articulation portion 26 having a lateral condylar articulation surface 27. A central portion 28 may separate the medial articulation portion 24 from the lateral articulation portion 26. A post 30 may protrude superiorly from the central portion 28 and extend from a post base 38 to a post top or post superior end 40. From the anterior perspective (shown in FIG. 3B) and/or the posterior perspective (shown in FIG. 3A), the post 30 may have its maximum medial-lateral or horizontal width toward the post superior end 40 of the post 30, and its minimum medial-lateral or horizontal width toward the post base 38 of the post 30. The post 30 may also be bilaterally symmetrical from the anterior and/or posterior perspectives. A recess 45 may be formed posterior to the central portion 28, between the medial and lateral articulation portions 24, 26, and may provide room for a posterior cruciate ligament (not shown). The PS insert 12 may further include an insert base 46, which may further include an engagement feature 48 for engagement with a tibial baseplate component.

Figure 3A:
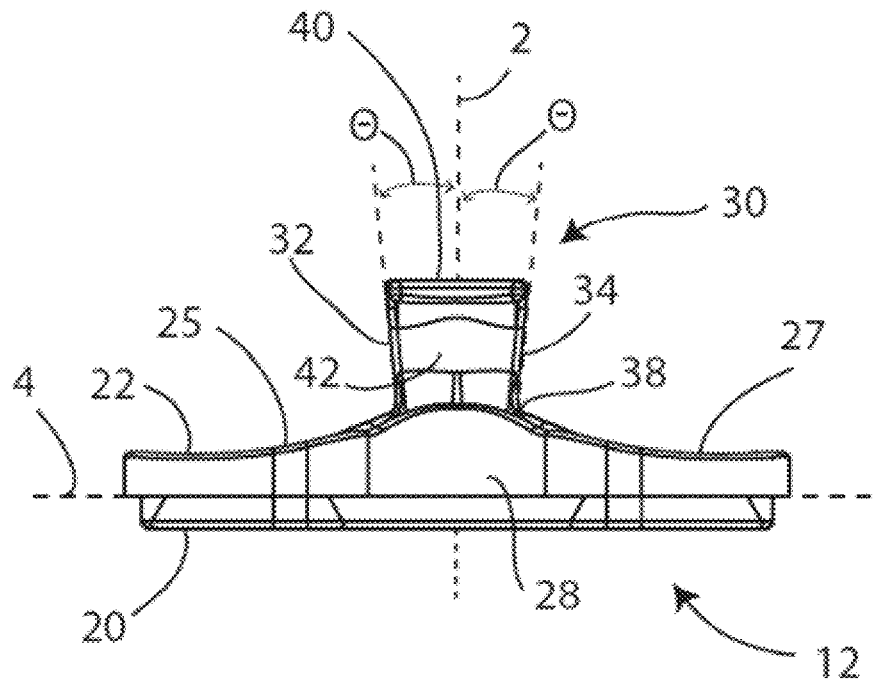
FIG. 3A is a posterior view of the tibial insert of FIG. 1A.
Figure 3B:
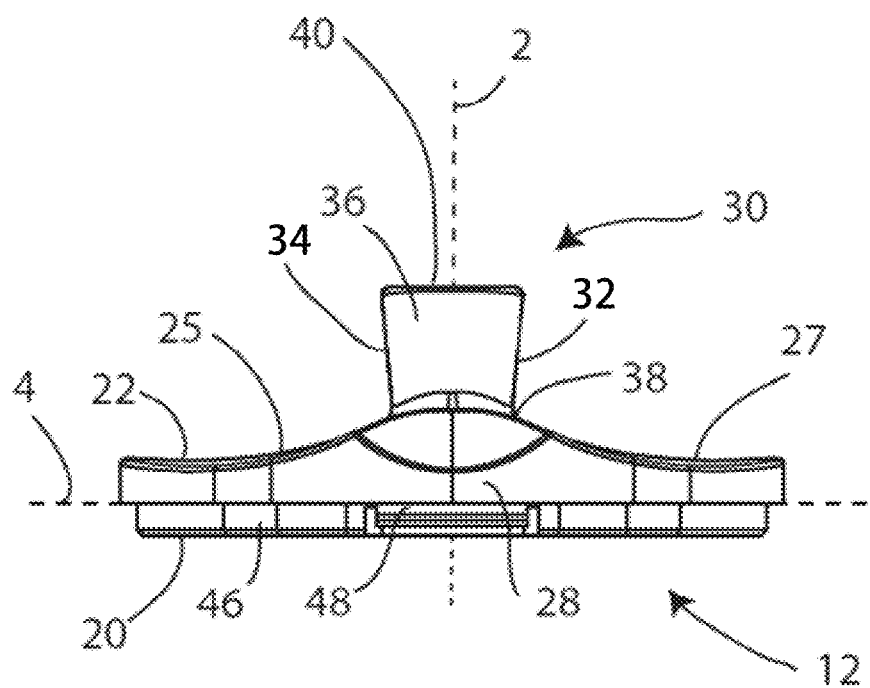
FIG. 3B is an anterior view of the tibial insert of FIG. 1A.
Figure 3C:
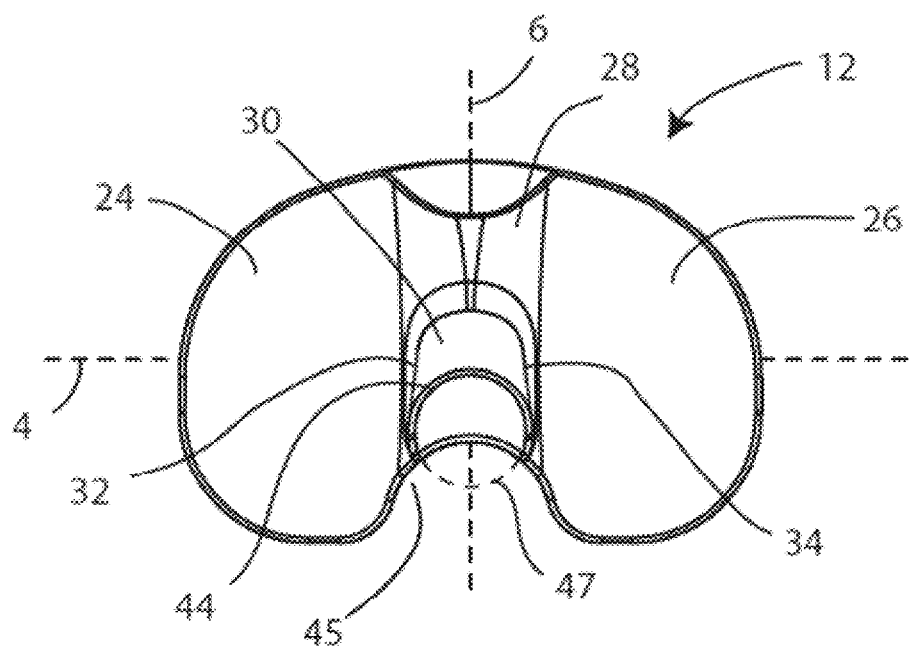
FIG. 3C is a superior view of the tibial insert of FIG. 1A.
Figure 3D:
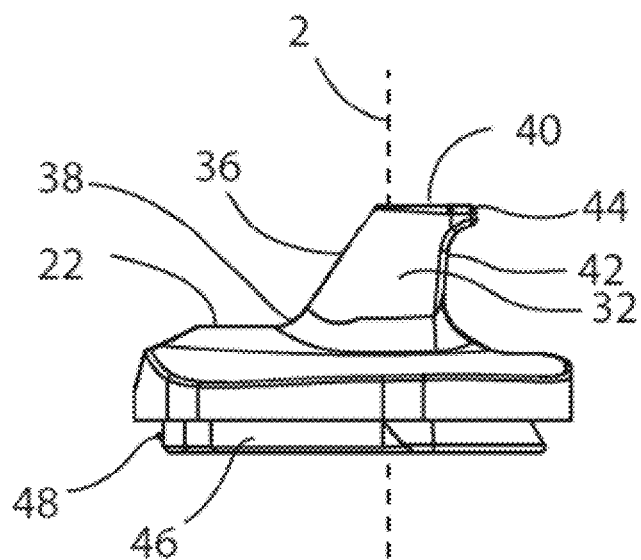
FIG. 3D is a medial side view of the tibial insert of FIG. 1A.
Figure 4:
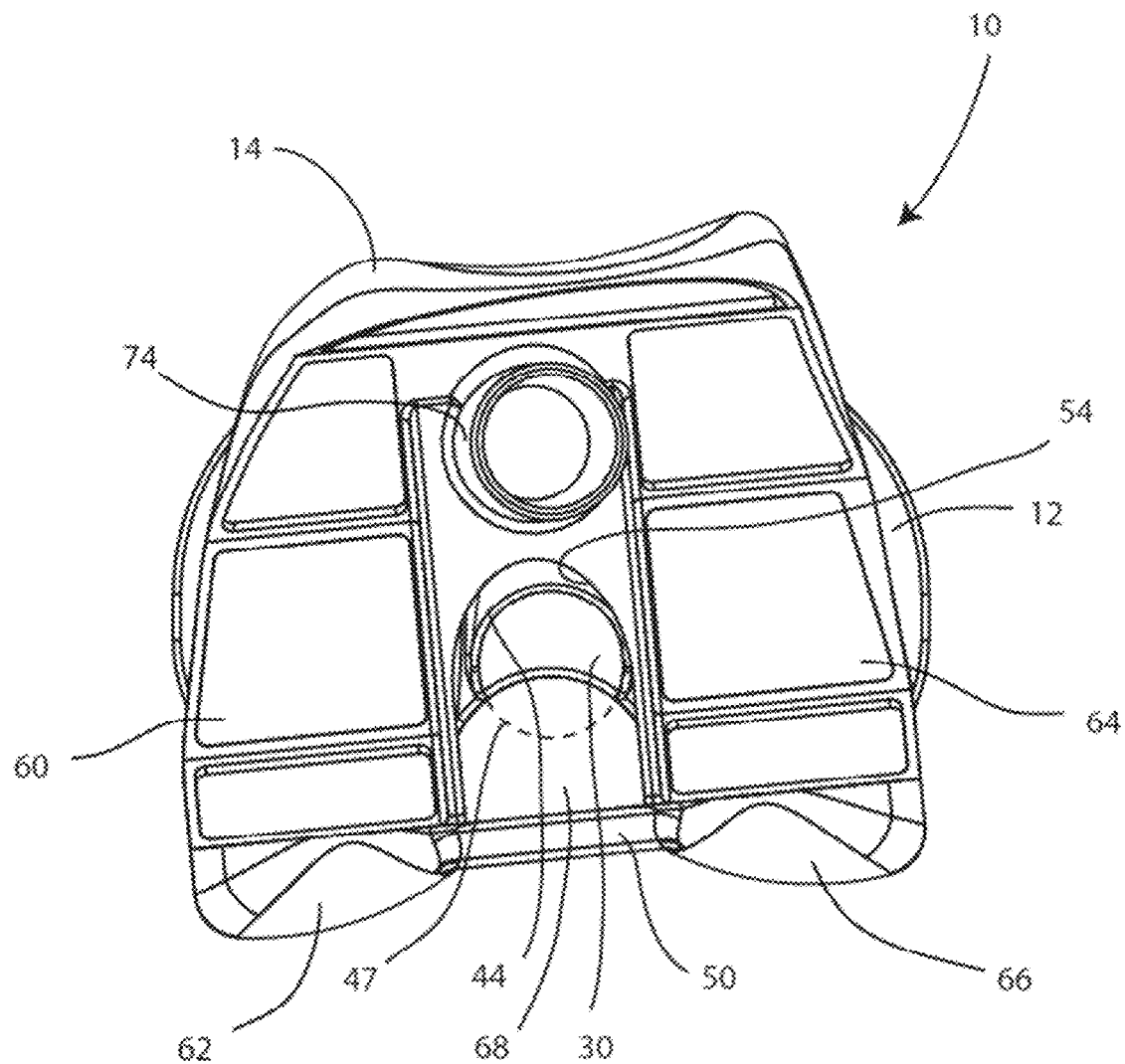
FIG. 4 is a top down view of the assembly of FIG. 1A.
Figure 5:
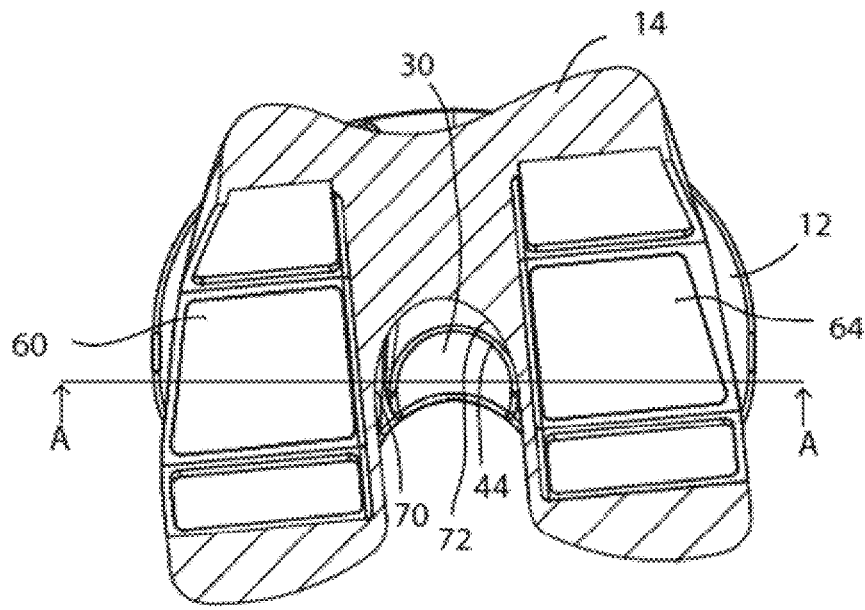
FIG. 5 is a top down cross-sectional view of the assembly of FIG. 1A, taken along line B-B in FIG. 6.
Figure 6:
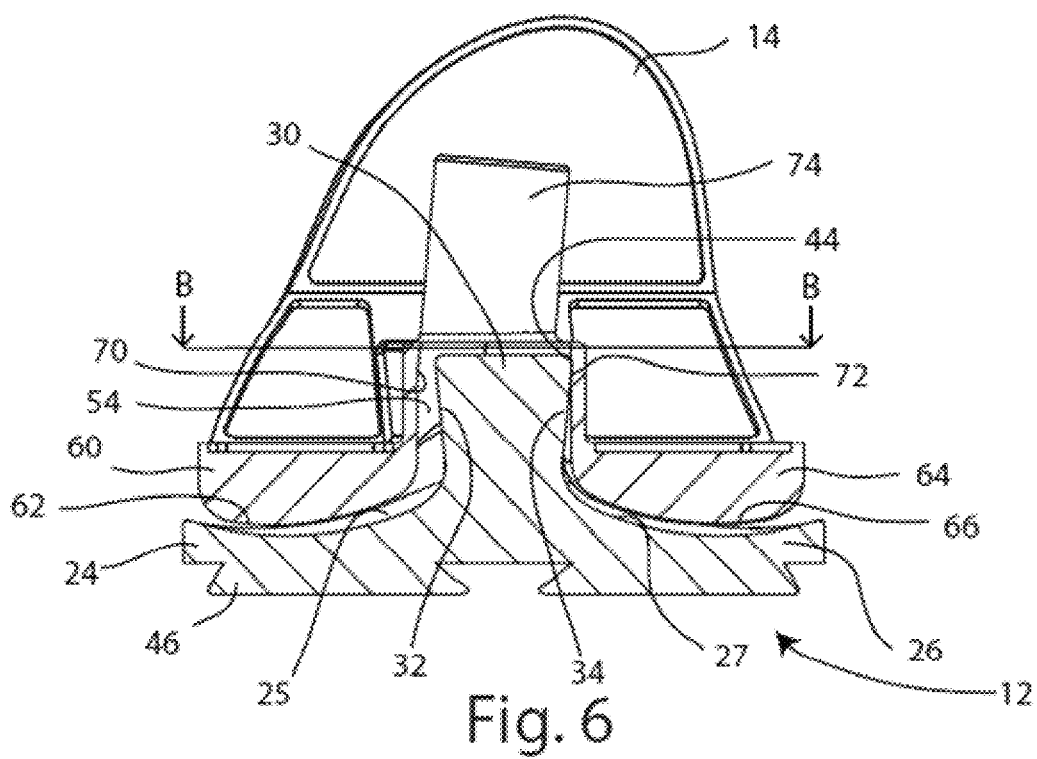
FIG. 6 is a posterior cross-sectional view of the assembly of FIG. 1A, taken along line A-A in FIG. 5.
Figure 7:
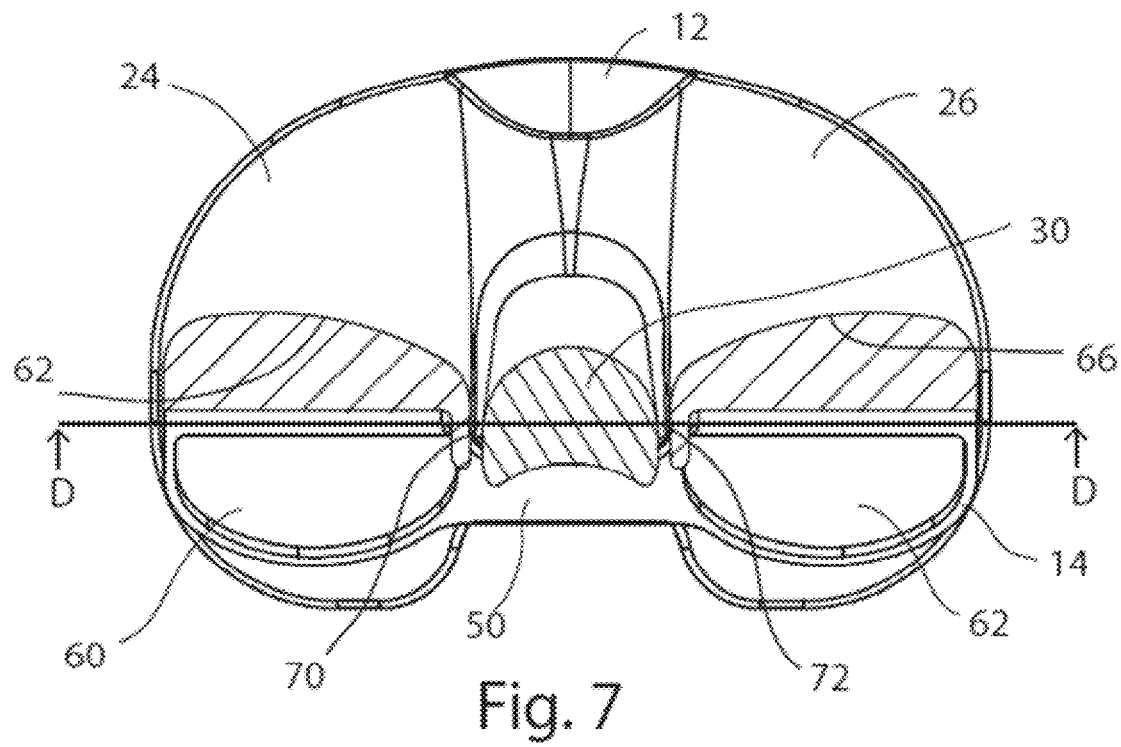
FIG. 7 is a top down cross-sectional view of the assembly of FIG. 1B, taken along line C-C in FIG. 8.
Figure 8:
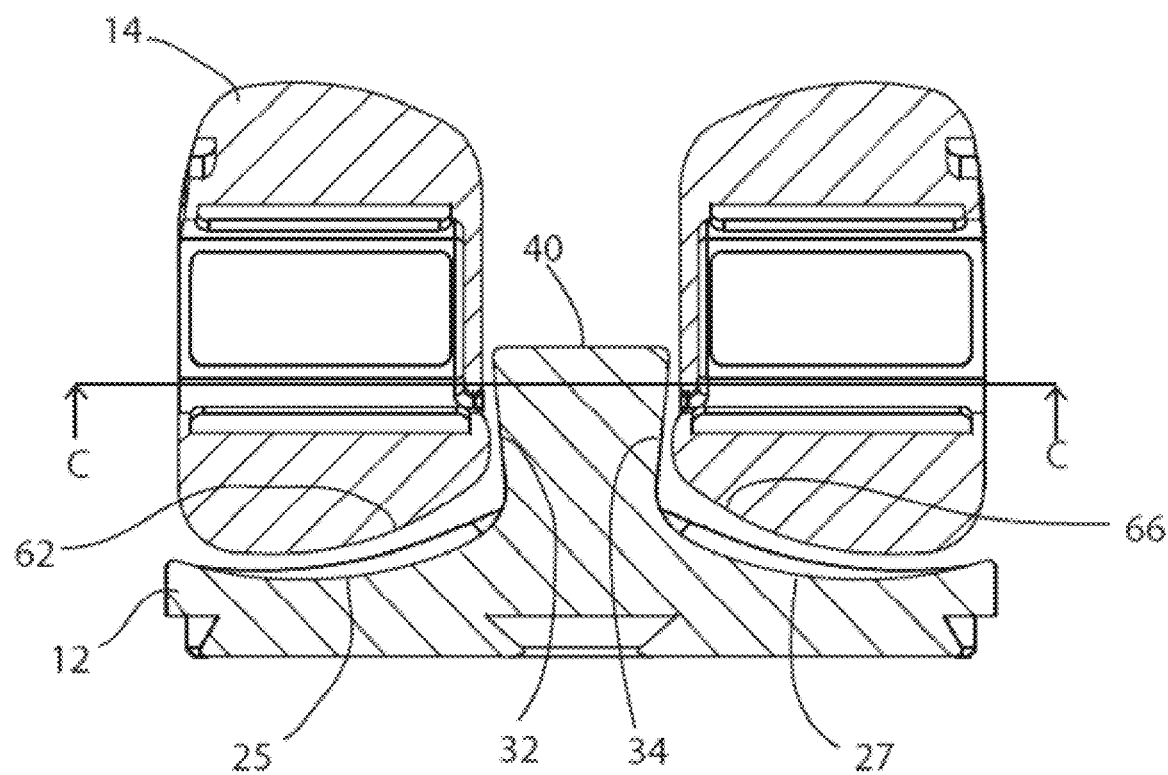
FIG. 8 is a posterior cross-sectional view of the assembly of FIG. 1B, taken along line D-D in FIG. 7.

Continuing with FIGS. 1A-3D, the post 30 may have an articulation surface 31 extending around the post 30 on the medial, posterior, lateral, and anterior aspects of the post 30. The articulation surface 31 may include a medial articulation surface 32, a lateral articulation surface 34, an anterior post surface 36, and a posterior articulation surface 42. The medial and lateral articulation surfaces 32, 34 may be non-parallel to one another and taper inward from the post superior end 40 to the post base 38 relative to an insert midline vertical axis 2, as shown in FIGS. 3A and 3B. As shown in FIG. 3A, an angle θ between the vertical axis 2 and each tapered surface 32, 34 may be about 6.5°, in at least one embodiment. Since the post 30 may be bilaterally symmetrical, the angle θ may be the same on both the medial and lateral articulation surfaces 32, 34 of the post 30. In other embodiments of the disclosure, angle θ may range from about 6° to 11° degrees. The medial articulation surface 32 may be continuous with the medial condylar articulation surface 25, and the lateral articulation surface 34 may be continuous with the lateral condylar articulation surface 27, as can been further seen in cross-section in FIGS. 6 and 8. The anterior post surface 36 may extend between the medial and lateral articulation surfaces 32, 34 and may be convexly rounded. The anterior post surface 36 may also taper outward from the post superior end 40 to the post base 38 relative to the midline vertical axis 2, as best seen in FIG. 3D. In other embodiments of the PS insert 12, the anterior post surface 36 may include less or no taper.

Referring to FIG. 3C, the boundary of the post superior end 40 defines a rounded rim 44 shaped as a portion of a circle defined by a circular envelope 47, as seen from a superior perspective. The post superior end 40 and rim 44 may be crescent-shaped with a concave recess toward a posterior end of the post 30 as shown, and may permit passage of the posterior cruciate ligament. The post superior end 40 may be circular; the rim 44 may provide increased rotational range of motion and surface contact against the femoral component 14 in comparison to traditional posts with a more square or rectangular shape and no rim. Thus, the rounded post superior end 40 and rim 44 may allow for surface contact with the femoral component 14 in contrast to the mere point or edge contact that is achieved by traditional posts that do not have these features.

The PS femoral component 14 depicted in FIGS. 1-8 may include a cam element or cam bar 50 and a box structure 52 for providing posterior stabilization in place of absent ligaments. The cam bar 50 may include a cam articulating surface 51 which may contact the posterior articulation surface 42 of the post 30 during flexion, as in FIGS. 1B and 7. An internal articulation surface 54 may reside on the inside of the box structure 52 and may contact the post 30 during articulation and rotation of the knee joint. The internal articulating surface 54 may be concavely curved, and may contact the rim 44 of the post 30 during axial rotation of the knee joint about the post. The PS femoral component 14 may further include a medial condyle 60 having a medial condylar articulation surface 62, and a lateral condyle 64 having a lateral condylar articulation surface 66. The medial and lateral condylar articulation surfaces 62, 66 may articulate against the PS insert 12 medial and lateral condylar articulation surfaces 25, 27, respectively. A gap 68 may be formed between the medial and lateral condyles 60, 64, with the cam bar 50 extending medial-laterally across the gap 68. The internal articulation surface 54 may include a medial portion 70 continuous with a lateral portion 72. In the embodiment depicted, a fixation post 74 may protrude superiorly from the PS femoral component 14. However, in other embodiments of the PS femoral component 14, the fixation post 74 may be absent and/or other fixation features such as posts, spikes, pegs, webs, keels, or teeth may be present to affix the PS femoral component 14 to a prepared femur (not shown).

Figure 9:
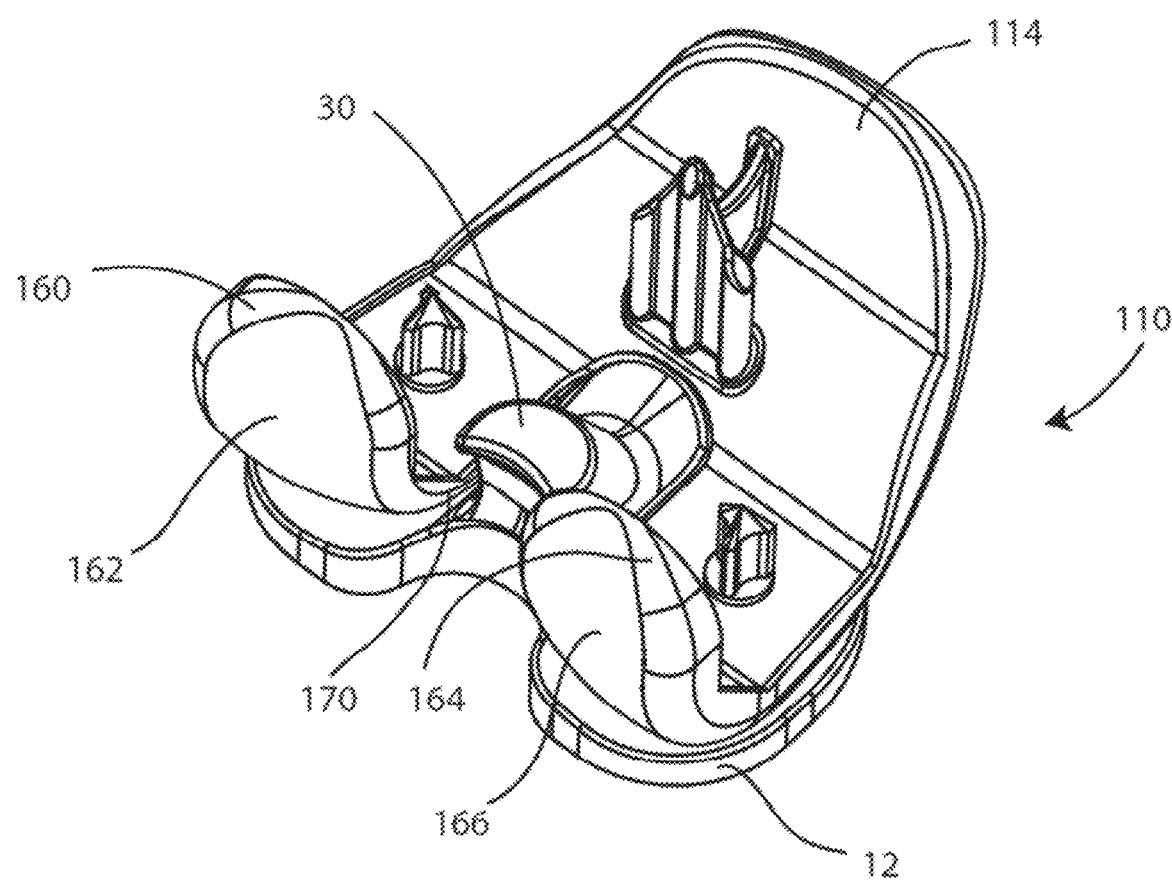
FIG. 9 is a perspective rear view of an assembly of the disclosure, including a cruciate retaining femoral component and the tibial insert of FIG. 1A coupled in extension.
Figure 10:
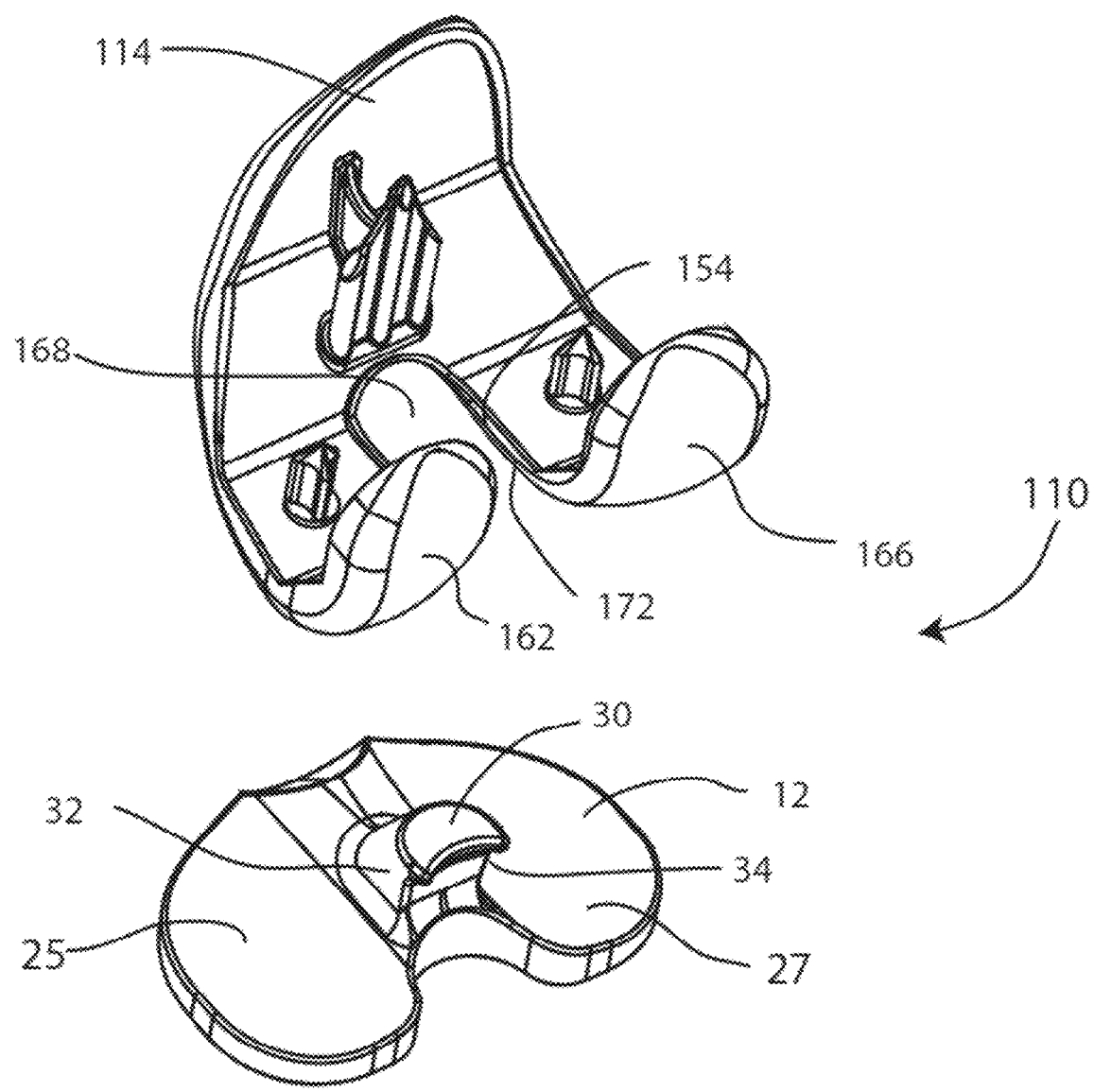
FIG. 10 is an exploded perspective rear view of the assembly of FIG. 9.

Referring to FIGS. 9 and 10, another assembly 110 embodiment of the disclosure may include the PS insert 12 of FIGS. 1-8 coupled with a cruciate retaining femoral component 114 (or "CR femoral component"). The CR femoral component 114 may include medial and lateral condyles 160, 164, with a gap 168 formed between the medial and lateral condyles 160, 164. As a CR femoral component 114, no cam bar or box may be present. The medial and lateral condyles 160, 164 may include medial and lateral condylar articulation surfaces 162, 166, and an internal articulation surface 154 with medial and lateral articulating surfaces 170, 172.

The medial and lateral articulation surfaces 32, 34 of the post 30 may be tapered and may permit natural articulation of the CR femoral component 114 with the PS insert 12, which may not be achievable if the post 30 were not tapered. For example, if the post 30 had straight sides instead of tapered sides, the wider width of the post 30 at the base of the post 30 would interfere with the internal articulating surfaces 170, 172 of the medial and lateral condyles 160, 164. When the PS femoral component 14 is coupled with the PS insert 12 to form assembly 10, as in FIG. 1A and FIG. 4, the circular shape of the post superior end 40 in combination with the tapered medial and lateral articulation surfaces 32, 34 of the post 30, may permit the PS femoral component 14 to articulate relative to the PS insert 12 in the manner of a posterior stabilized femoral component. However, when the PS insert 12 is paired and implanted with the CR femoral component 114, the resultant assembly 110 may provide the native articulation and rotation of a cruciate retaining implant.

Referring to FIGS. 11A-11E, an alternative embodiment of a tibial insert 212 is shown. Tibial insert 212 may be referred to as a cruciate retaining tibial insert 212 (or "CR insert"). In a system of the disclosure, CR insert 212 may be implanted with the CR femoral component 114 and a tibial baseplate component (not shown) to form a cruciate retaining knee prosthesis system. The CR insert 212 may include a fixation side 220, which may be an inferior side, opposite an articulation side 222, which may be a superior side. The articulation side 222 may include a medial articulation portion 224 having a medial condylar articulation surface 225 and a lateral articulation portion 226 having a lateral condylar articulation surface 227. A central portion 228 may separate the medial articulation portion 224 from the lateral articulation portion 226. A recess 245 may be formed posterior to the central portion 228, between the medial and lateral articulation portions 224, 226, and may provide room for a posterior cruciate ligament. The CR insert 212 may further include an insert base 246 and an engagement feature 248 for engagement with a tibial baseplate component. The CR insert 212 may be coupled with the CR femoral component 114 to form a cruciate retaining assembly. This assembly may be implanted with a suitable tibial baseplate as a cruciate retaining knee prosthesis. The CR insert 212 may also be coupled with the PS femoral component 14 and implanted with a suitable tibial baseplate.

Figure 12A:
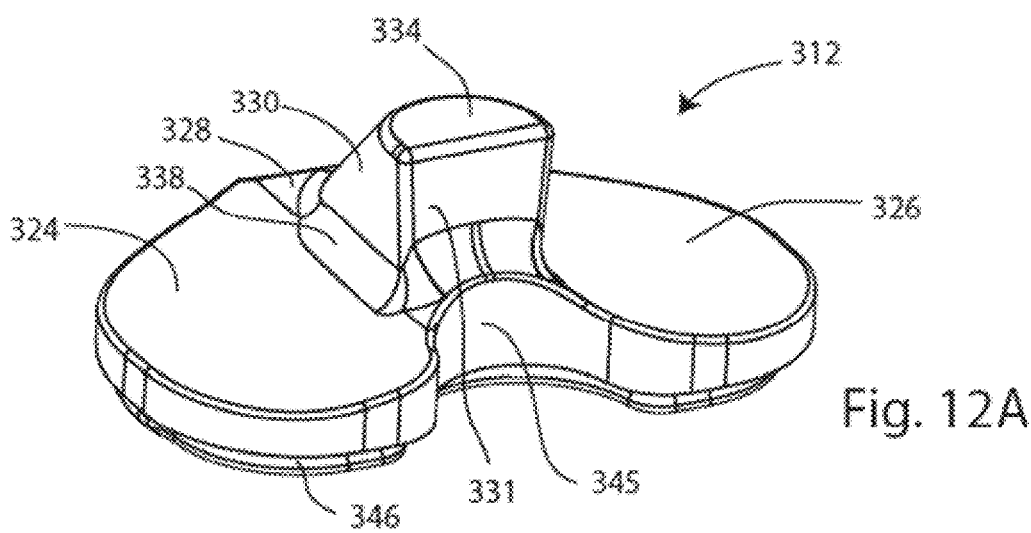
FIG. 12A is a perspective rear view of another tibial insert of the disclosure.
Figure 12B:
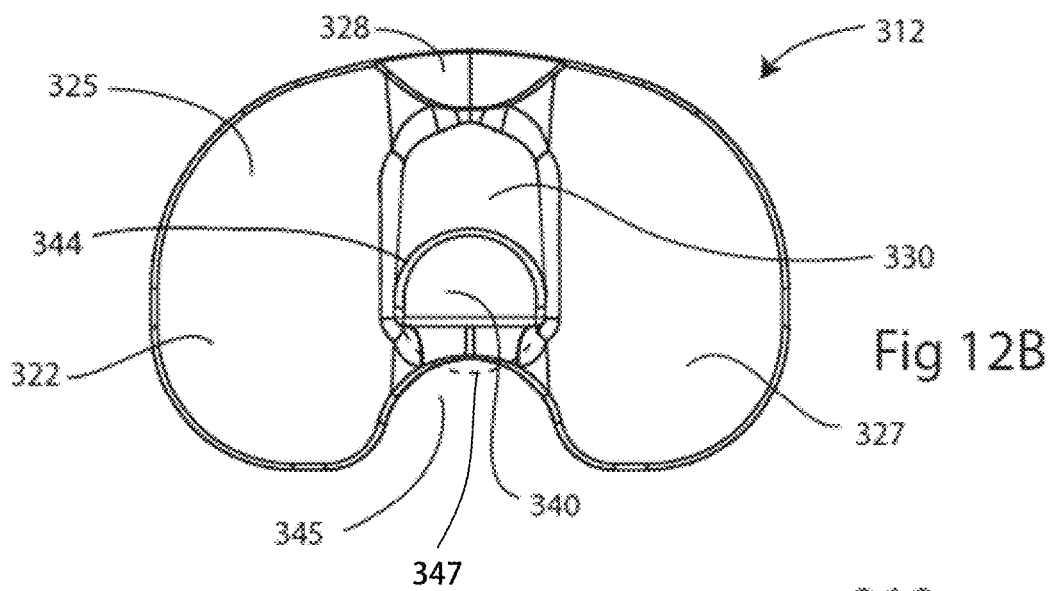
FIG. 12B is a top view of the tibial insert of FIG. 12A.
Figure 12C:
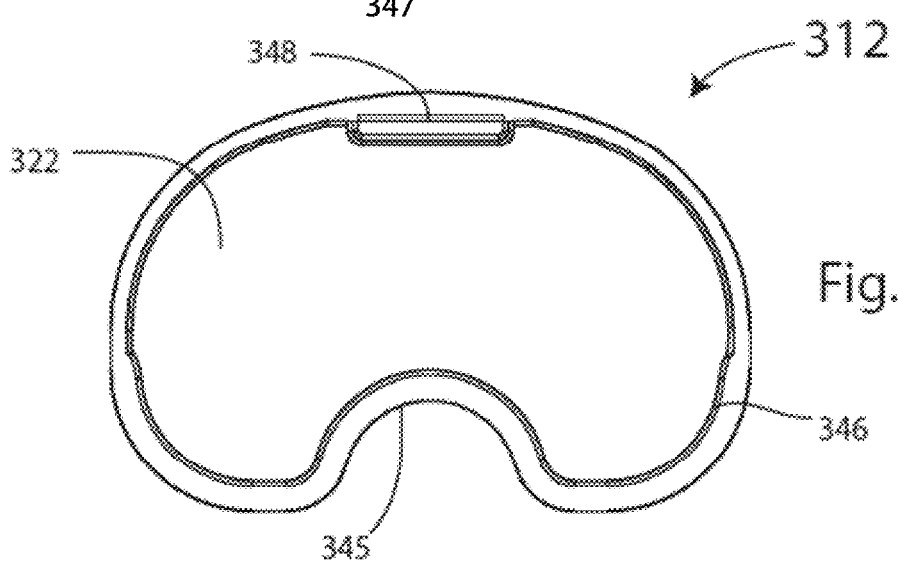
FIG. 12C is a bottom view of the tibial insert of FIG. 12A.
Figure 12D:
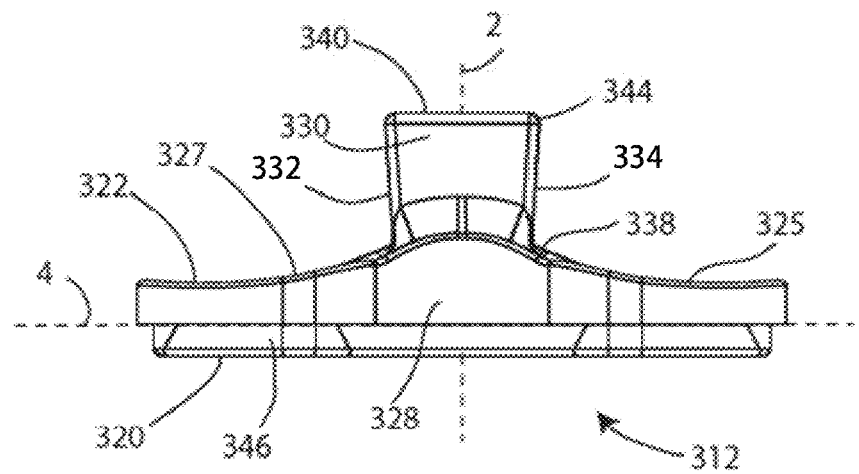
FIG. 12D is a posterior view of the tibial insert of FIG. 12A.
Figure 12E:
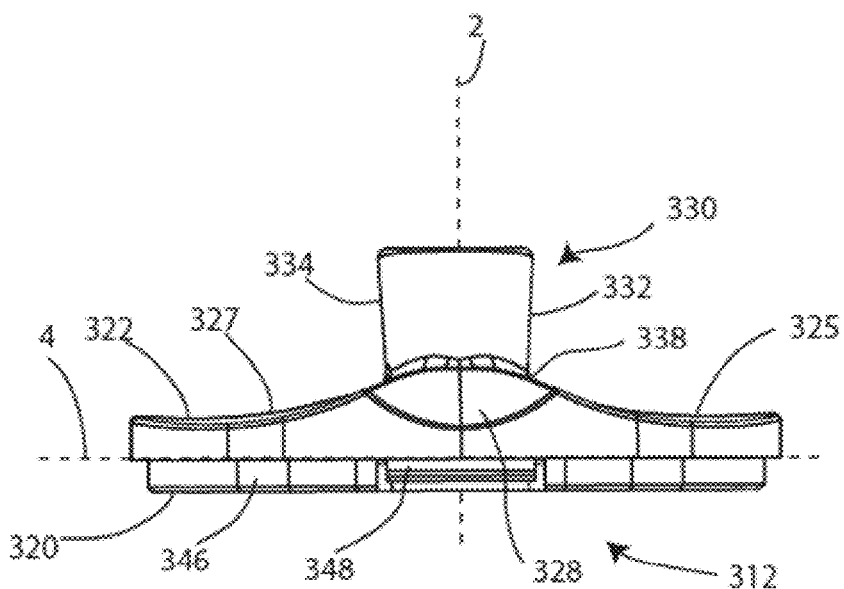
FIG. 12E is an anterior view of the tibial insert of FIG. 12A.

Referring to FIGS. 12A-12F, another alternative embodiment of a tibial insert 312 is shown. The tibial insert 312 may be referred to as a constrained condylar knee (CCK) tibial insert 312 (or "CCK insert"). The CCK insert 312 may include a fixation side 320, which may be an inferior side, opposite an articulation side 322, which may be a superior side. The articulation side 322 may include a medial articulation portion 324 having a medial condylar articulation surface 325 and a lateral articulation portion 326 having a lateral condylar articulation surface 327. A central portion 328 may separate the medial articulation portion 324 from the lateral articulation portion 326. A post 330 may protrude superiorly from the central portion 328, and extend from a post base 338 to a top, or post superior end 340. From the anterior perspective, as shown in FIG. 12E, and the posterior perspective, as shown in FIG. 12D, the post 330 may have its maximum medial-lateral or horizontal width at the superior end 340 of the post 330, and its minimum medial-lateral or horizontal width at the post base 338 of the post 330. The post 330 may be bilaterally symmetrical from the anterior and posterior perspectives. The CCK insert 312 may further include an insert base 346 and an engagement feature 348 for engagement with a tibial tray (not shown).

Figure 12F:
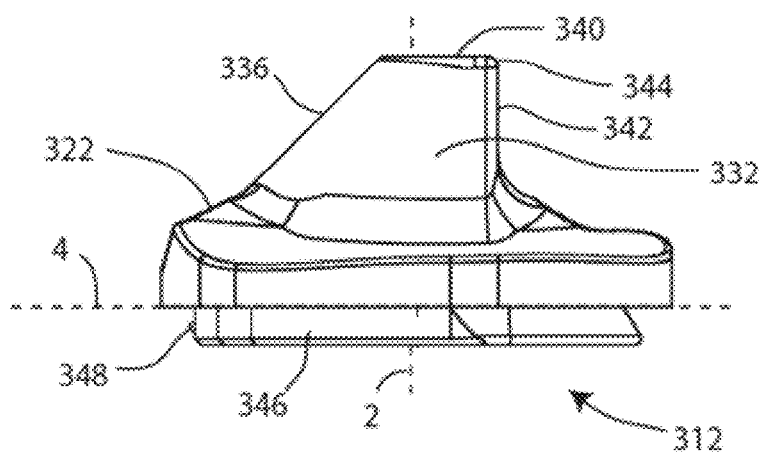
FIG. 12F is a medial side view of the tibial insert of FIG. 12A.

The post 330 may have an articulation surface 331 extending around the post 330 on the medial, posterior, lateral, and anterior aspects of the post 330. The articulation surface 331 may include a medial articulation surface 332, a lateral articulation surface 334, an anterior post surface 336, and a posterior articulation surface 342. The medial and lateral articulation surfaces 332, 334 may taper slightly inward from the post superior end 340 to the post base 338 of the post 330 relative to an insert midline vertical axis 2. However, some embodiments of CCK insert 312 may include no taper of the medial and lateral articulation surfaces 332, 334. The medial articulation surface 332 may be continuous with the medial condylar articulation surface 325, and the lateral articulation surface 334 may be continuous with the lateral condylar articulation surface 327. The anterior post surface 336 may extend between the medial and lateral surfaces 332, 334 and may be convexly rounded. The anterior post surface 336 may taper outward from the post superior end 340 to the post base 338 relative to the midline axis 2, as best seen in FIG. 12F. In other embodiments of the CCK insert 312, the anterior post surface 336 may include less taper, more taper, and/or no taper. The post 330 of the CCK insert 312 may be wider and bigger in diameter than the post 30 of PS insert 12, for example to provide increased stability in the case of removal of the collateral ligaments.

Referring to FIG. 12B, the boundary of the post superior end 340 may define a rounded rim 344 shaped as a portion of a circle, from a superior perspective. The post superior end 340 and rim 344 may be semi-circular as shown, however the rim 344 may define a circular envelope 347. The post superior end 340 may be circular and rim 344 may provide increased surface contact and rotational range of motion when coupled and implanted with the PS femoral component 14 in comparison to traditionally shaped posts with a more square or rectangular shaped post. Thus, the rounded post superior end 340 and rim 344 may allow for surface contact with the femoral component 14 in contrast to the mere point or edge contact that is achieved by traditional posts that do not have these features. The CCK insert 312 may be coupled with the PS femoral component 14 to form a constrained condylar knee assembly, and this assembly may be implanted with a suitable tibial baseplate as a constrained condylar knee prosthesis. The CCK insert 312 may also be coupled with the CR femoral component 114 and implanted with a suitable tibial baseplate. Thus, all of the tibial inserts 12, 212, and 312 disclosed herein are interchangeable with both the CR femoral component 114 and the PS femoral component 14. FIG. 13 is a chart showing the potential combinations of components.

The tibial inserts 12, 212, 312, PS femoral component 14 and CR femoral component 114 may be grouped together as a modular knee replacement system and provided as a kit in one or more packages, in one non-limiting example. Another kit may include a CR femoral component 114, a PS insert 12 and a CR insert 212, in one or more packages in another non-limiting example. Yet another kit may include a PS femoral component 14, a PS insert 12, a CR insert 212, and a CCK insert 312, in one or more packages in yet another non-limiting example. However, it will also be understood that other kit embodiments may utilize any of the tibial inserts and/or femoral components described herein in any number or combination, in one or more packages. Furthermore, other components may also be including in any kit described herein, such as suitable tibial baseplate components, patellar components, etc., in one or more packages. It will also be understood that any of the tibial inserts disclosed herein may be formed of vitamin E polyethylene, highly cross linked polyethylene, ultra-high molecular weight polyethylene (UHMWPE), or any other suitable material.

In a method of the disclosure, a patient may initially experience compromise of the anterior cruciate ligament. The ACL may be removed, and a CR type prosthesis may be implanted, including a CR femoral component 114, a CR insert 212, and a tibial baseplate component. Later, the same patient may experience compromise of the PCL and may need additional stabilization of the knee joint. The PCL may be removed, the CR tibial insert 212 may be removed, and a PS tibial insert 12 of the disclosure may be inserted between the originally implanted CR femoral component 114 and the tibial baseplate component, thus providing additional stability for the missing PCL. Even later, the same patient may experience instability of the collateral ligaments. The PS tibial insert 12 may be removed, and the CCK tibial insert 312 of the disclosure may be inserted between the originally implanted CR femoral component 114 and the tibial baseplate component. Thus, the patient may progress from a CR knee prosthesis, to a PS knee prosthesis, and finally to a CCK knee prosthesis without requiring replacement of the originally implanted femoral and/or tibial baseplate components. The interchangeability of the inserts 12, 212, 312 permit replacement of only the tibial insert component in order to provide increasing levels of support and stability to the knee joint.

In another method of the disclosure, a patient may initially experience compromise of both the ACL and the PCL. These ligaments may be removed, and a PS type prosthesis may be implanted, including a PS femoral component 14, a PS insert 12, and a tibial baseplate component. Later, the same patient may experience instability of the collateral ligaments. The PS insert 12 may be removed, and a CCK insert 312 may be inserted between the originally implanted PS femoral component 14 and the tibial baseplate component. Thus, the patient may progress from a PS knee prosthesis to a CCK knee prosthesis without requiring replacement of the originally implanted PS femoral component 14 and tibial baseplate component.

Figure 14:
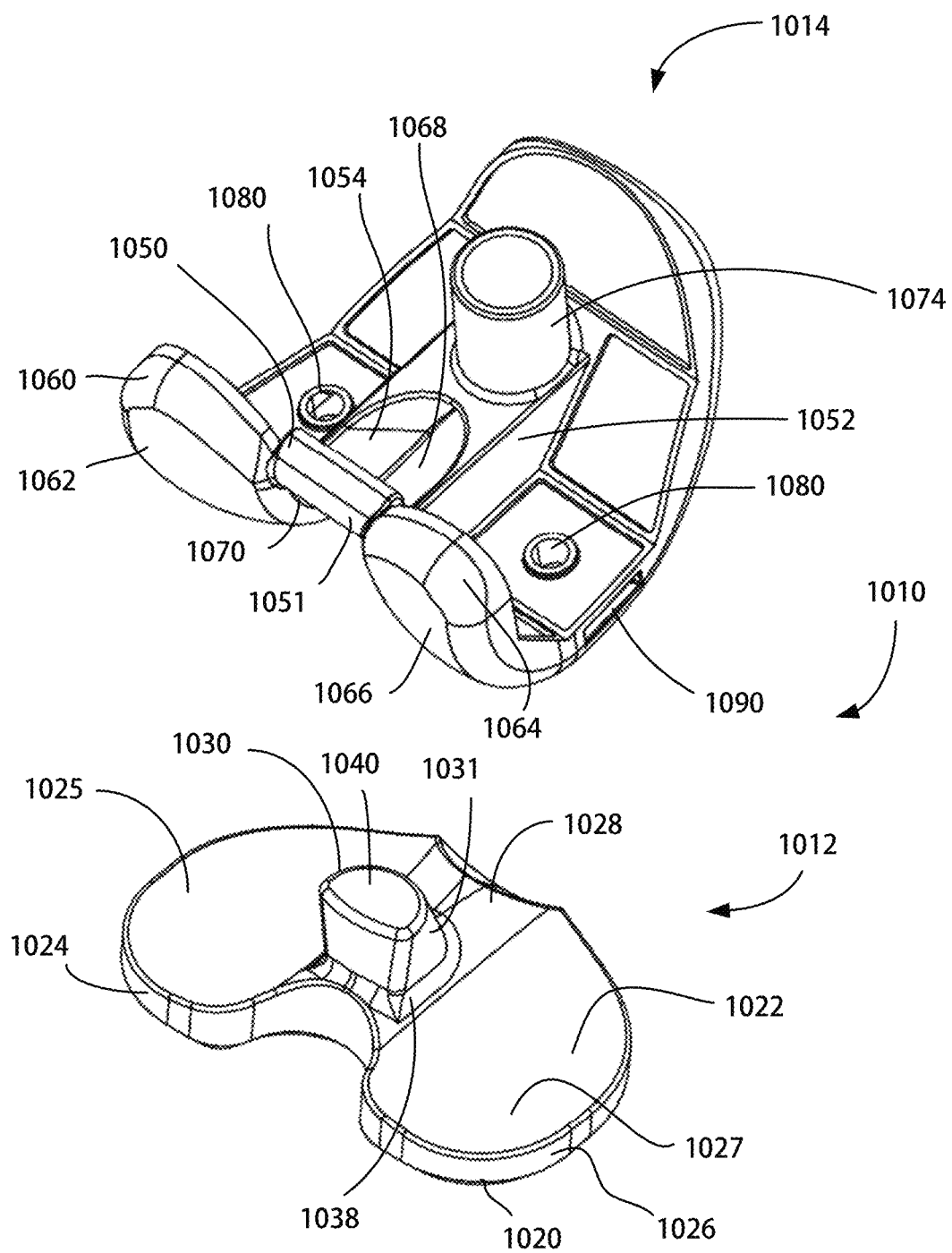
FIG. 14 is an exploded rear view of another assembly of the disclosure, including a posterior stabilizing femoral component and a posterior stabilizing tibial insert.
Figure 15:
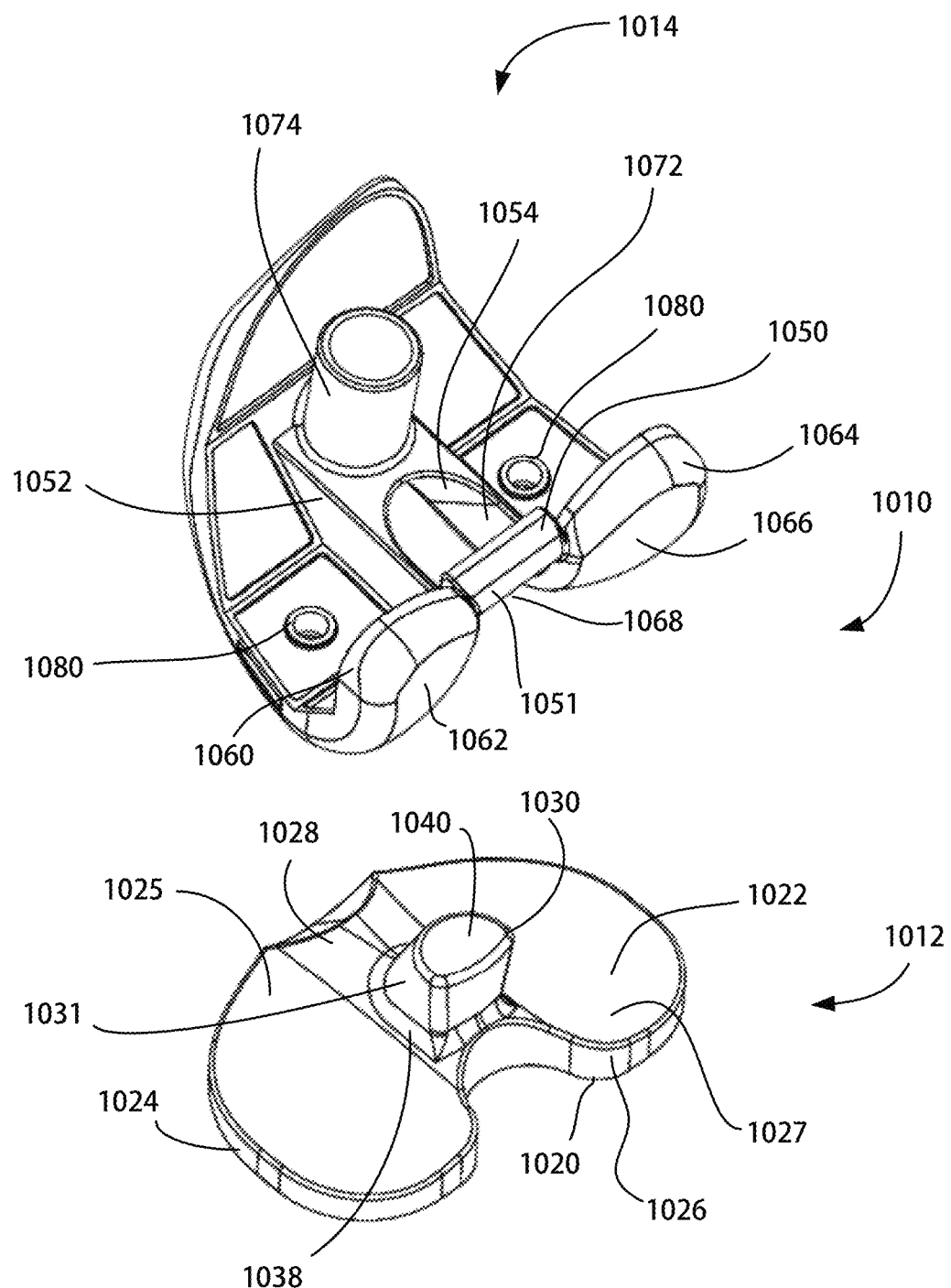
FIG. 15 is another exploded rear view of the assembly of FIG. 14.

Referring to FIGS. 14 and 15, another assembly 1010 of the disclosure for an implantable knee prosthesis is shown in various exploded rear views. The assembly 1010 may include a femoral component 1014 and a tibial insert 1012. The tibial insert 1012 may be further coupled to a tibial baseplate component (not shown) which may also be implanted in a prepared tibia of a patient (not shown). The femoral component 1014 and tibial insert 1012 illustrated in FIGS. 14 and 15 are right side femoral and tibial insert components. Left side femoral and tibial insert components (not shown) would be mirror images of the right side femoral and tibial insert components that are shown in FIGS. 14 and 15. The femoral component 1014 may also be referred to as a posterior stabilizing femoral component 1014 (or "PS femoral component") and the tibial insert 1012 may also be referred to as a posterior stabilizing tibial insert (or "PS insert").

FIGS. 16A-16D show the PS insert 1012 of FIGS. 15 and 14 in isolation. The PS insert 1012 may include a fixation side 1020, which may be an inferior side, opposite an articulation side 1022, which may be a superior side. The articulation side 1022 may include a medial articulation portion 1024 having a medial condylar articulation surface 1025 and a lateral articulation portion 1026 having a lateral condylar articulation surface 1027. A central portion 1028 may separate the medial articulation portion 1024 from the lateral articulation portion 1026. A post 1030 may protrude superiorly from the central portion 1028 and extend from a post base 1038 to a post top 1040 or post superior end. From the anterior perspective (shown in FIG. 16B) and/or the posterior perspective (shown in FIG. 16A), the post 1030 may have its maximum medial-lateral or horizontal width toward the top 1040 of the post 1030, and its minimum medial-lateral or horizontal width toward the base 1038 of the post 1030. The post 1030 may also be bilaterally symmetrical from the anterior and/or posterior perspectives. A recess 1045 may be formed posterior to the central portion 1028, between the medial and lateral articulation portions 1024, 1026, and may provide room for a posterior cruciate ligament (not shown). The PS insert 1012 may further include an insert base 1046, which may further include an engagement feature 1048 for engagement with a tibial baseplate component.

Figure 16A:
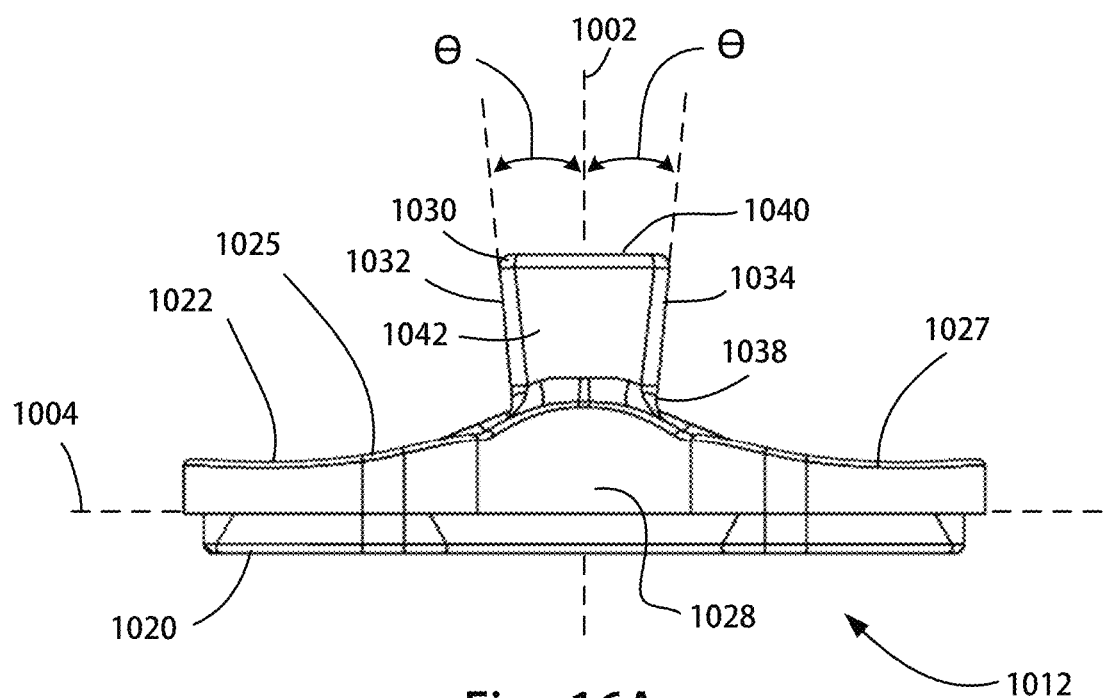
FIG. 16A is a posterior view of the tibial insert of FIG. 14.
Figure 16B:
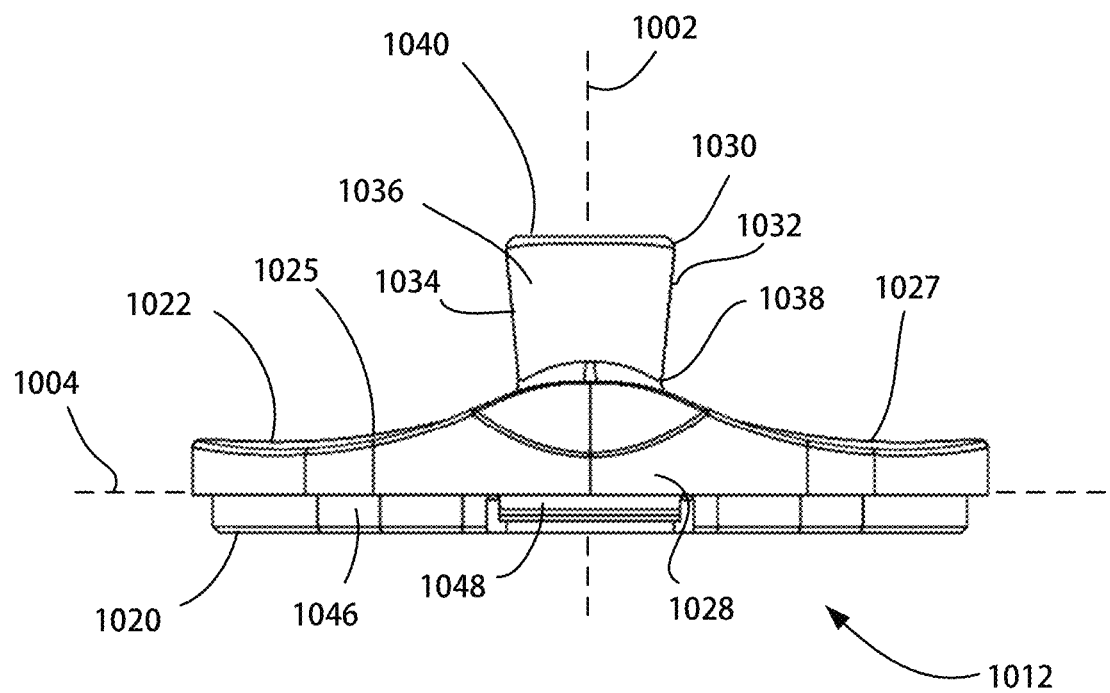
FIG. 16B is an anterior view of the tibial insert of FIG. 14.
Figure 16C:
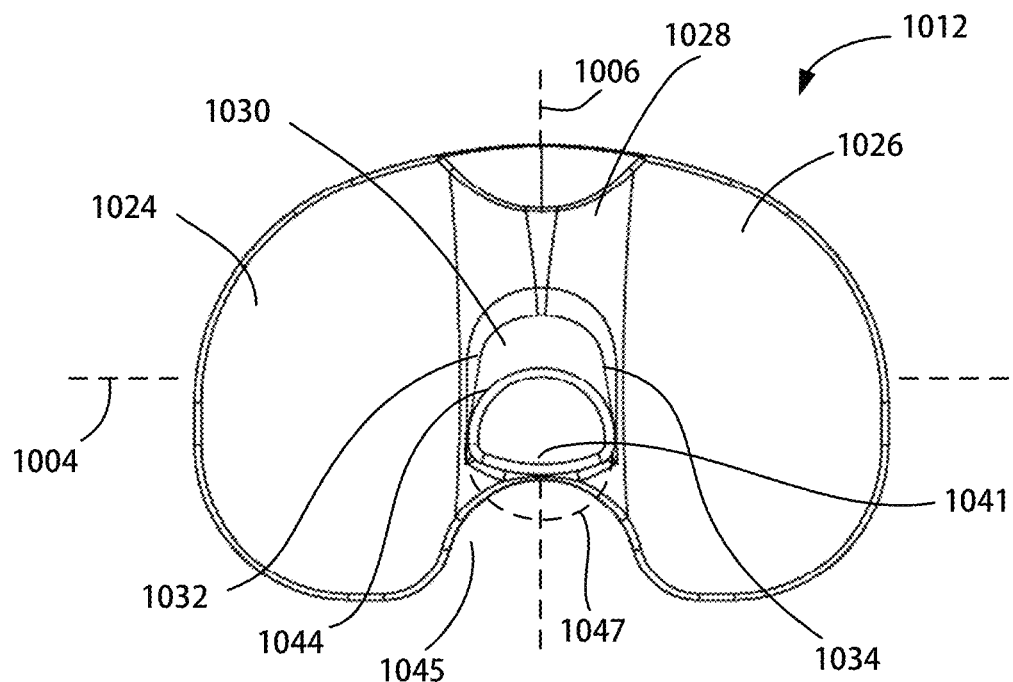
FIG. 16C is a superior view of the tibial insert of FIG. 14.
Figure 16D:
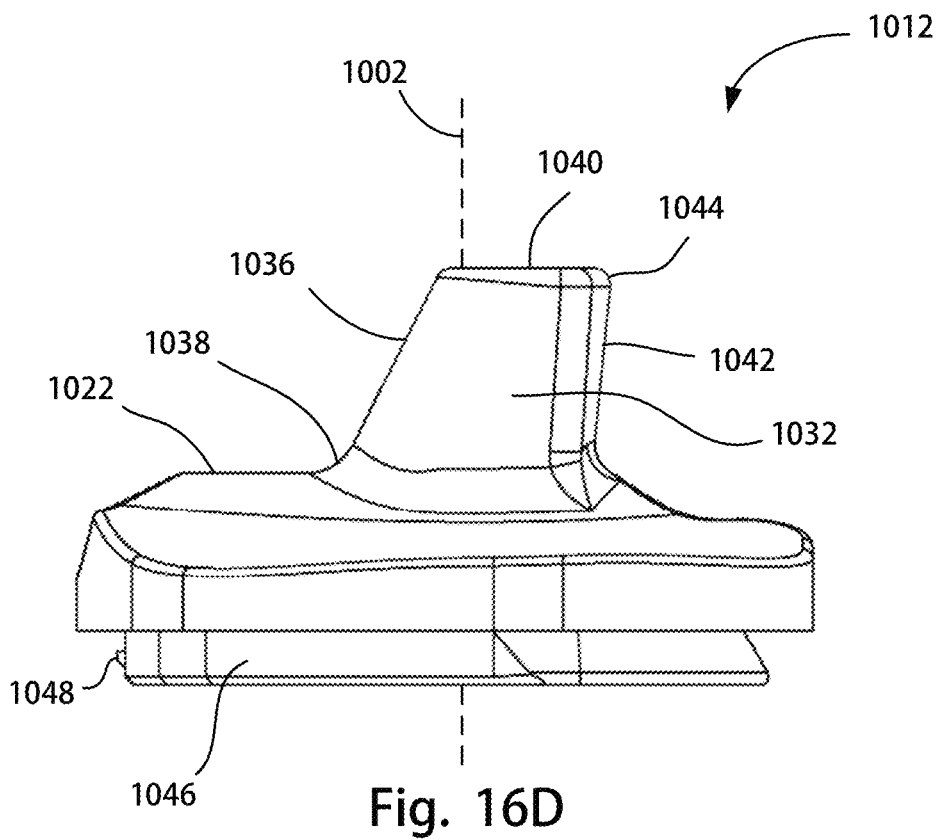
FIG. 16D is a medial side view of the tibial insert of FIG. 14.

Continuing with FIGS. 14-16D, the post 1030 may have an articulation surface 1031 extending around the post 1030 on the medial, posterior, lateral, and anterior aspects of the post 1030. The articulation surface 1031 may include a medial articulation surface 1032, a lateral articulation surface 1034, an anterior post surface 1036, and a posterior articulation surface 1042. The medial and lateral articulation surfaces 1032, 1034 may be non-parallel to one another and taper inward from the post superior end 1040 to the post base 1038 relative to an insert midline vertical axis 1002, as shown in FIGS. 16A and 16B. As shown in FIG. 16A, an angle θ between the vertical axis 1002 and each tapered surface 1032, 1034 may be about 6.5°, in at least one embodiment. Since the post 1030 may be bilaterally symmetrical, the angle θ may be the same on both the medial and lateral sides 1032, 1034 of the post 1030. In other embodiments of the disclosure, angle θ may range from about 6° to 11° degrees. The medial articulation surface 1032 may be continuous with the medial condylar articulation surface 1025, and the lateral articulation surface 1034 may be continuous with the lateral condylar articulation surface 1027. The anterior post surface 1036 may extend between the medial and lateral surfaces 1032, 1034 and may be convexly rounded. The anterior post surface 1036 may also taper outward from the post superior end 1040 to the post base 38 relative to the insert midline vertical axis 1002, as best seen in FIG. 16D. In other embodiments of the PS insert 1012, the anterior post surface 1036 may include less taper, more taper, and/or no taper. A midline medial-lateral axis 1004 and a mid-line anterior-posterior axis 1006 are also shown.

Referring to FIG. 16C, the boundary of the superior end 1040 may define a rounded rim 1044 shaped as a portion of a circle defined by a circular envelope 1047, as seen from a superior perspective. The superior end 1040 and rim 1044 may have a convex protrusion 1041 toward a posterior end of the post 1030 as shown, and may permit passage of the posterior cruciate ligament. The circular superior end 1040 with rim 1044 may provide increased rotational range of motion and surface contact against the femoral component 1014 in comparison to traditional posts with a more square or rectangular shape and no rim. Thus, the rounded superior end 1040 and rim 1044 may allow for greater surface contact with the femoral component 1014 in contrast to the mere point or edge contact that is achieved by traditional posts that do not have these features.

The PS femoral component 1014 depicted in FIGS. 14-15 may include augment fixation apertures 1080, impact driver apertures 1090, a cam element or cam bar 1050, and a box structure 1052 for providing posterior stabilization in place of absent ligaments. The cam bar 1050 may include a cam articulating surface 1051 which may contact the posterior articulation surface 1042 of the post 1030 during flexion. An internal articulation surface 1054 may reside on the inside of the box structure 1052 and may contact the post 1030 during articulation and rotation of the knee joint. The internal articulating surface 1054 may be concavely curved, and may contact the rim 1044 of the post 1030 during axial rotation of the knee joint about the post 1030. The PS femoral component 1014 may further include a medial condyle 1060 having a medial condylar articulation surface 1062, and a lateral condyle 1064 having a lateral condylar articulation surface 1066. The medial and lateral condylar articulation surfaces 1062, 1066 may articulate against the PS insert 1012 medial and lateral articulation surfaces 1025, 1027, respectively. A gap 1068 may be formed between the medial and lateral condyles 1060, 1064, with the cam bar 1050 extending medial-laterally across the gap 1068. The internal articulation surface 1054 may include a medial portion 1070 continuous with a lateral portion 1072. In the embodiment depicted, a fixation post 1074 may protrude superiorly from the PS femoral component 1014. However, in other embodiments of the PS femoral component 1014, the fixation post 1074 may be absent and/or other fixation features such as posts, spikes, pegs, webs, keels, or teeth may be present to affix the PS femoral component 1014 to a prepared femur (not shown).

Figure 17:
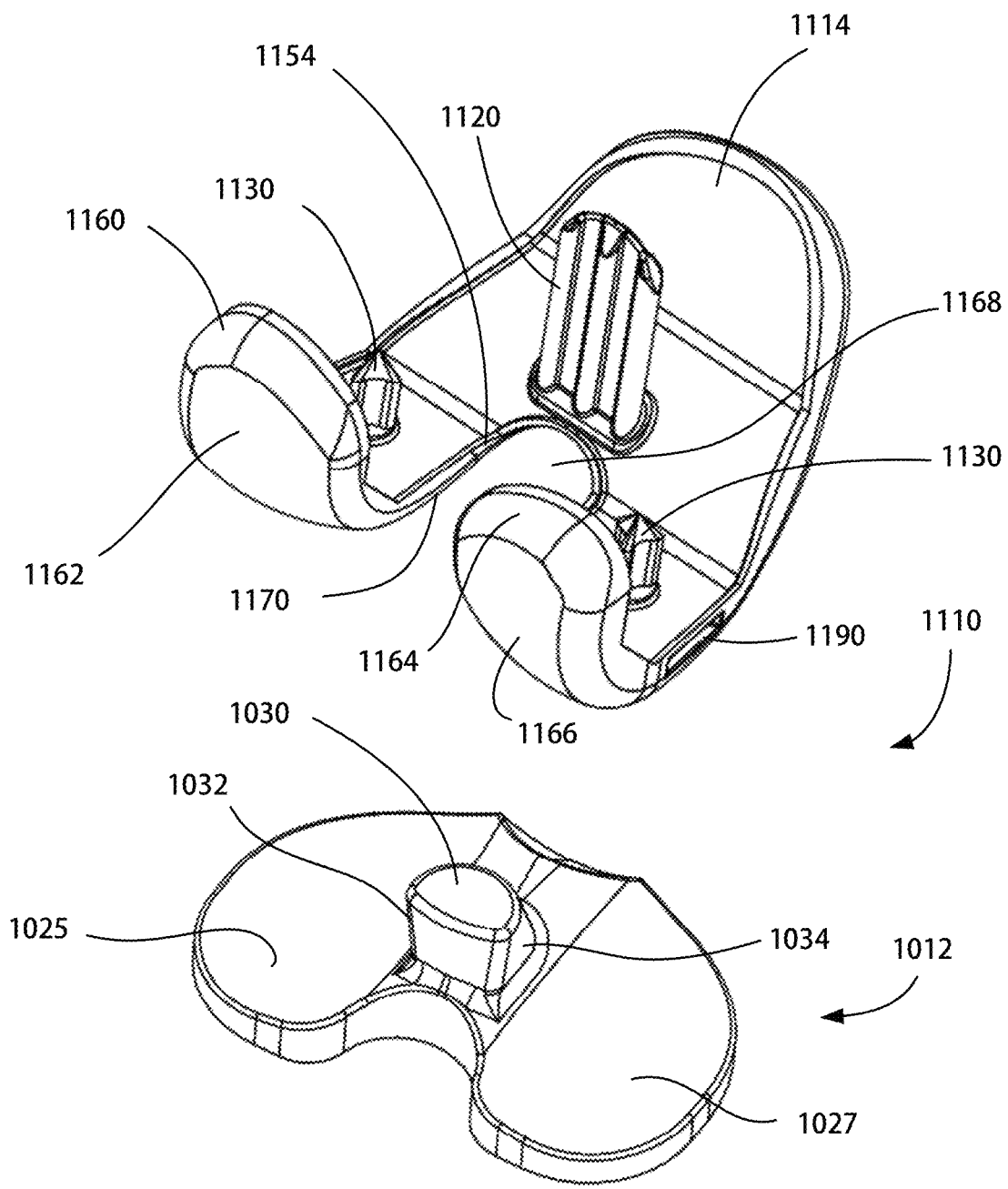
FIG. 17 is an exploded rear view of another assembly of the disclosure, including a cruciate retaining femoral component with a keel and the posterior stabilizing tibial insert of FIG. 14.
Figure 18:
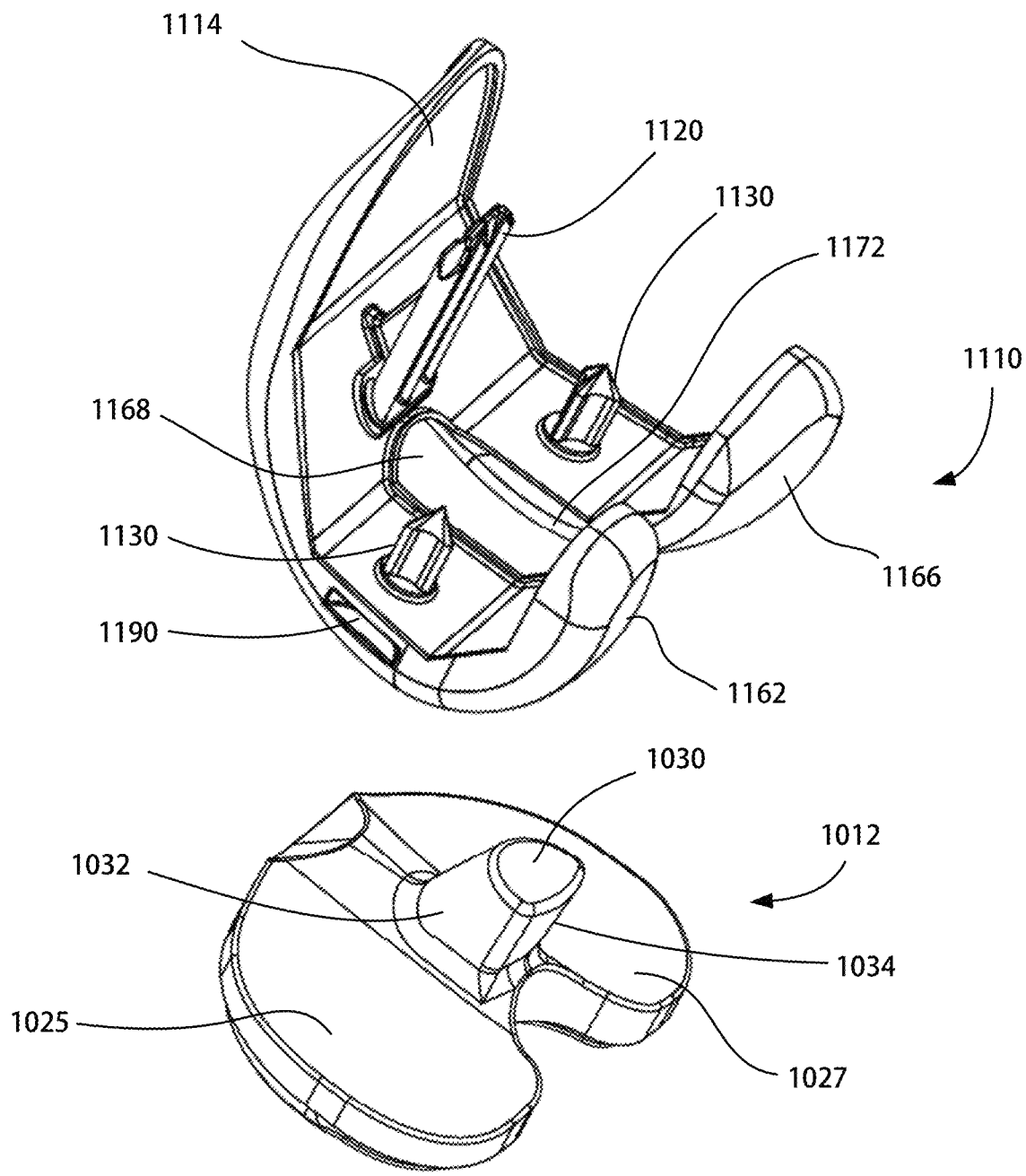
FIG. 18 is another exploded rear view of the assembly of FIG. 17.

Referring to FIGS. 17 and 18, another assembly 1110 embodiment of the disclosure may include the PS insert 1012 of FIGS. 14-16D coupled with a cruciate retaining femoral component 1114 (or "CR femoral component"). The CR femoral component 1114 may include a keel 1120, fixation members 1130, impact driver apertures 1190, and medial and lateral condyles 1160, 1164 with a gap 1168 formed between the condyles 1160, 1164. As a CR femoral component 1114, no cam bar or box may be present. The condyles 1160, 1164 may include medial and lateral condylar articulation surfaces 1162, 1166, and an internal articulation surface 1154 with medial and lateral portions 1170, 1172.

The tapered sides 1032, 1034 of the post 1030 may permit natural articulation of the CR femoral component 1114 with the PS insert 1012, which may not be achievable if the post 1030 were not tapered. For example, if the post 1030 had straight sides instead of tapered sides, the wider width of the post 1030 at the base of the post 1030 may interfere with the internal articulating surfaces 1170, 1172 of the condyles 1160, 1164. When the PS femoral component 1014 is coupled with the PS insert 1012 to form assembly 1010, as in FIGS. 14 and 15, the circular shape of the post superior end 1040 in combination with the tapered medial and lateral surfaces 1032, 1034 of the post 1030, may permit the PS femoral component 1014 to articulate relative to the PS insert 1012 in the manner of a posterior stabilized femoral component. However, when the PS insert 1012 is paired and implanted with the CR femoral component 1114, the resultant assembly 1110 may provide the native articulation and rotation of a cruciate retaining implant.

Figure 19:
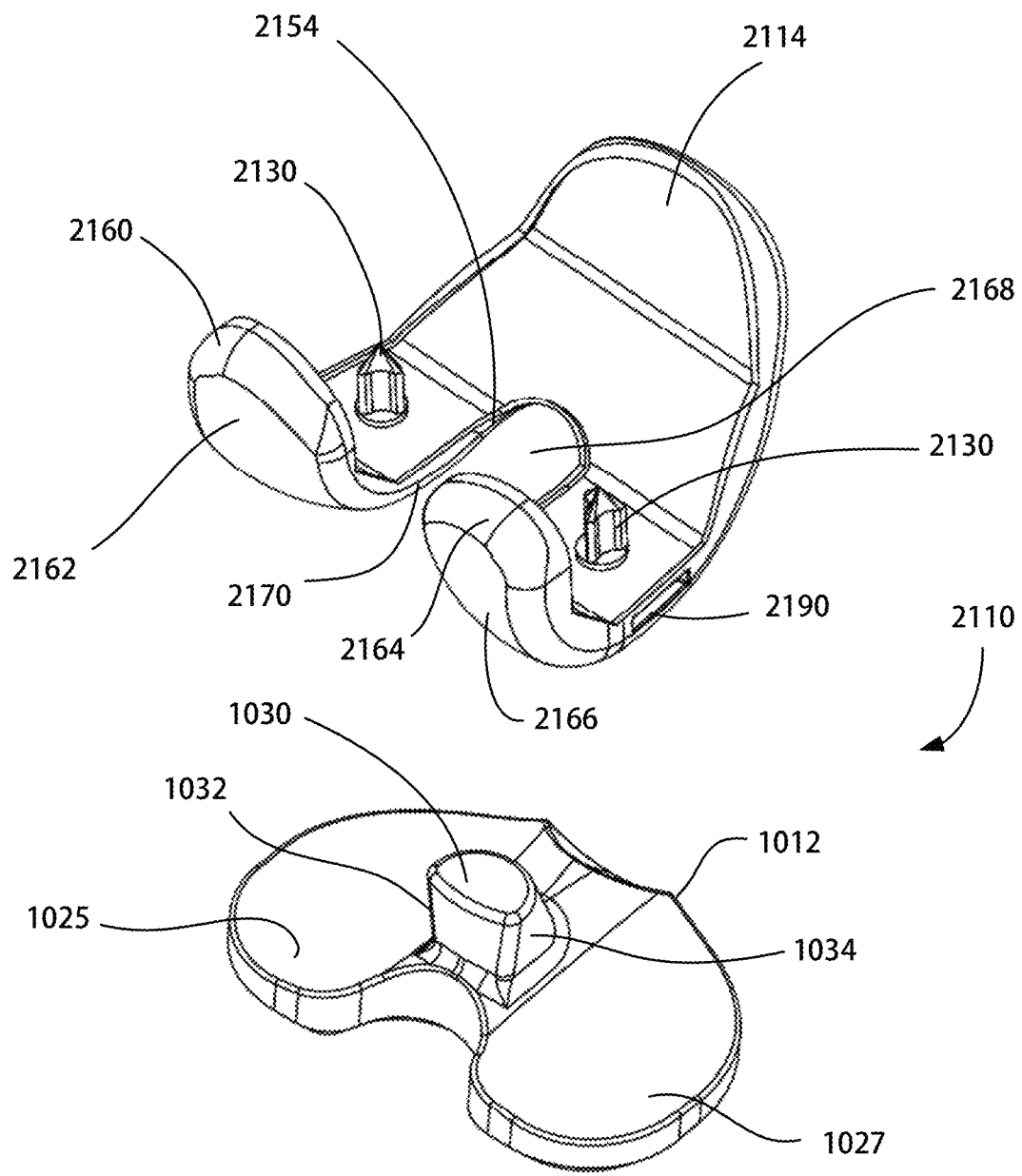
FIG. 19 is an exploded rear view of another assembly of the disclosure, including a cruciate retaining femoral component without a keel and the posterior stabilizing tibial insert of FIG. 14.
Figure 20:
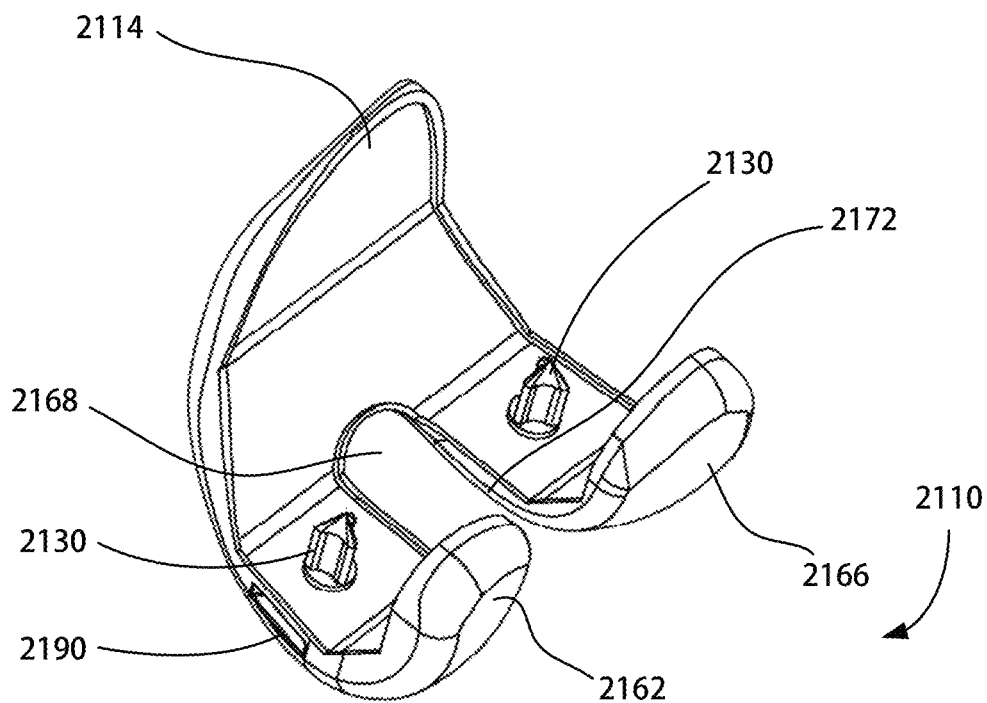
FIG. 20 is another exploded rear view of the assembly of FIG. 19.
Figure 20:
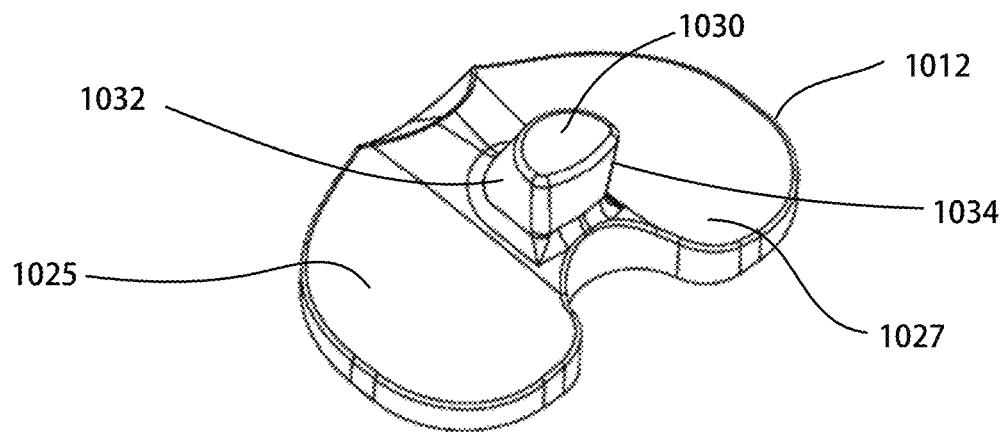
Figure 21A:
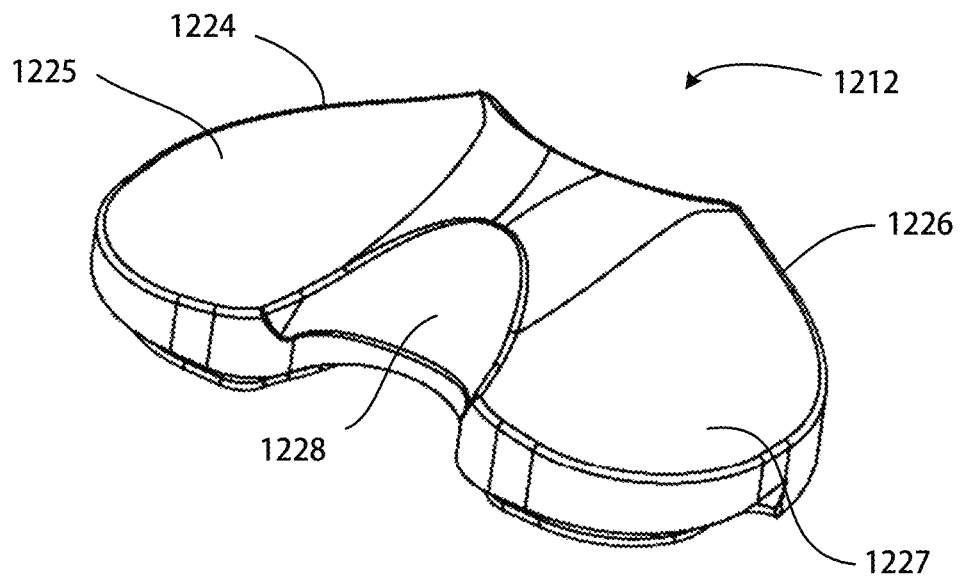
FIG. 21A is a perspective rear view of another tibial insert of the disclosure.
Figure 21B:
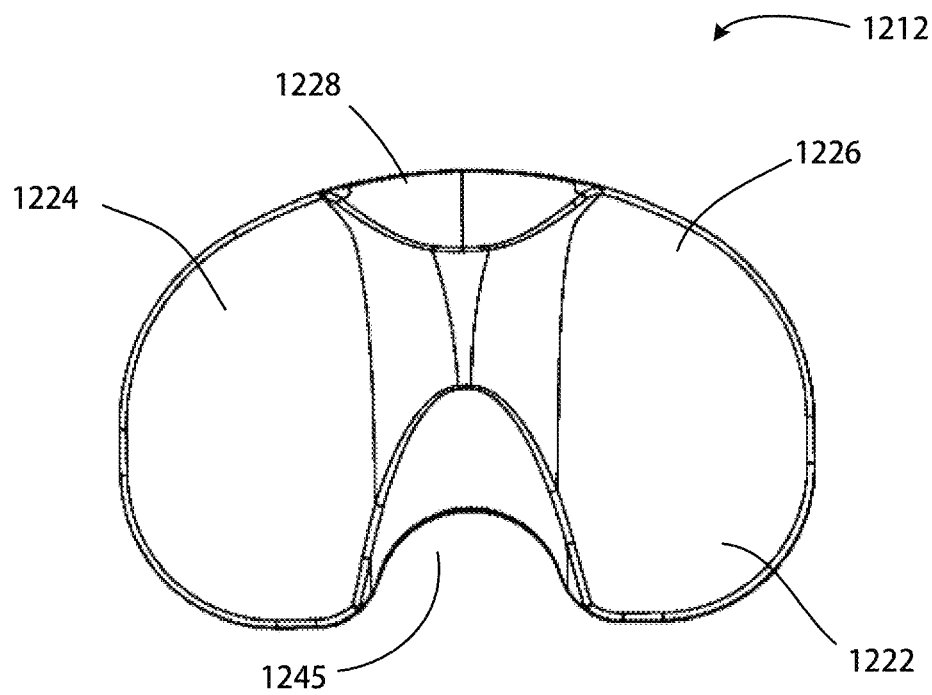
FIG. 21B is a top view of the tibial insert of FIG. 21A.
Figure 21C:
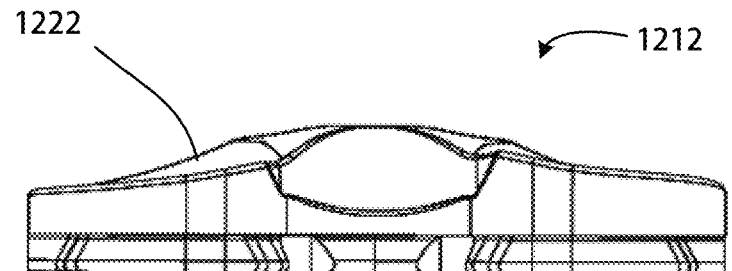
FIG. 21C is a posterior view of the tibial insert of FIG. 21A.
Figure 21D:
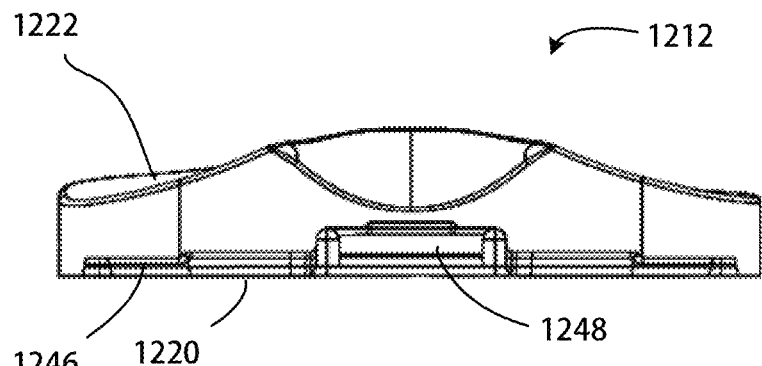
FIG. 21D is an anterior view of the tibial insert of FIG. 21A.
Figure 21E:
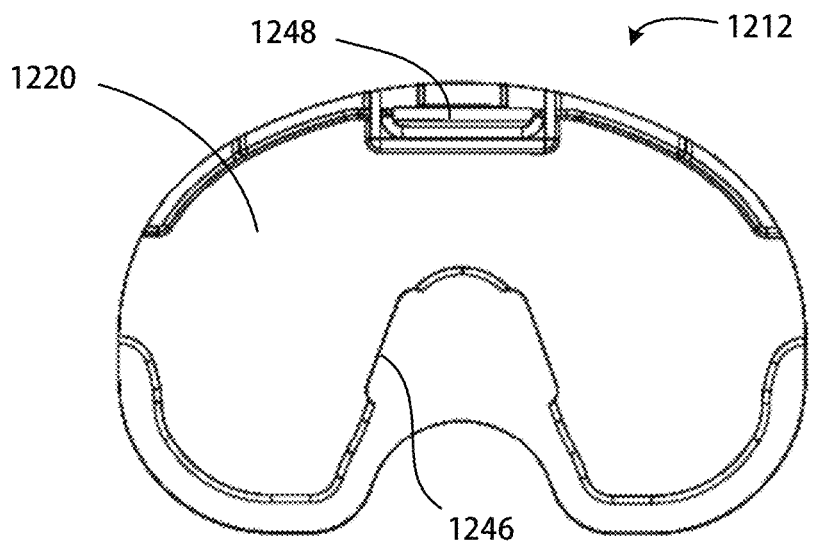
FIG. 21E is a bottom view of the tibial insert of FIG. 21A.

Referring to FIGS. 19 and 20, another assembly 2110 embodiment of the disclosure may include the PS insert 1012 of FIGS. 14-16D coupled with a cruciate retaining femoral component 2114 (or "CR femoral component"). The CR femoral component 2114 may not include a keel, as opposed to the CR femoral component 1114 shown in FIGS. 17 and 18, and the CR femoral component 2114 may be configured for cemented and/or cementless fixation to a femoral bone. The CR femoral component 2114 may include fixation members 2130, impact driver apertures 2190, and medial and lateral condyles 2160, 2164 with a gap 2168 formed between the condyles 2160, 2164. As a CR femoral component 2114, no cam bar or box may be present. The condyles 2160, 2164 may include medial and lateral condylar articulation surfaces 2162, 2166, and an internal articulation surface 2154 with medial and lateral portions 2170, 2172.

The tapered sides 1032, 1034 of the post 1030 may permit natural articulation of the CR femoral component 2114 with the PS insert 1012, which may not be achievable if the post 1030 were not tapered. For example, if the post 1030 had straight sides instead of tapered sides, the wider width of the post 1030 at the base 1038 of the post 1030 may interfere with the medial and lateral portions 2170, 2172 of the internal articulation surface 2154 of the condyles 2160, 2164. When the PS femoral component 1014 is coupled with the PS insert 1012 to form assembly 1010, as in FIGS. 14 and 15, the circular shape of the post superior end 1040 in combination with the tapered medial and lateral surfaces 1032, 1034 of the post 1030, may permit the PS femoral component 1014 to articulate relative to the PS insert 1012 in the manner of a posterior stabilized femoral component. However, when the PS insert 1012 is paired and implanted with the CR femoral component 2114, the resultant assembly 2110 may provide the native articulation and rotation of a cruciate retaining implant.

Referring to FIGS. 21A-21E, an alternative embodiment of a tibial insert 1212 is shown. The tibial insert 1212 may be referred to as a cruciate retaining tibial insert 1212 (or "CR insert"). In a system of the disclosure, the CR insert 1212 may be implanted with the CR femoral components 114, 1114, 2114 and a tibial baseplate component (not shown) to form a cruciate retaining knee prosthesis system. The CR insert 1212 may include a fixation side 1220, which may be an inferior side, opposite an articulation side 1222, which may be a superior side. The articulation side 1222 may include a medial articulation portion 1224 having a medial condylar articulation surface 1225 and a lateral articulation portion 1226 having a lateral condylar articulation surface 1227. A central portion 1228 may separate the medial articulation portion 1224 from the lateral articulation portion 1226. A recess 1245 may be formed posterior to the central portion 1228, between the medial and lateral articulation portions 1224, 1226, and may provide room for a posterior cruciate ligament. The CR insert 1212 may further include an insert base 1246 and an engagement feature 1248 for engagement with a tibial baseplate component.

The CR insert 1212 may be coupled with CR femoral components 114, 1114, 2114 to form a cruciate retaining assembly. This cruciate retaining assembly may be implanted with a suitable tibial baseplate as a complete cruciate retaining knee prosthesis. The CR insert 1212 may also be coupled with PS femoral components 14, 1014 to form a posterior stabilizing assembly and implanted with a suitable tibial baseplate as a complete posterior stabilizing knee prosthesis.

Figure 22A:
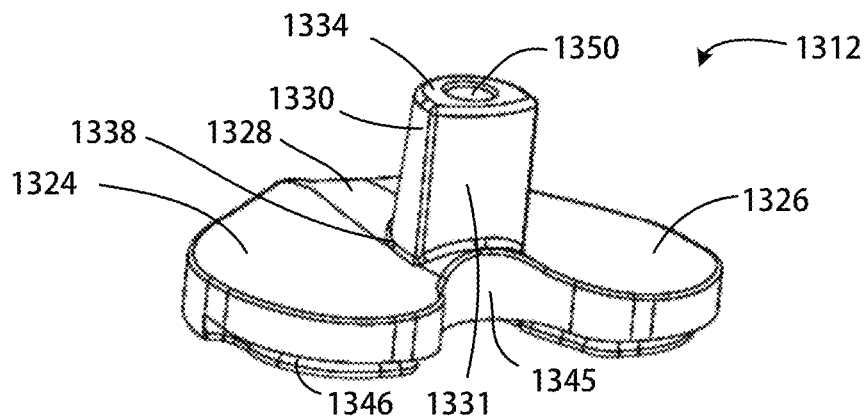
FIG. 22A is a perspective rear view of another tibial insert of the disclosure.
Figure 22B:
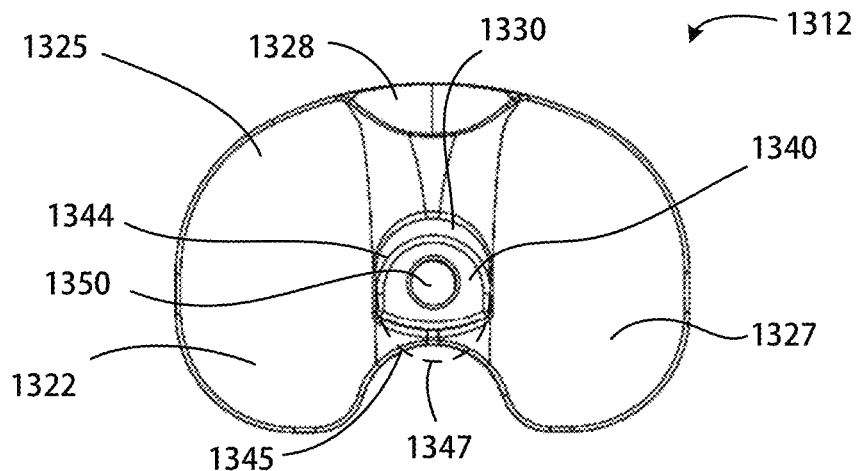
FIG. 22B is a top view of the tibial insert of FIG. 22A.
Figure 22C:
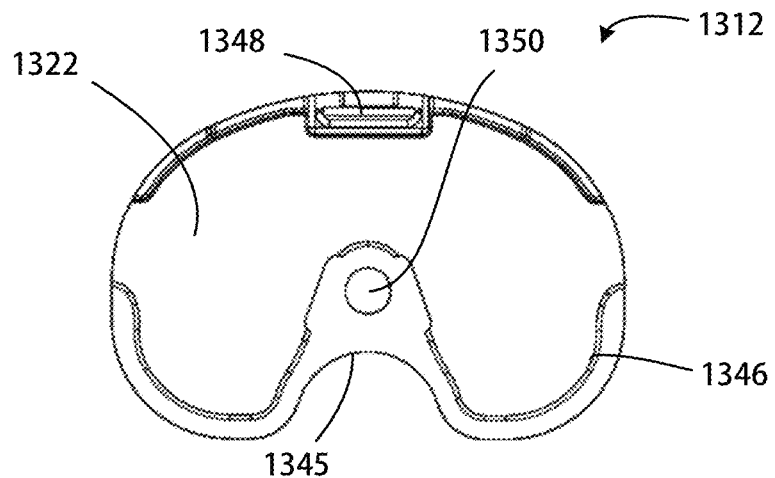
FIG. 22C is a bottom view of the tibial insert of FIG. 22A.
Figure 22D:
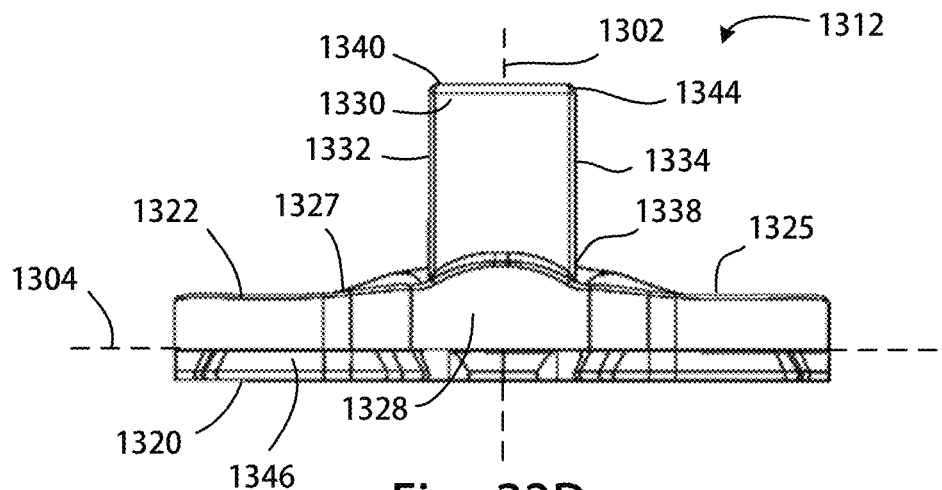
FIG. 22D is a posterior view of the tibial insert of FIG. 22A.
Figure 22E:
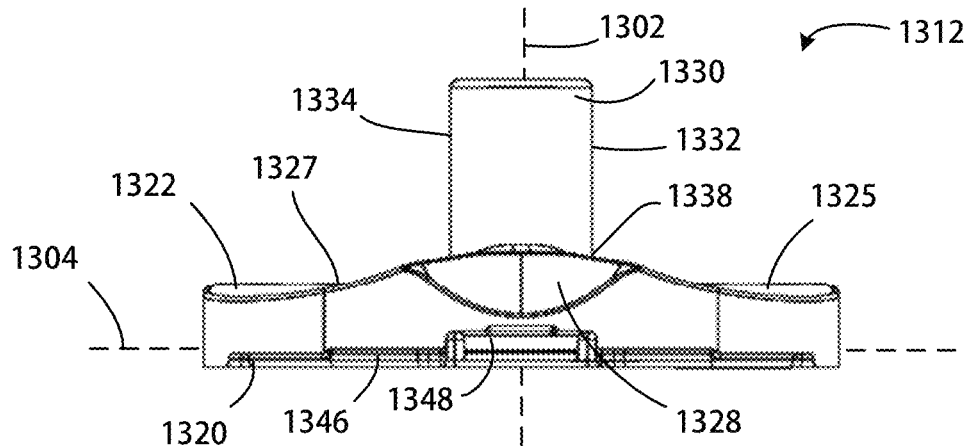
FIG. 22E is an anterior view of the tibial insert of FIG. 22A.

Referring to FIGS. 22A-22F, another alternative embodiment of a tibial insert 1312 is shown. The tibial insert 1312 may be referred to as a constrained condylar knee (CCK) tibial insert 1312 (or "CCK insert"). The CCK insert 1312 may include a fixation side 1320, which may be an inferior side, opposite an articulation side 1322, which may be a superior side. The articulation side 1322 may include a medial articulation portion 1324 having a medial condylar articulation surface 1325 and a lateral articulation portion 1326 having a lateral condylar articulation surface 1327. A central portion 1328 may separate the medial articulation portion 1324 from the lateral articulation portion 1326. A post 1330 may protrude superiorly from the central portion 1328, and extend from a post base 1338 to a top, or post superior end 1340. From the anterior perspective, as shown in FIG. 22E, and the posterior perspective, as shown in FIG. 22D, the post 1330 may have its maximum medial-lateral or horizontal width at the post superior end 1340 of the post 1330, and its minimum medial-lateral or horizontal width at the post base 1338 of the post 1330. The post 1330 may be bilaterally symmetrical from the anterior and posterior perspectives. The CCK insert 1312 may further include a posterior recess 1345, an insert base 1346, and an engagement feature 1348 for engagement with a tibial tray (not shown). An opening 1350 may be present in the superior surface of the post 1330.

Figure 22F:
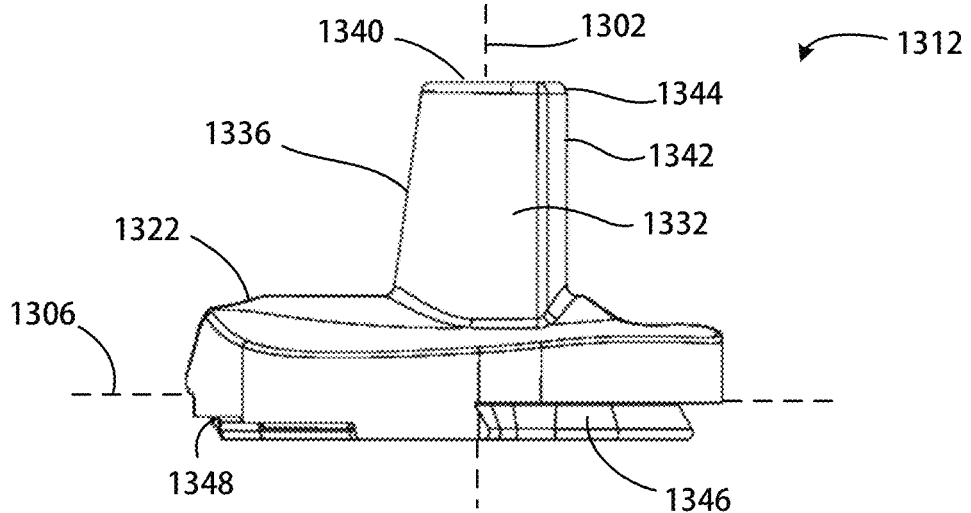
FIG. 22F is a medial side view of the tibial insert of FIG. 22A.

The post 1330 may have an articulation surface 1331 extending around the post 1330 on the medial, posterior, lateral, and anterior aspects of the post 1330. The articulation surface 1331 may include a medial articulation surface 1332, a lateral articulation surface 1334, an anterior post surface 1336, and a posterior articulation surface 1342. The medial and lateral articulation surfaces 1332, 1334 may taper slightly inward from the post superior end 1340 to the post base 1338 of the post 1330 relative to an insert midline vertical axis 1302. However, some embodiments of CCK insert 1312 may include less taper, more taper, and/or no taper of the medial and lateral articulation surfaces 1332, 1334. The medial articulation surface 1332 may be continuous with the medial condylar articulation surface 1325, and the lateral articulation surface 1334 may be continuous with the lateral condylar articulation surface 1327. The anterior post surface 1336 may extend between the medial and lateral articulation surfaces 1332, 1334 and may be convexly rounded. The anterior post surface 1336 may taper outward from the post superior end 1340 to the post base 1338 relative to the midline axis 1302, as best seen in FIG. 22F. In other embodiments of the CCK insert 1312, the anterior post surface 1336 may include less taper, more taper, and/or no taper. The post 1330 of the CCK insert 1312 may be wider and bigger in diameter than the post 30 of PS insert 12, for example to provide increased stability in the case of removal of the collateral ligaments. A midline medial-lateral axis 1304 and a mid-line anterior-posterior axis 1306 are also shown in FIGS. 22D through 22F.

Referring to FIG. 22B, the boundary of the post superior end 1340 may define a rounded rim 1344 shaped as a portion of a circle, from a superior perspective, and may have a convex protrusion toward a posterior end of the post 1330. The post superior end 1340 and rim 1344 may be semi-circular as shown, however the rim 1344 may define a circular envelope 1347. The post superior end 1340 may be circular and the rim 1344 may provide increased surface contact and rotational range of motion when coupled and implanted with the PS femoral components disclosed herein in comparison to traditionally shaped posts with a more square or rectangular shaped post. Thus, the rounded post superior end 1340 and rim 1344 may allow for greater surface contact with the femoral components 14, 1014 in contrast to the mere point or edge contact that is achieved by traditional posts that do not include these features.

The CCK insert 1312 may be coupled with the PS femoral components 14, 1014 to form a constrained condylar knee assembly, and this assembly may be implanted with a suitable tibial baseplate as a constrained condylar knee prosthesis. The CCK insert 1312 may also be coupled with any of the CR femoral components disclosed herein and implanted with a suitable tibial baseplate. Thus, all of the tibial inserts disclosed herein are interchangeable with all of the CR and PS femoral components disclosed herein.

Any of the tibial inserts, CR femoral components, and/or PS femoral components disclosed herein may be grouped together in any number or combination as one or more modular knee replacement systems or kits. A particular kit may include a CR femoral component, a PS insert, and a CR insert. Yet another particular kit may include a PS femoral component, a PS insert, a CR insert, and a CCK insert. Suitable tibial baseplate components may also be included with any kit. Moreover, any of the tibial inserts disclosed herein may be formed of vitamin E polyethylene, highly cross linked polyethylene, ultra-high molecular weight polyethylene (UHMWPE), and/or the like.

In an example method of the disclosure, a patient may initially experience compromise of the anterior cruciate ligament. The ACL may be removed, and a CR type prosthesis may be implanted, including a CR femoral component, a CR insert, and a tibial baseplate component. Later, the same patient may experience compromise of the PCL and may need additional stabilization of the knee joint. The PCL may be removed, the CR tibial insert may be removed, and a PS tibial insert of the disclosure may be inserted between the originally implanted CR femoral component and the tibial baseplate component, thus providing additional stability for the missing PCL. Even later, the same patient may experience instability of the collateral ligaments. The PS tibial insert may be removed, and the CCK tibial insert of the disclosure may be inserted between the originally implanted CR femoral component and the tibial baseplate component. Thus, the patient may progress from a CR knee prosthesis, to a PS knee prosthesis, and finally to a CCK knee prosthesis without requiring replacement of the originally implanted femoral and/or tibial baseplate components. The interchangeability of the inserts permits replacement of only the tibial insert component in order to provide increasing levels of support and stability to the knee joint.

In another example method of the disclosure, a patient may initially experience compromise of both the ACL and the PCL. These ligaments may be removed, and a PS type prosthesis may be implanted, including a PS femoral component, a PS insert, and a tibial baseplate component. Later, the same patient may experience instability of the collateral ligaments. The PS insert may be removed, and a CCK insert may be inserted between the originally implanted PS femoral component and the tibial baseplate component. Thus, the patient may progress from a PS knee prosthesis to a CCK knee prosthesis without requiring replacement of the originally implanted PS femoral component and tibial baseplate component.

Figure 23A:
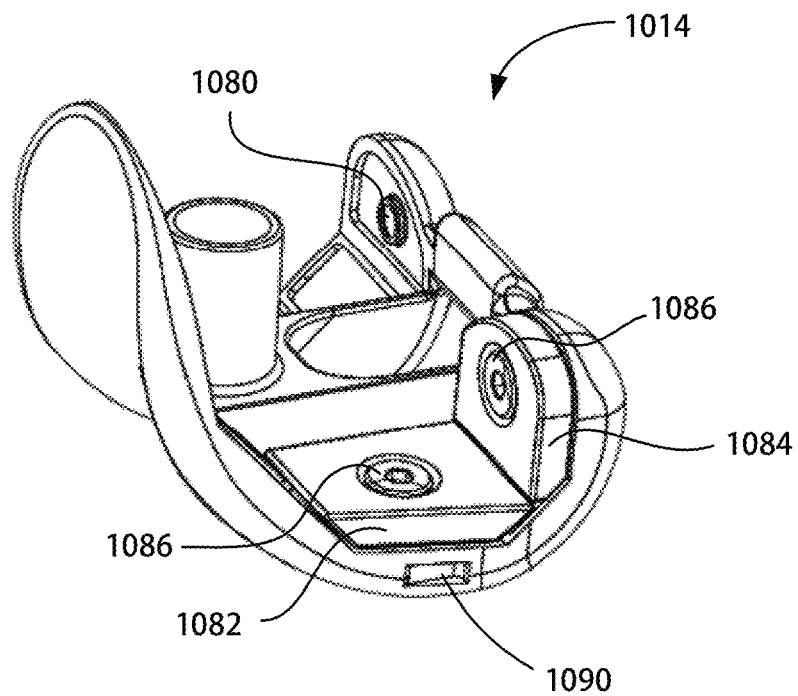
FIG. 23A is a perspective front view of the femoral component of FIG. 14 coupled to one or more augments of the present disclosure.
Figure 23B:
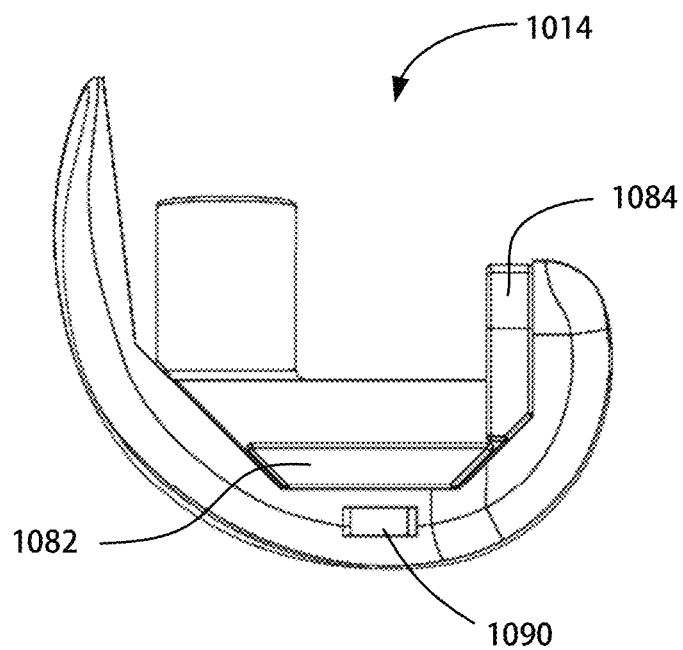
FIG. 23B is a medial side view of the femoral component of FIG. 23A.

Referring now to FIGS. 23A-B, FIG. 23A is a perspective front view of the femoral component 1014 of FIG. 14 coupled to one or more augments 1082, 1084 of the present disclosure and FIG. 23B is a medial side view of the femoral component 1014 of FIG. 23A. As briefly mentioned above with reference to FIGS. 14 and 15, the femoral component 1014 may include augment fixation apertures 1080 that may be configured to secure the one or more augments 1082, 1084 to the femoral component 1014, as well as impact driver apertures 1090 configured to receive a femoral component impact driver tool (not shown) to allow a surgeon to press fit the femoral component 1014 to the end of a prepared femur. The augments 1082, 1084 may be secured to the femoral component 1014 with fixation members 1086 and the augments 1082, 1084 may generally act to replace missing and/or compromised femoral bone and allow the femoral component 1014 to be adequately secured to a femoral bone under such conditions.

Figure 24A:
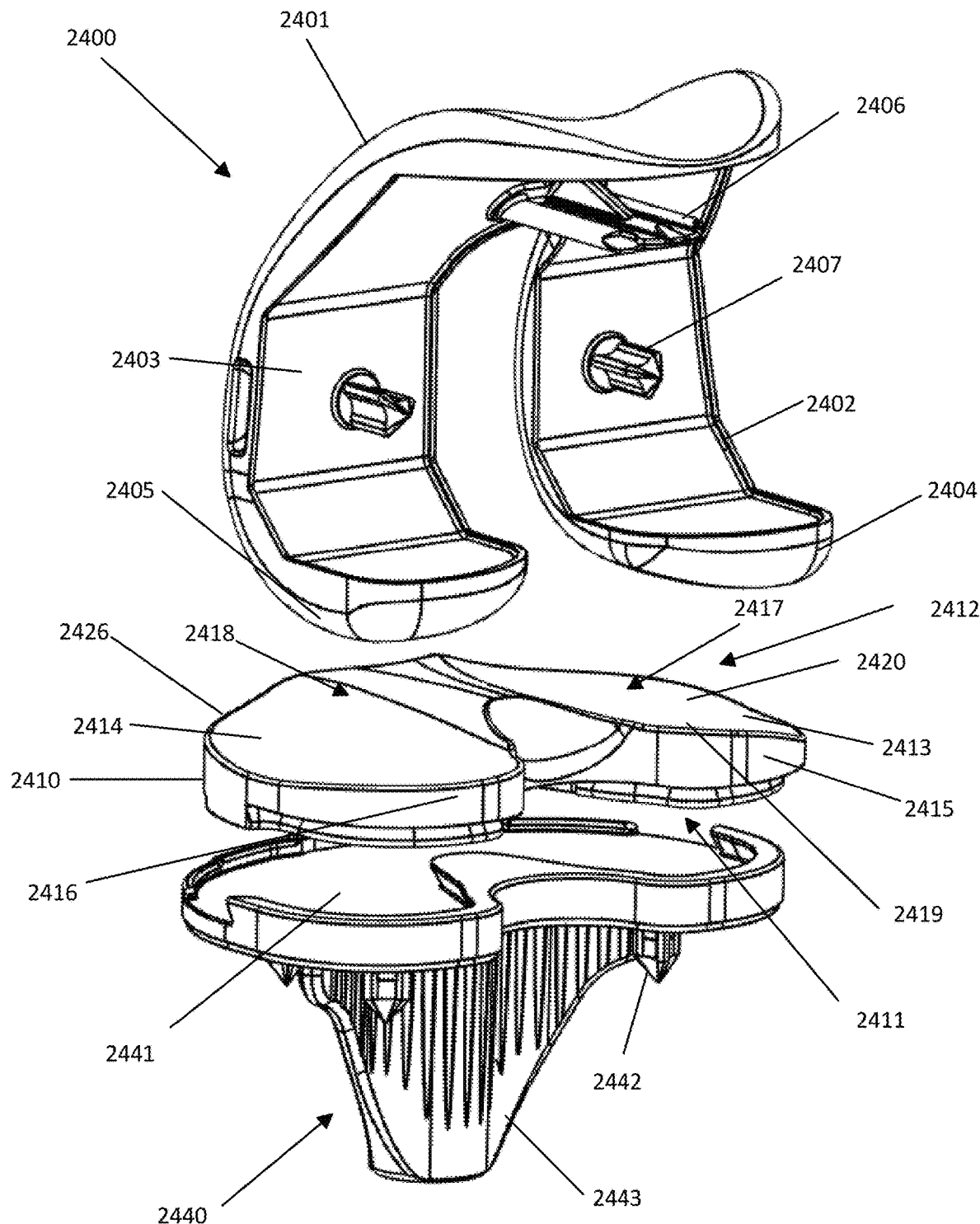
FIG. 24A is a posterior exploded view of a knee prosthesis assembly with an asymmetric tibial insert.

Referring to FIGS. 24A to 24E, an assembly 2400 for an implantable knee prosthesis is shown, according to another embodiment. Assembly 2400 may include a femoral component 2401, an insert 2410, and a tibial component 2440. FIG. 24A is an exploded view of the assembly 2400 approaching the assembly 2400 from a posterior-lateral side, in reference to the anatomy of a patient. The assembly 2400 is generally asymmetric across the medial and lateral sides, in other words the left side is asymmetric compared to the right side. With regard to the assembly 2400, the term "medial" refers to being proximal to the sagittal plane of a patient's anatomy, toward the centerline of the patient. The term "lateral" refers to being distal to the sagittal plane, toward the outside of the patient's anatomy. In FIGS. 24 to 31, a left knee is shown, but the same features will be present in an assembly 2400 configured for a right knee in a mirrored orientation. In either a left or right configuration, medial will be proximal to the sagittal plane, or on the inside of the knee, and lateral is distal from the sagittal plane, or outside of the knee.

The femoral component 2401 may be posterior stabilizing or cruciate retaining. In FIG. 24A, the femoral component 2401, the tibial insert 2410, and the tibial component 2440 are shown in flexion. The femoral component 2401 may include medial condyle 2402 and lateral condyle 2403, similar to femoral component 114 in FIG. 9. The medial 2402 and lateral 2403 condyles may include medial condylar articulation surface 2404 and lateral condylar articulation surface 2405. The femoral component 2401 may include elements to secure the femoral component 2401 in the femur of the patient. For example, the femoral component 2401 may include at least one keel 2406 and at least one post 2407 that penetrate the bone of the associated femur (not shown) to secure the femoral component 2401 to the femur. The at least one post 2407 may be placed on the femoral side of the medial condyle 2402 and/or the lateral condyle 2403. The femoral component 2401 may include surface texturing on the bone-facing side to encourage bone in-growth and securement.

The tibial component 2440 may be configured to be secured to the tibia of the patient. The tibial component 2440 may include an insert seat 2441 configured for the placement and securement of the insert 2410, with one or more tibial posts 2442, which may be inserted and secured into a patient's tibia. The tibial component 2440 may further have a base 2443, which may also be designed to penetrate the tibial plateau, and may receive a separate keel (not shown) that penetrates more deeply into the intramedullary canal of the tibia.

FIG. 24A shows the exploded assembly 2400 from a lateral side configured for placement in a left knee and shown in approximately 90 degree extension, or "flexion." While the tibial component 2440 and the femoral component 2401 may be medially and laterally symmetric across an anterior-posterior plane, the insert 2410 may be medially-laterally asymmetric. The insert 2410 may include a fixation side or base 2411 configured to mate or engage with the insert seat 2441 of the tibial component 2440. The base 2411 may have features complementary to features on the insert seat 2441. The complementary features may allow for a removable fit for the insert 2410. The removable fit may allow for a modular assembly 2400, benefitting the surgeon and the patient.

In some embodiments, the tibial component 2440 and the femoral component 2401 may be symmetric, as mentioned previously, enabling them to be used for either left or right knee replacements. Only the insert 2410 may be specific to one side or the other. An assembly for either left or right knee arthroplasty may include only one femoral component 2401, one tibial component 2440, and two (e.g., left and right) inserts 2410. This may greatly reduce the inventory requirements for the system.

Opposite the base 2411, the insert 2410 has a superior articulation side 2412 configured for engagement with the medial 2402 and lateral 2403 condyles on the femoral component 2401. The superior articulation side 2412 may include a medial articulation side 2413 and a lateral articulation side 2414. The medial articulation side 2413 may include a medial articulation surface 2420 for direct engagement with the medial condylar articulation surface 2404. The lateral articulation side 2414 may include a lateral articulation surface 2421 for direct engagement with the lateral condylar articulation surface 2405. The medial condyle articulation surface 2404 may engage with the medial articulation surface 2420 at a medial dwell point 2435. The lateral condyle articulation surface 2405 may engage with the lateral articulation surface 2421 at a lateral dwell point 2436 (shown in subsequent figures). The medial articulation surface 2420 may include a medial ramp 2019, which may have no counterpart on the lateral articulation surface 2421 and may create at least part of the asymmetry between the medial articulation side 2413 and the lateral articulation side 2414.

Figure 24B:
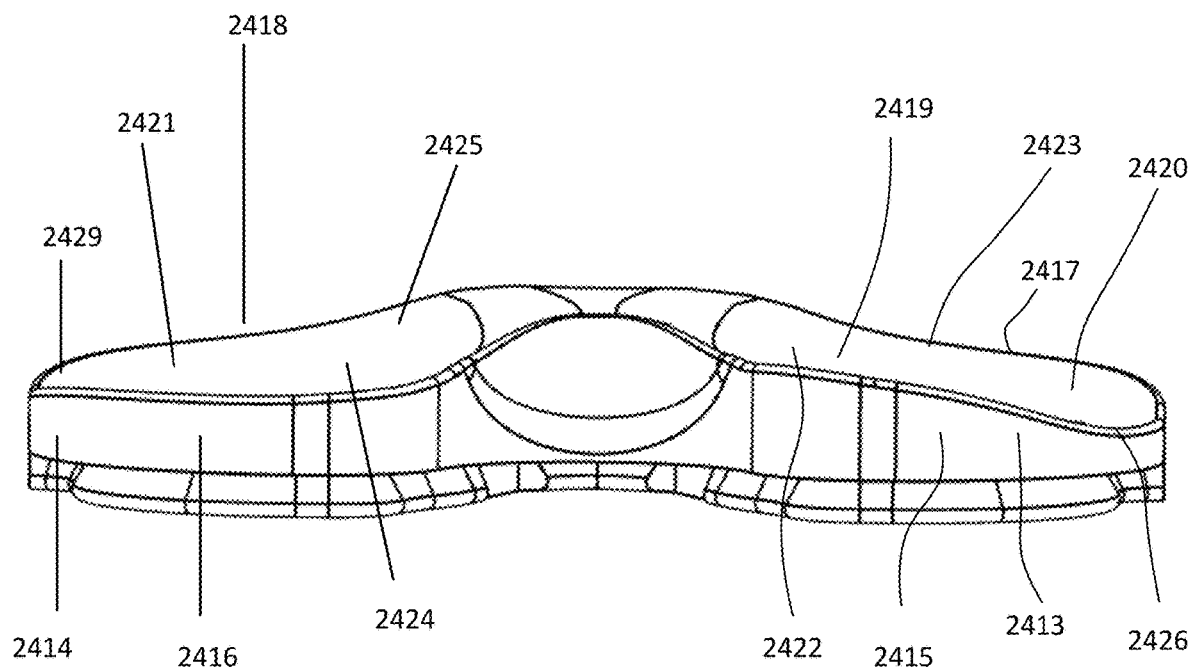
FIG. 24B is a posterior view of the asymmetric tibial insert of FIG. 24A.
Figure 24C:
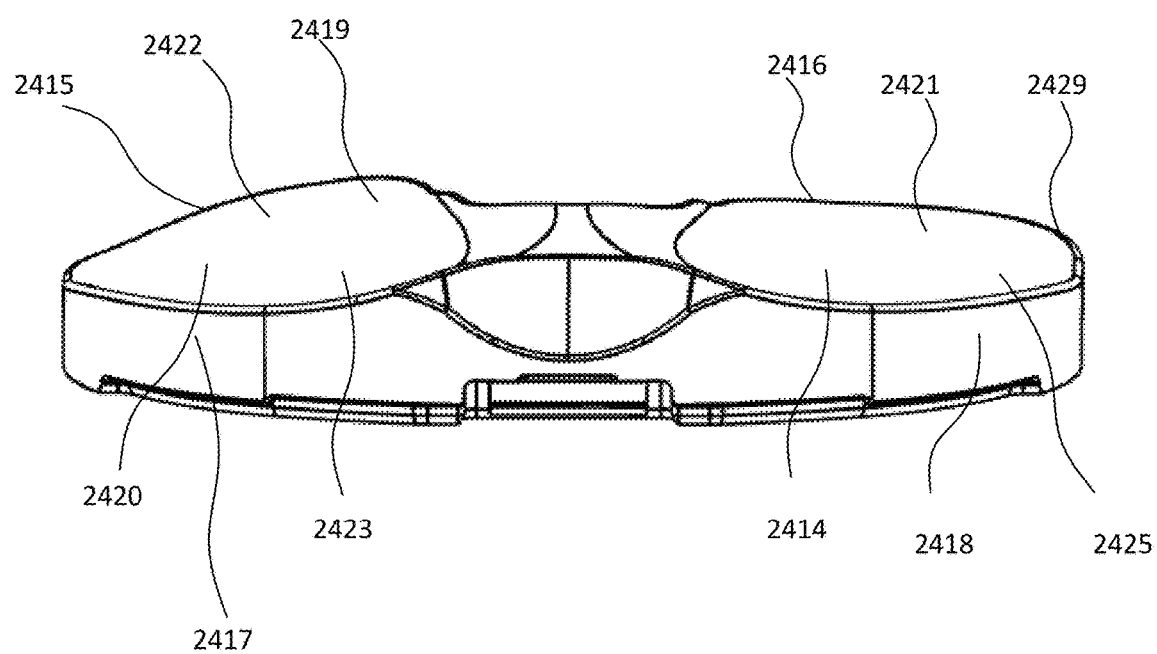
FIG. 24C is an anterior view of the asymmetric tibial insert of FIG. 24A.
Figure 24D:
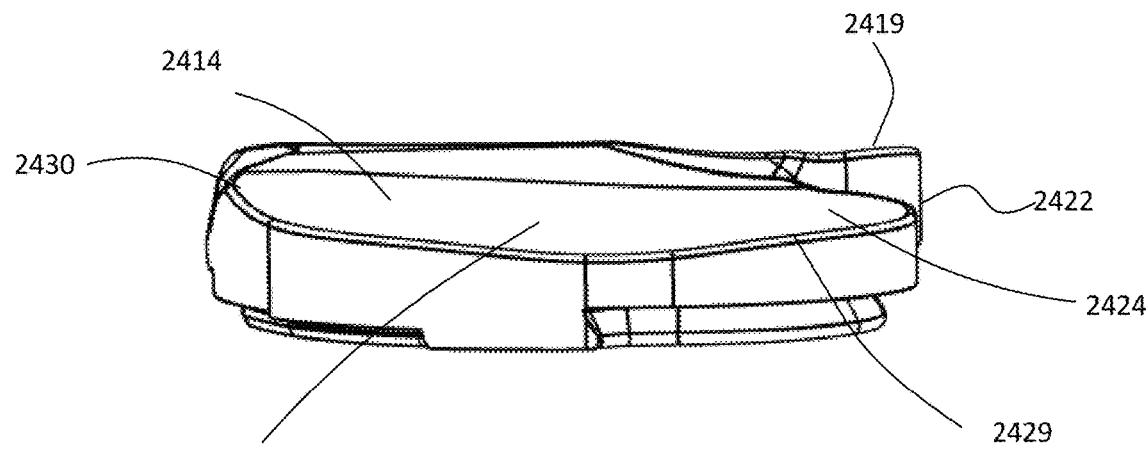
FIG. 24D is a side view of the lateral side of the asymmetric tibial insert of FIG. 24A.

FIGS. 24B-24D show details of the shape of the insert 2410. FIG. 24B is a posterior view of the insert 2410. FIG. 24C is an anterior view of the insert 2410. The lateral articulation side 2414 may include a lateral posterior side 2416 and a lateral anterior side 2418. The lateral articulation surface 2421 may include a lateral posterior section 2424 and a lateral anterior section 2425 surrounded by a lateral perimeter 2429. The medial articulation side 2413 may include a medial posterior side 2415 and a medial anterior side 2417. The medial articulation surface 2420 may include a medial posterior section 2422 and a medial anterior section 2423 surrounded by a medial perimeter 2426.

Figure 24E:
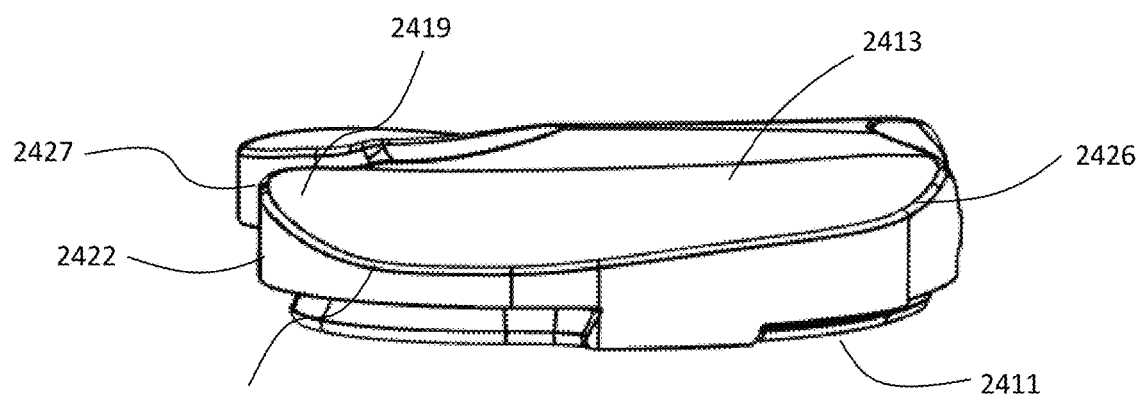
FIG. 24E is a side view of the medial side of the asymmetric tibial insert of FIG. 24A.
Figure 24F:
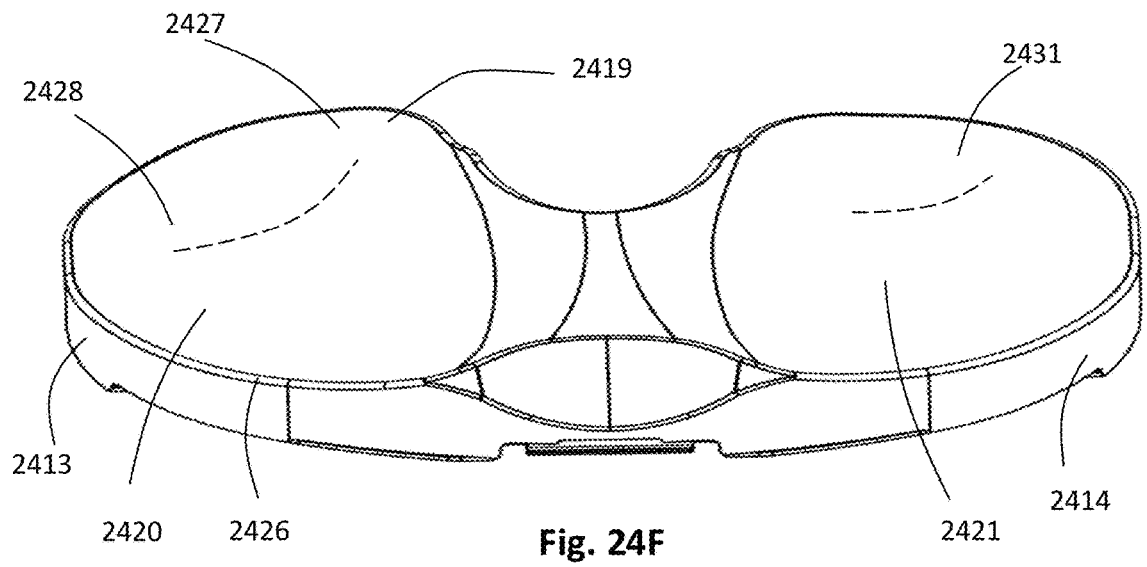
FIG. 24F is a perspective view of the asymmetric tibial insert of FIG. 24A.
Figure 25A:
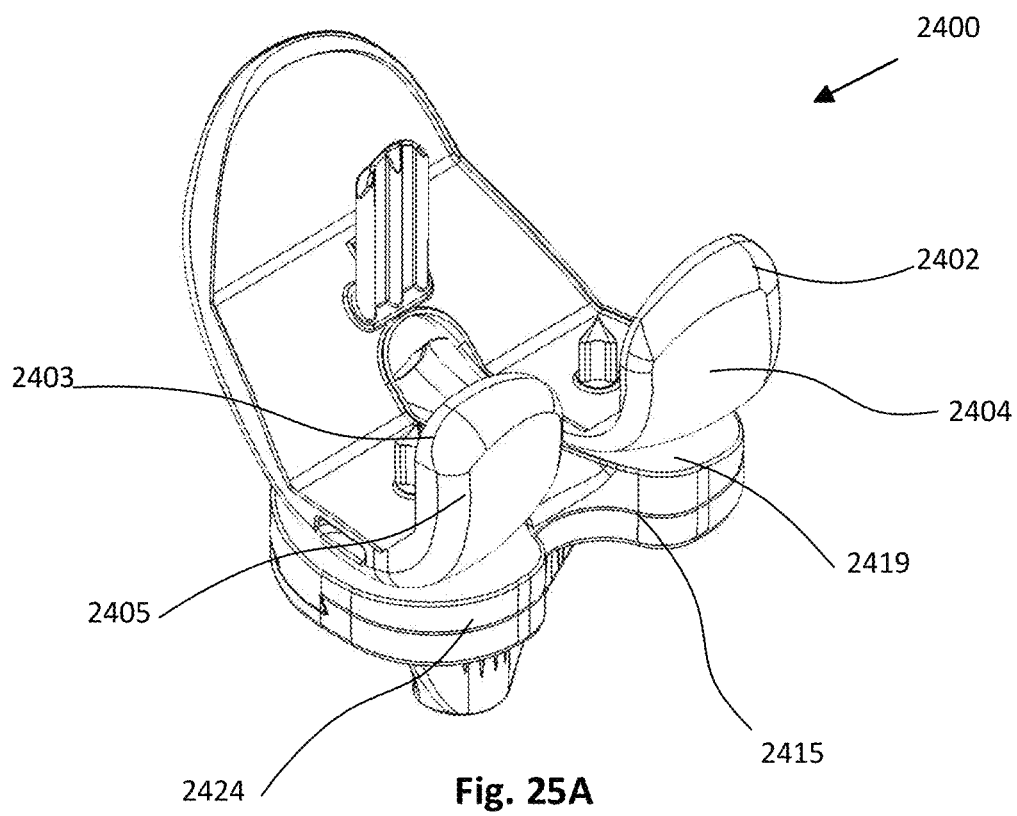
FIG. 25A is perspective posterior view of a knee prosthesis assembly in 0 degree flexion.
Figure 25B:
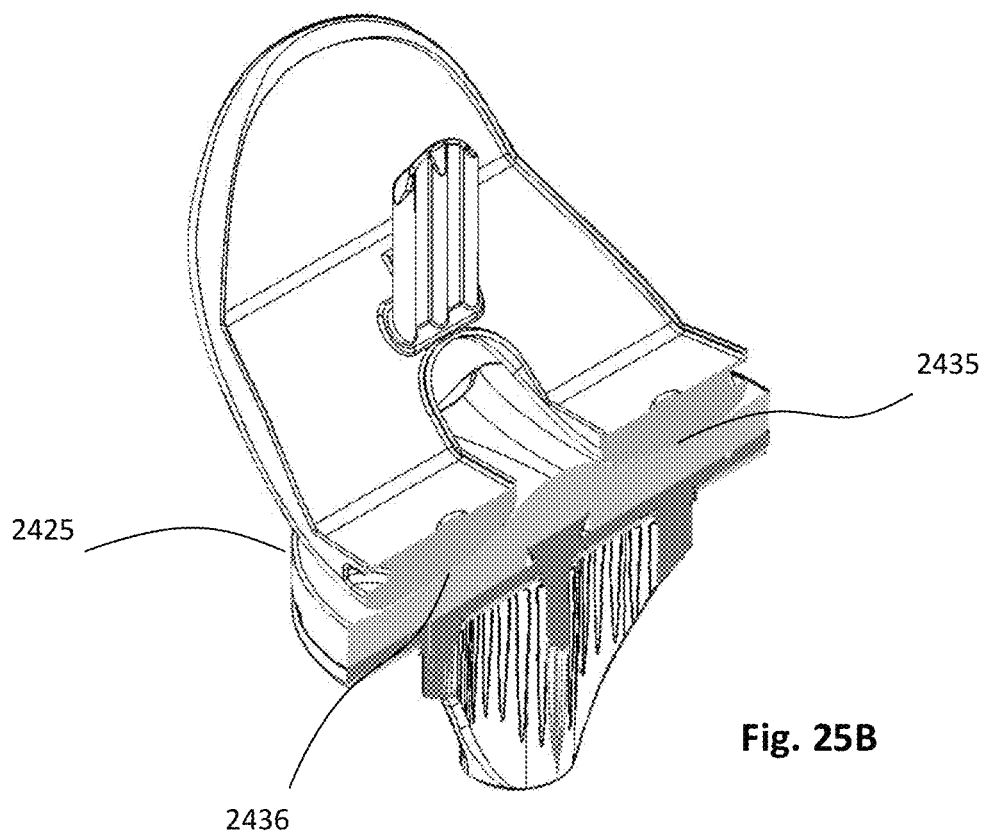
FIG. 25B is a perspective posterior view of the knee prosthesis assembly of FIG. 25A with a medial-lateral cross-section.
Figure 25C:
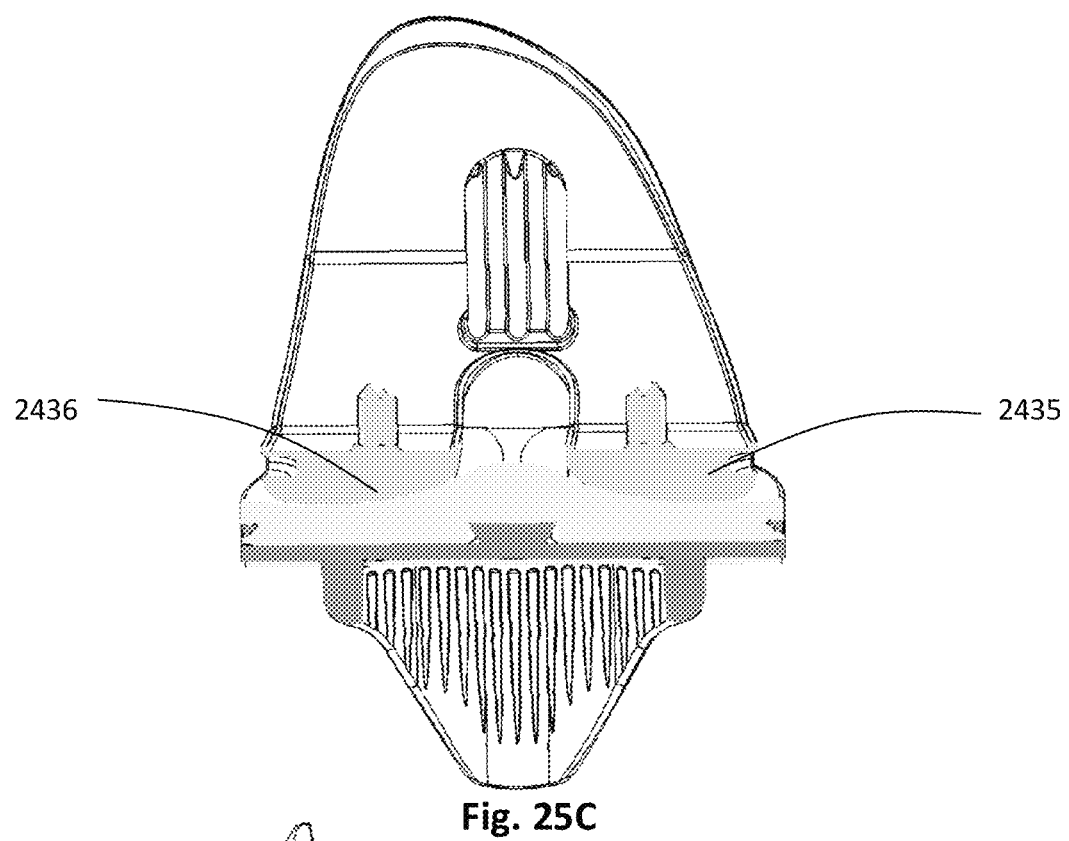
FIG. 25C is a posterior view of the knee prosthesis assembly of FIG. 25B.
Figure 25D:
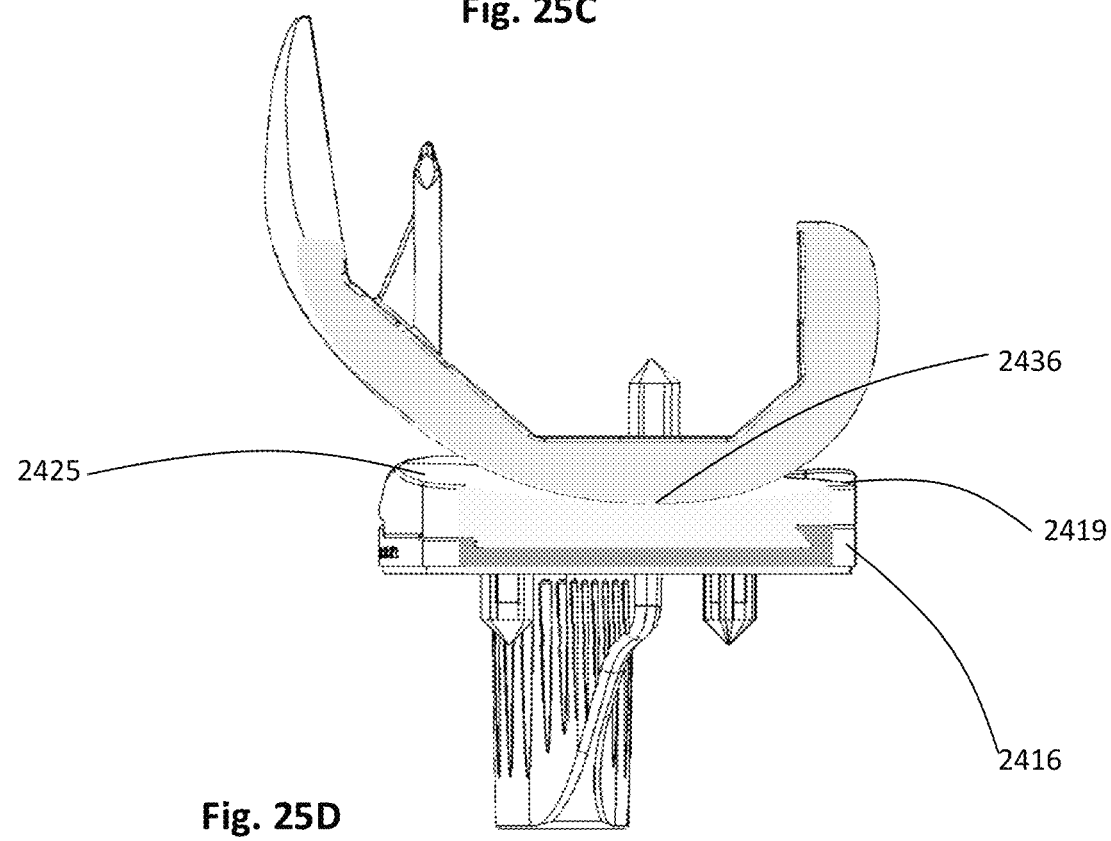
FIG. 25D is a lateral view of the knee prosthesis assembly of FIG. 25A with an anterior-posterior cross-section through the lateral articulation surface.
Figure 25E:
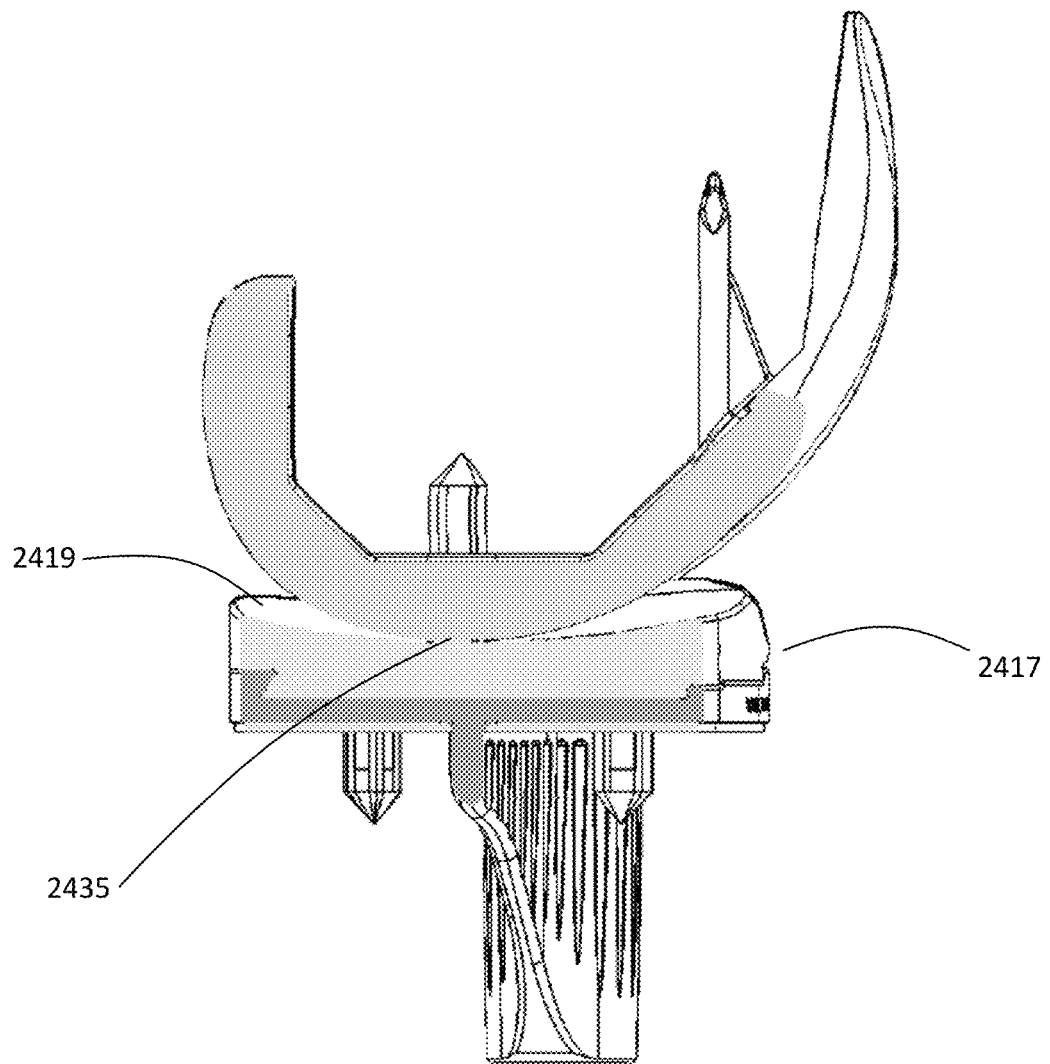
FIG. 25E is a medial view of the knee prosthesis assembly of FIG. 25A an anterior-posterior cross-section through the medial articulation surface.

FIGS. 24D and 24E show lateral and medial views of the insert 2410, respectively. In 24D, the lateral articulation side 2414 with lateral perimeter 2429 is shown. The lateral articulation surface 2421 may meet the lateral perimeter 2429 at a lateral high point 2430. The lateral low point 2431 may be toward the center of the lateral articulation surface 2421. In 24E, the medial articulation side 2413 with medial perimeter 2426 is shown. The medial articulation surface 2420 may meet the medial perimeter 2426 at a medial high point 2427 at or adjacent the medial posterior section 2422. The medial low point 2428 may be closer to the medial anterior section 2423 and toward the medial perimeter 2426. The high points 2427 2430 and low points 2428 2431 on both the medial articulation side 2413 and lateral articulation side 2414 are in relation to the base 2411. The difference between the medial high point 2427 and the medial low point 2428 may be greater than the difference between the lateral high point 2430 and the lateral low point 2431. The greater difference in height on the medial articulation side may be represented by the medial ramp 2419.

The medial posterior section 2422 may include the medial ramp 2419, which may begin at the medial high point 2427 and extend away from the medial high point 2427 anteriorly toward the medial low point 2428. Following the surface topography of the medial ramp 2419, the medial articulation surface 2420 tends to have a gradient from the medial high point 2427 toward the medial low point 2428 near the medial anterior section 2423 and to the medial perimeter 2426. The gradient of the lateral articulation surface 2421 flows to the lateral low point 2431. Therefore, movement down gradients on the medial articulation surface 2420 and lateral articulation surface 2421 may be asymmetric. The lateral articulation surface 2421 may be generally concave toward the lateral low point 2431. The location of the medial low point 2428 may cause the directionality of the gradient from the medial ramp 2419 along the medial articulation surface 2420, which causes an object or a mass to move down the gradient in the direction created by the medial ramp 2419. The medial ramp 2419 and the different heights along the medial perimeter 2426 and the medial articulation surface 2420 may create a medial dwell point 2435 that is transient along the gradient. The approximate gradient is represented by dashed lines in FIG. 24F.

The medial posterior side 2415, of the medial articulation side 2413, may have a medial thickness defined by the medial high point 2427 at the medial perimeter 2426, which may correspond to the medial ramp 2419, and/or the base 2411. The lateral posterior side 2416, of the lateral articulation side 2414, may have a lateral thickness defined by the lateral high point 2430 at the lateral perimeter 2429 and the base 2411. Because of the medial ramp 2419, the medial articulation side 2413 may have a greater thickness than the lateral articulation side 2414.

The medial ramp 2419 and the gradient it creates along the medial articulation surface 2420 towards the medial low point 2428 may cause a translation or movement of the medial condyle 2402 greater than a translation or movement of the lateral condyle 2403, as the knee and assembly 2400 range from 0 degree of flexion, or extension, to 90 degrees of flexion. The medial condyle 2402 may move down the medial ramp 2419 such that the medial dwell point 2435 migrates anteriorly and outwardly toward the medial perimeter 2426 as the degree of flexion increases. The lateral condyle 2403 may remain in generally the same location near the lateral low point 2431 so the lateral dwell point 2436 may remain in generally the same location. The lateral condyle 2403 may also migrate as the knee moves into flexion, so that the lateral dwell point 2436 migrates posteriorly and outwardly concurrently as the medial dwell point 2435 migrates anteriorly and outwardly. The asymmetric translation of the medial dwell point 2435 and lateral dwell point 2436 may create a tibiofemoral rotation between extension and flexion.

FIGS. 25-31 demonstrate the movement of the medial dwell point 2435 relative to the lateral dwell point 2436 during flexion of the assembly 2400. FIGS. 25A-25E show a posterior view of the composed assembly 2400 in 0 degree flexion, or "straight leg," in a left knee. FIG. 25A is a medial-lateral cross-section perspective view of the assembly 2400. Generally, the femoral component 2401 contacts the insert 2410 at dwell points. Dwell points are the points of contact between two surfaces. The medial condylar articulation surface 2404 meets the medial articulation surface 2420 at a medial dwell point 2435. The lateral condylar articulation surface 2405 meets the lateral articulation surface 2421 at a lateral dwell point 2436. FIGS. 25B and 25C show the medial dwell point 2435 and the lateral dwell point 2436 at what may be considered a starting position, in 0 degrees flexion. FIG. 25D is an anterior-posterior cross-section through the lateral articulation side 2414 of the insert 2410. The medial ramp 2419 is visible (in the background) and shows the height difference between the medial posterior side 2415 and the lateral posterior side 2416. FIG. 25E is an anterior-posterior cross-section through the medial articulation side 2413 of the insert 2410; the medial ramp 2419 is visible and is occluding the lower lateral posterior side 2416.

Figure 26A:
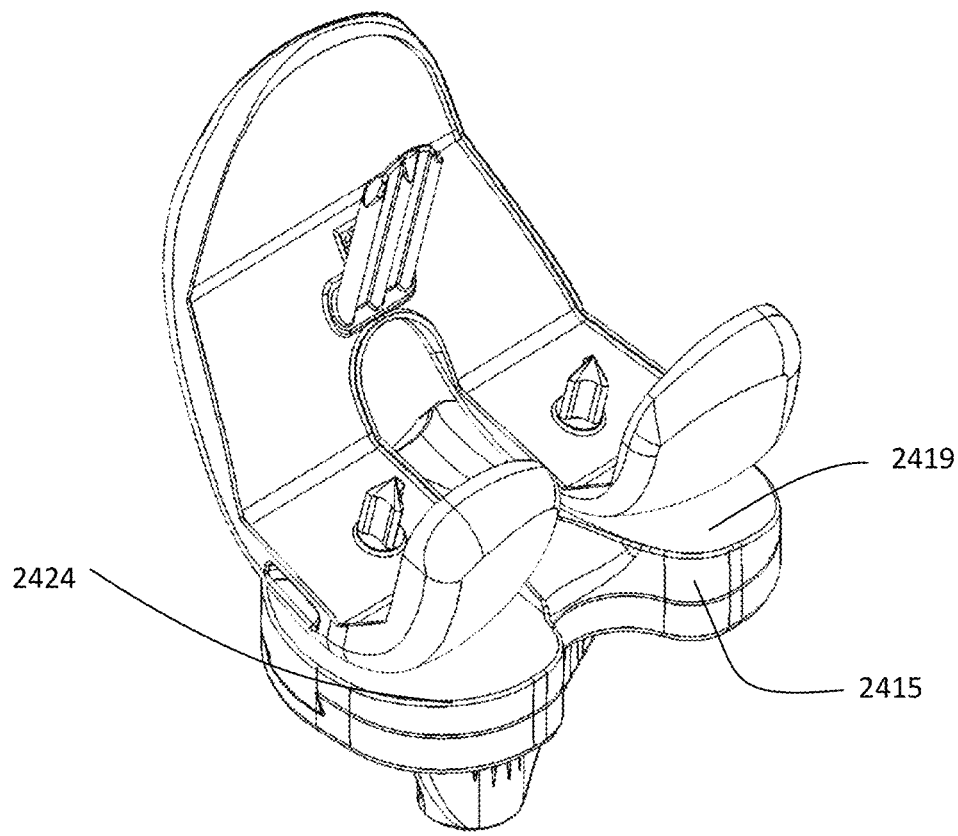
FIG. 26A is perspective posterior view of a knee prosthesis assembly in 15 degree flexion.
Figure 26B:
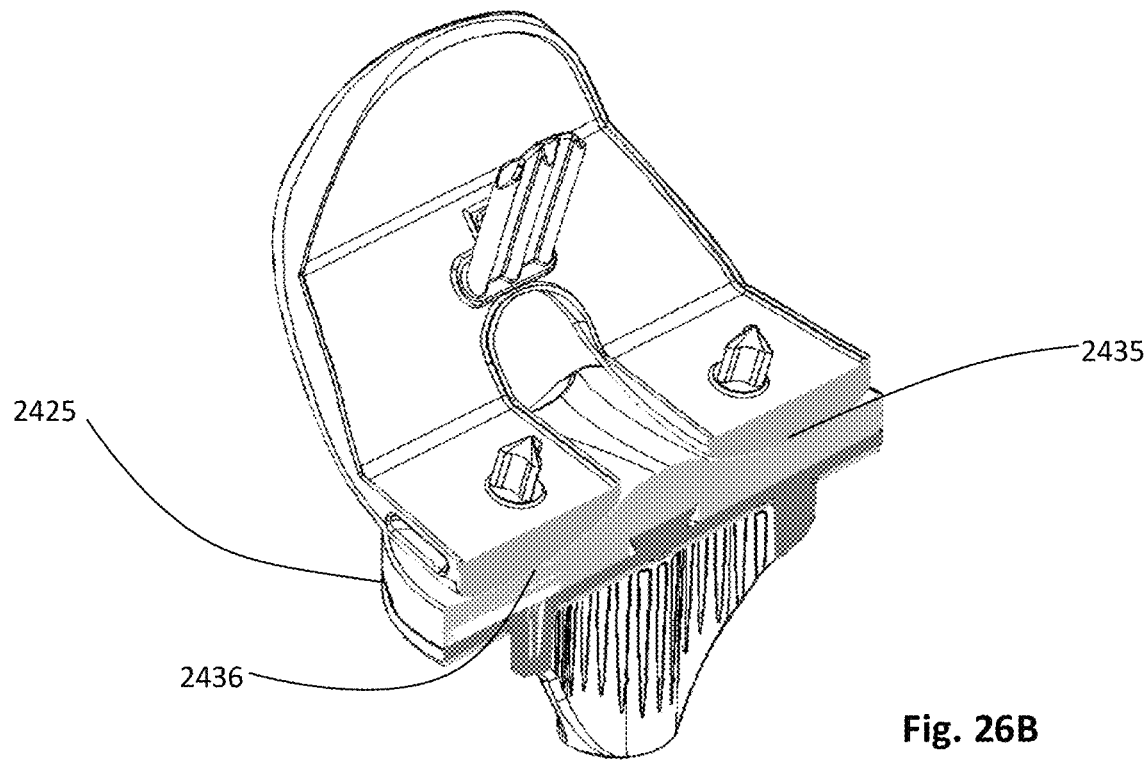
FIG. 26B is a perspective posterior view of the knee prosthesis assembly of FIG. 26A with a medial-lateral cross-section.
Figure 26C:
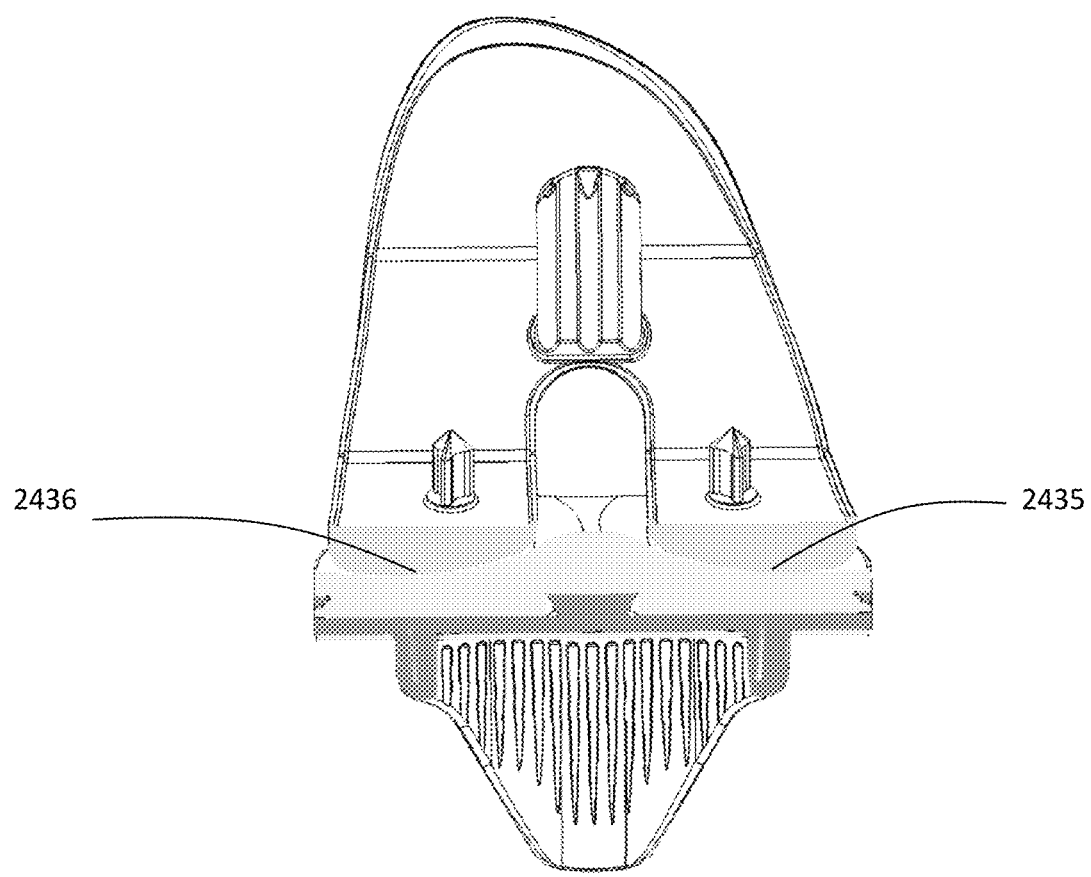
FIG. 26C is a posterior view of the knee prosthesis assembly of FIG. 26B.
Figure 26D:
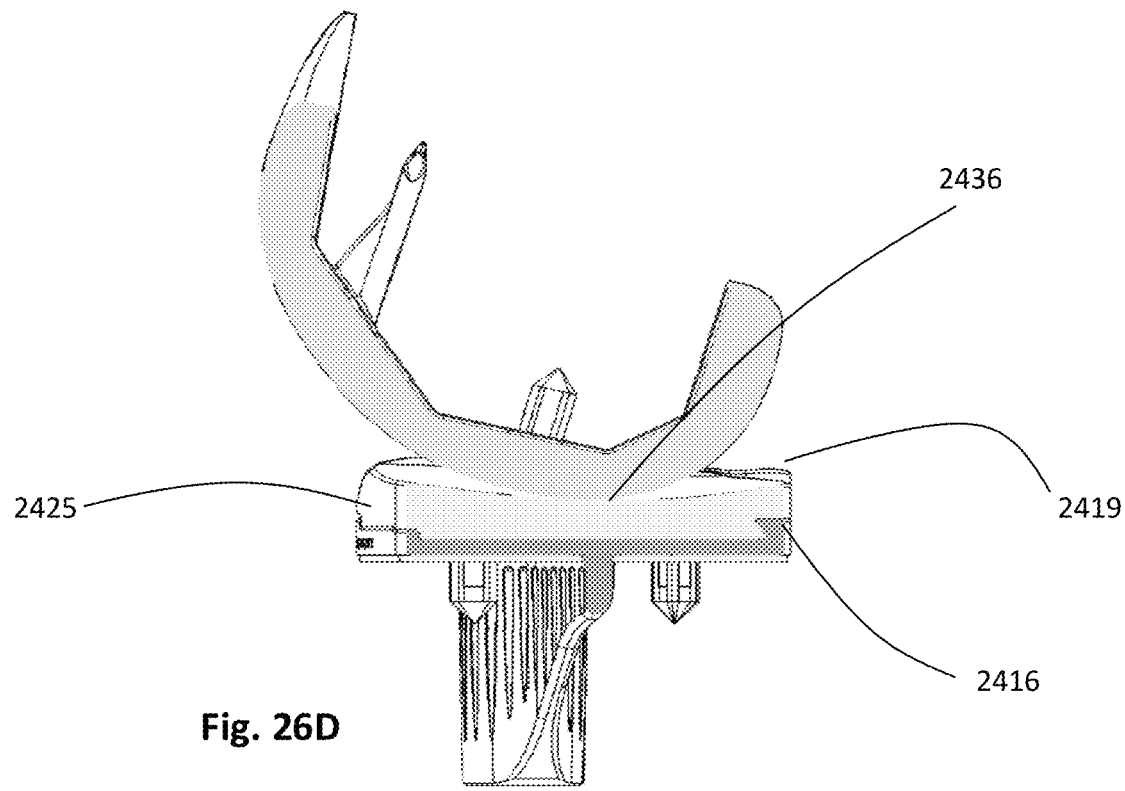
FIG. 26D is a lateral view of the knee prosthesis assembly of FIG. 26A with an anterior-posterior cross-section through the lateral articulation surface.
Figure 26E:
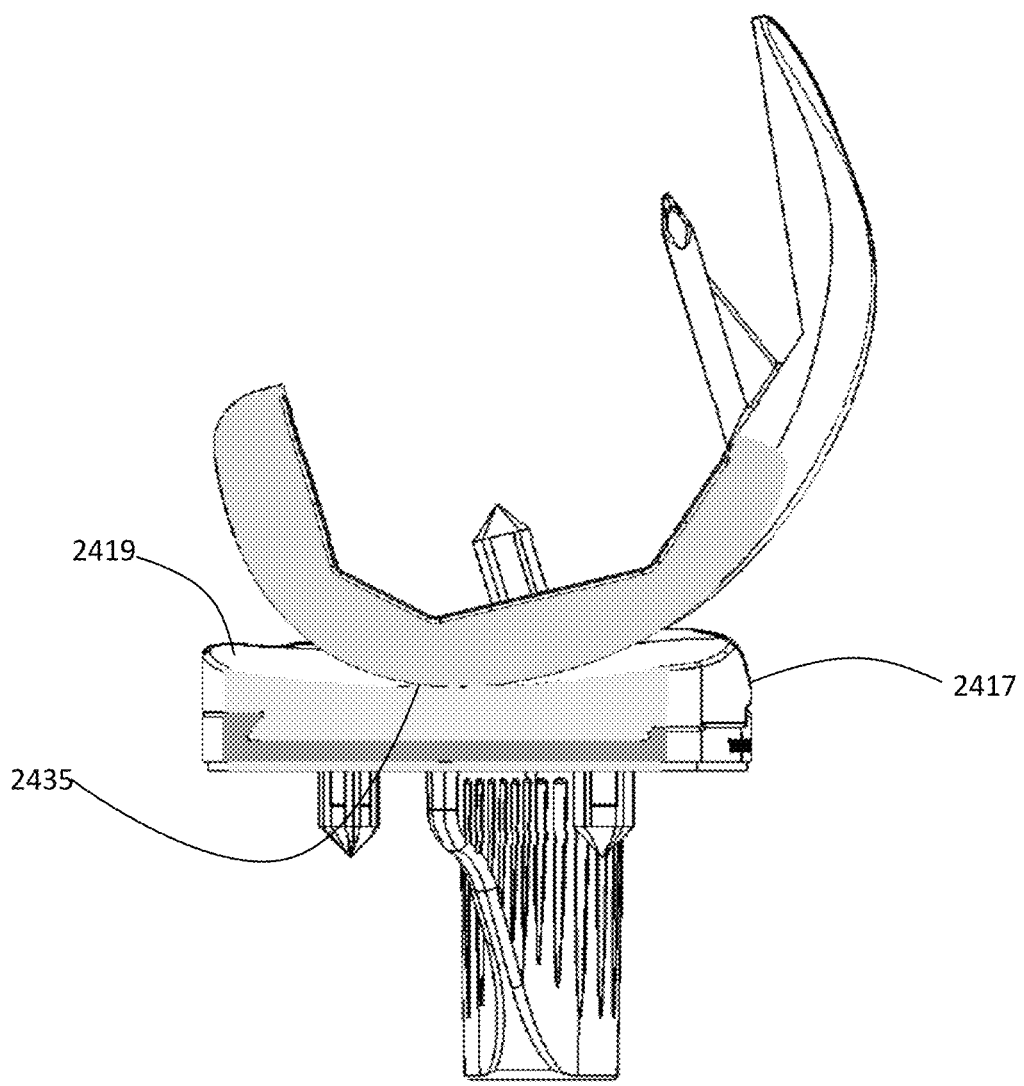
FIG. 26E is a medial view of the knee prosthesis assembly of FIG. 26A an anterior-posterior cross-section through the medial articulation surface.

FIGS. 26A-26E show a posterior view of the composed assembly 2400 in 15 degree flexion, in a left knee. FIG. 26A is a medial-lateral cross-section perspective view of the assembly 2400. The medial condylar articulation surface 2404 meets the medial articulation surface 2420 at a medial dwell point 2435. The lateral condylar articulation surface 2405 meets the lateral articulation surface 2421 at a lateral dwell point 2436. FIGS. 26B and 26C show the medial dwell point 2435 and the lateral dwell point 2436 at what may be considered a starting position, in 15 degrees flexion. FIG. 26D is an anterior-posterior cross-section through the lateral articulation side 2414 of the insert 2410. The medial ramp 2419 is visible (in the background) and shows the height difference between the medial posterior side 2415 and the lateral posterior side 2416. FIG. 26E is an anterior-posterior cross-section through the medial articulation side 2413 of the insert 2410; the medial ramp 2419 is visible and is occluding the lower lateral posterior side 2416. Relative to 0 degrees flexion, the medial dwell point 2435 has moved slightly and the lateral dwell point 2436 has not moved significantly.

Figure 27A:
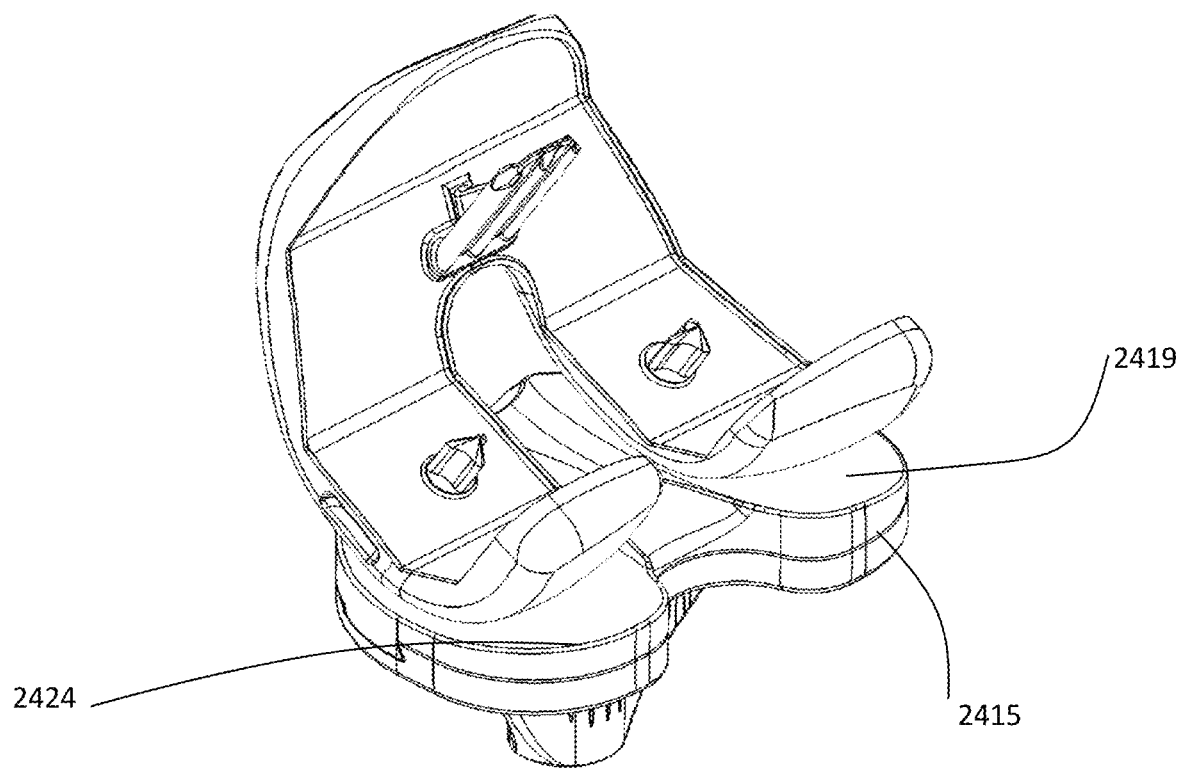
FIG. 27A is perspective posterior view of a knee prosthesis assembly in 30 degree flexion.
Figure 27B:
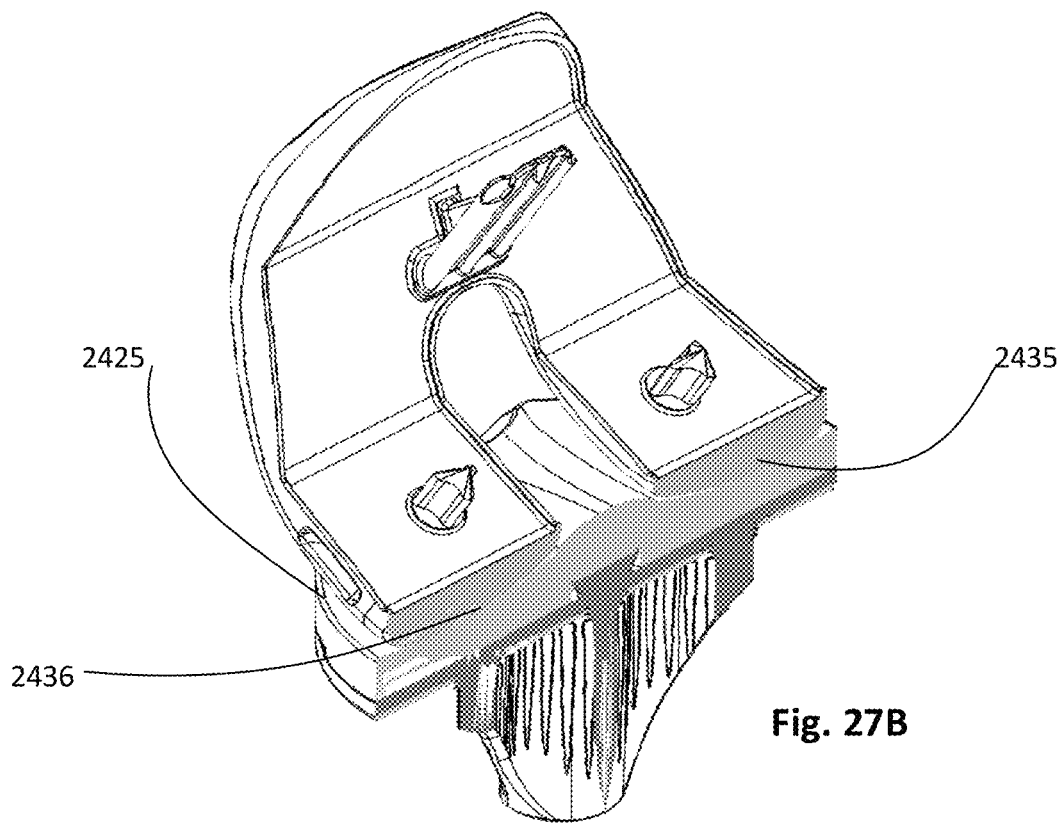
FIG. 27B is a perspective posterior view of the knee prosthesis assembly of FIG. 27A with a medial-lateral cross-section.
Figure 27C:
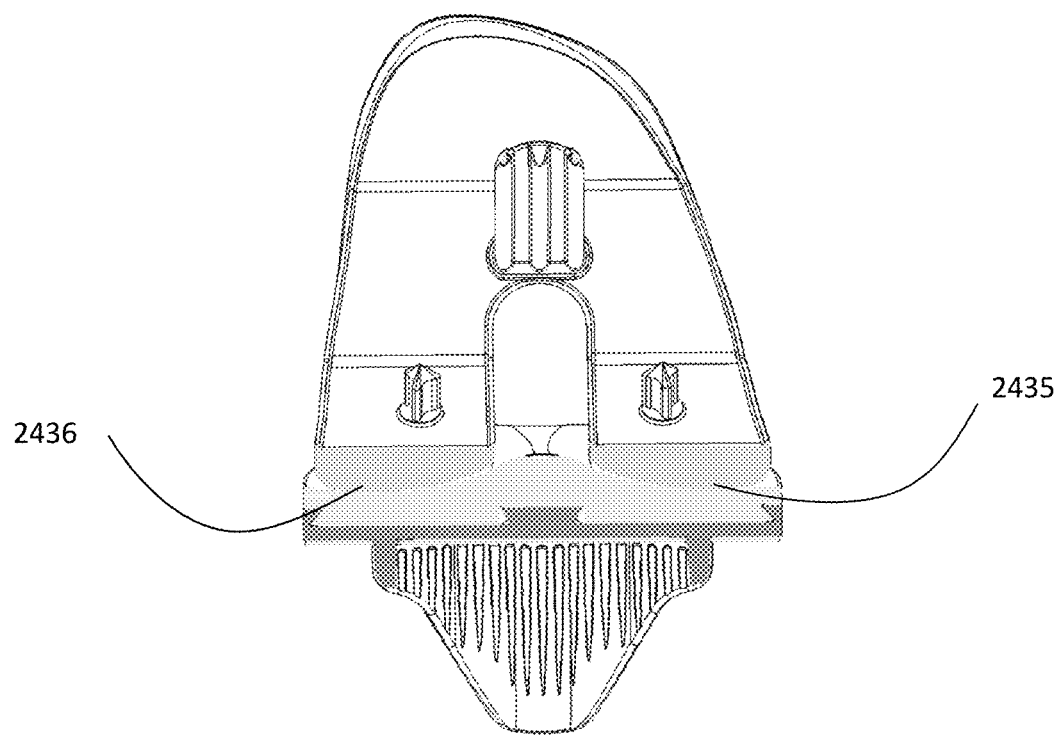
FIG. 27C is a posterior view of the knee prosthesis assembly of FIG. 27B.
Figure 27D:
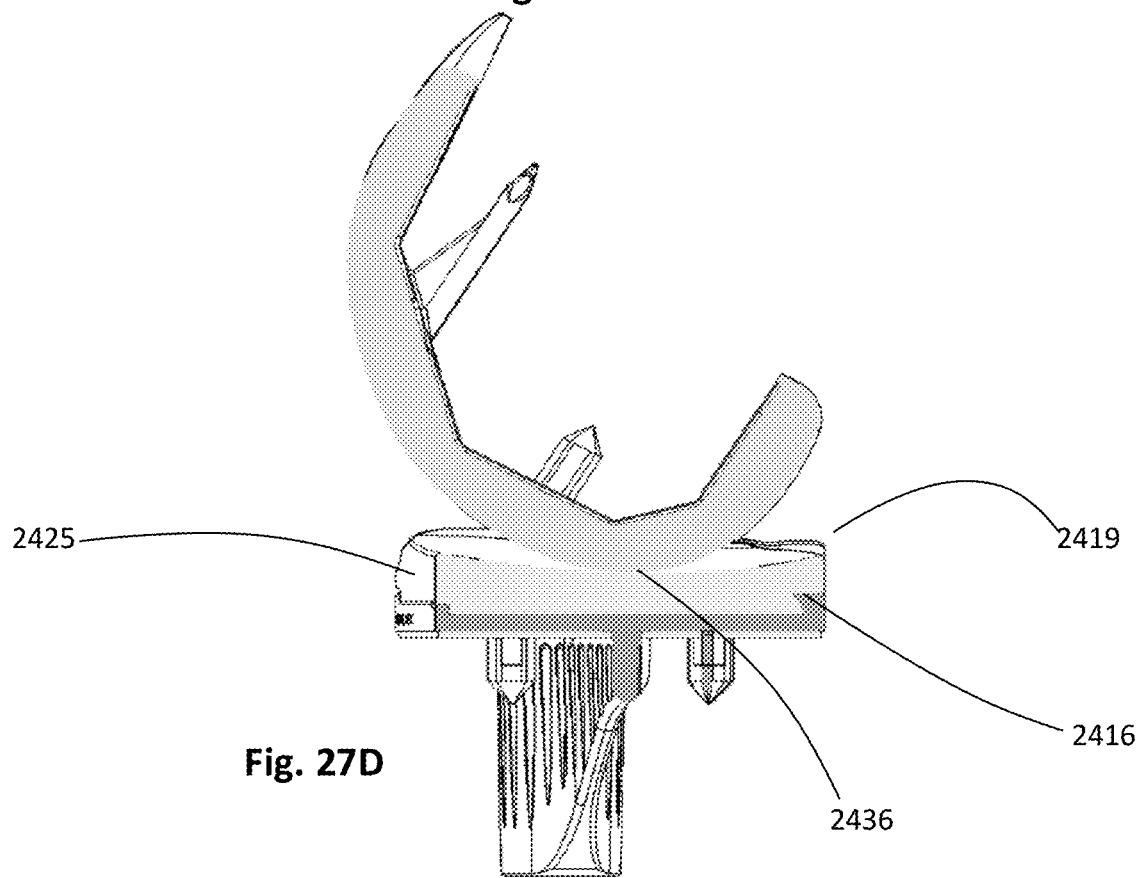
FIG. 27D is a lateral view of the knee prosthesis assembly of FIG. 27A with an anterior-posterior cross-section through the lateral articulation surface.
Figure 27E:
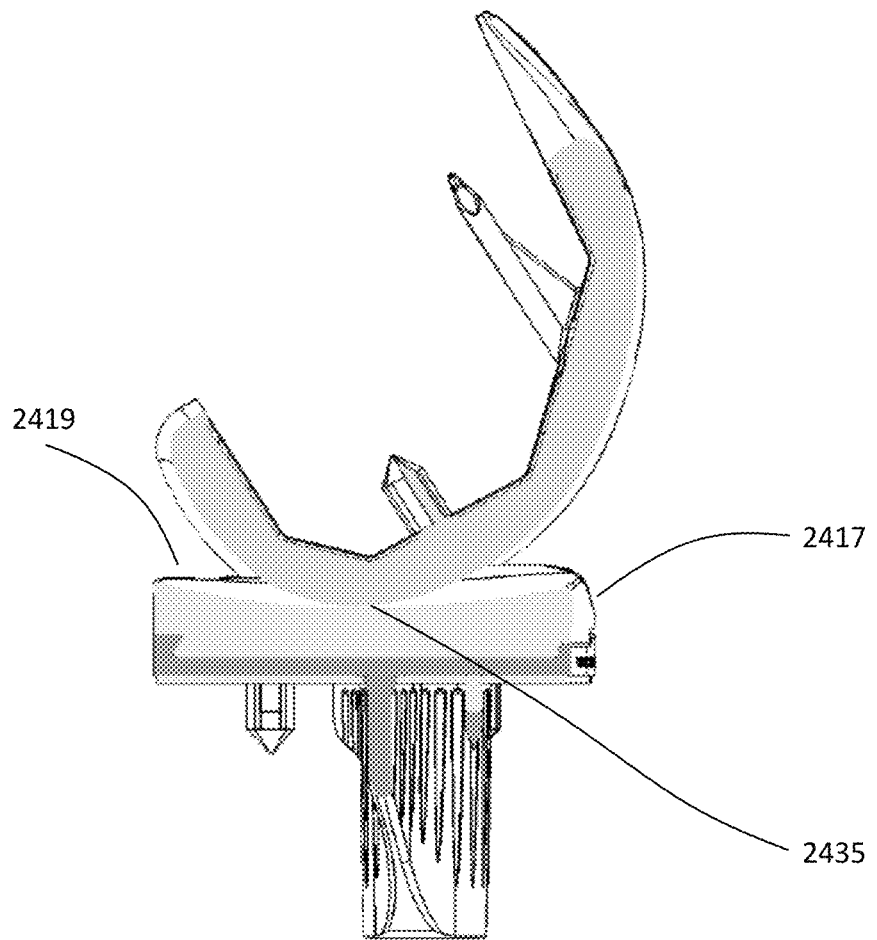
FIG. 27E is a medial view of the knee prosthesis assembly of FIG. 27A an anterior-posterior cross-section through the medial articulation surface.

FIGS. 27A-27E show a posterior view of the composed assembly 2400 in 30 degree flexion, in a left knee. FIG. 27A is a medial-lateral cross-section perspective view of the assembly 2400. The medial condylar articulation surface 2404 meets the medial articulation surface 2420 at a medial dwell point 2435. The lateral condylar articulation surface 2405 meets the lateral articulation surface 2421 at a lateral dwell point 2436. FIGS. 27B and 27C show the medial dwell point 2435 and the lateral dwell point 2436 at what may be considered a starting position, in 30 degrees flexion. FIG. 27D is an anterior-posterior cross-section through the lateral articulation side 2414 of the insert 2410. The medial ramp 2419 is visible (in the background) and shows the height difference between the medial posterior side 2415 and the lateral posterior side 2416. FIG. 27E is an anterior-posterior cross-section through the medial articulation side 2413 of the insert 2410; the medial ramp 2419 is visible and is occluding the lower lateral posterior side 2416. Relative to 0 degrees flexion, the medial dwell point 2435 has moved slightly and the lateral dwell point 2436 has not moved significantly.

Figure 28A:
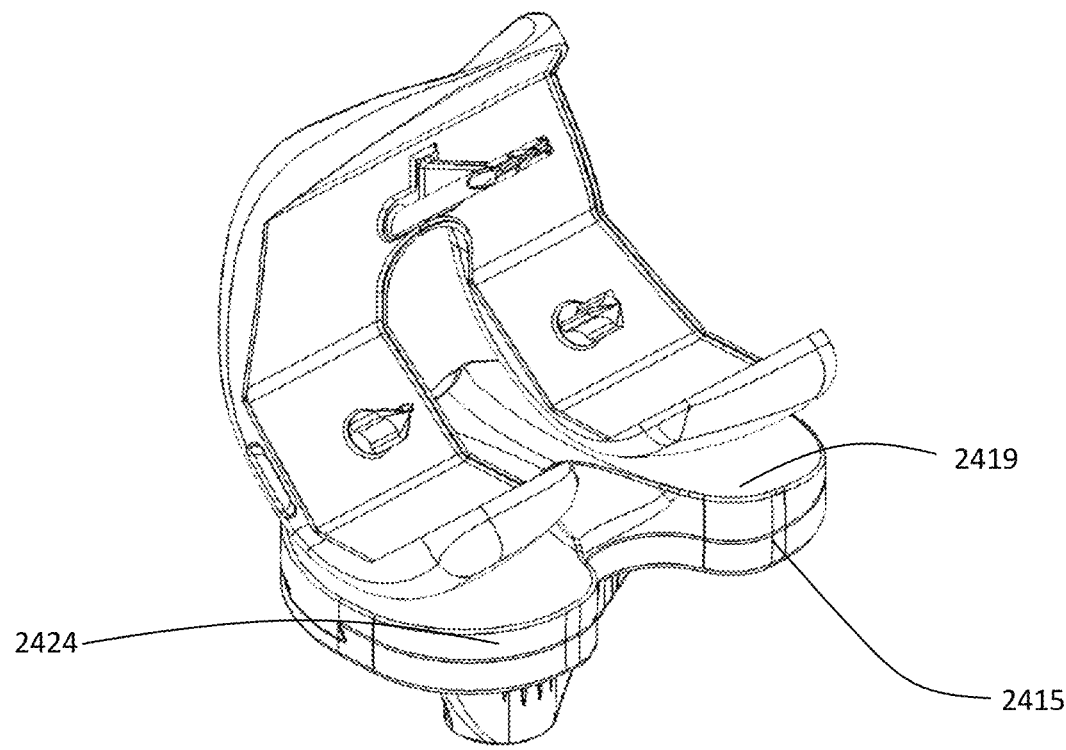
FIG. 28A is perspective posterior view of a knee prosthesis assembly in 45 degree flexion.
Figure 28B:
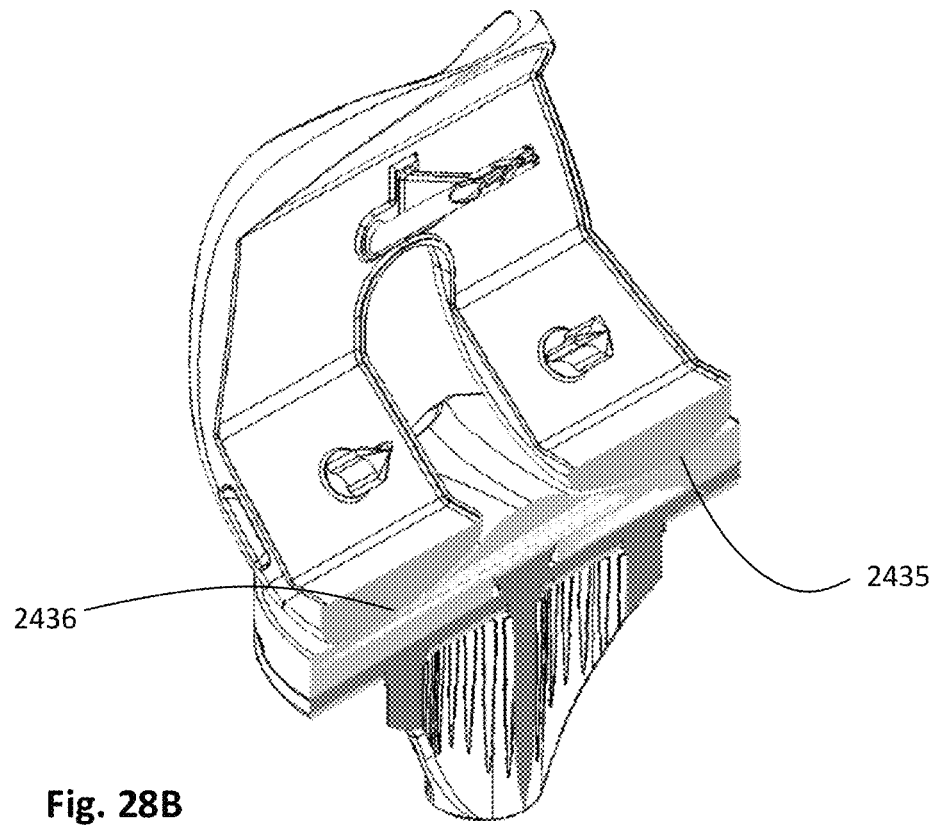
FIG. 28B is a perspective posterior view of the knee prosthesis assembly of FIG. 28A with a medial-lateral cross-section.
Figure 28C:
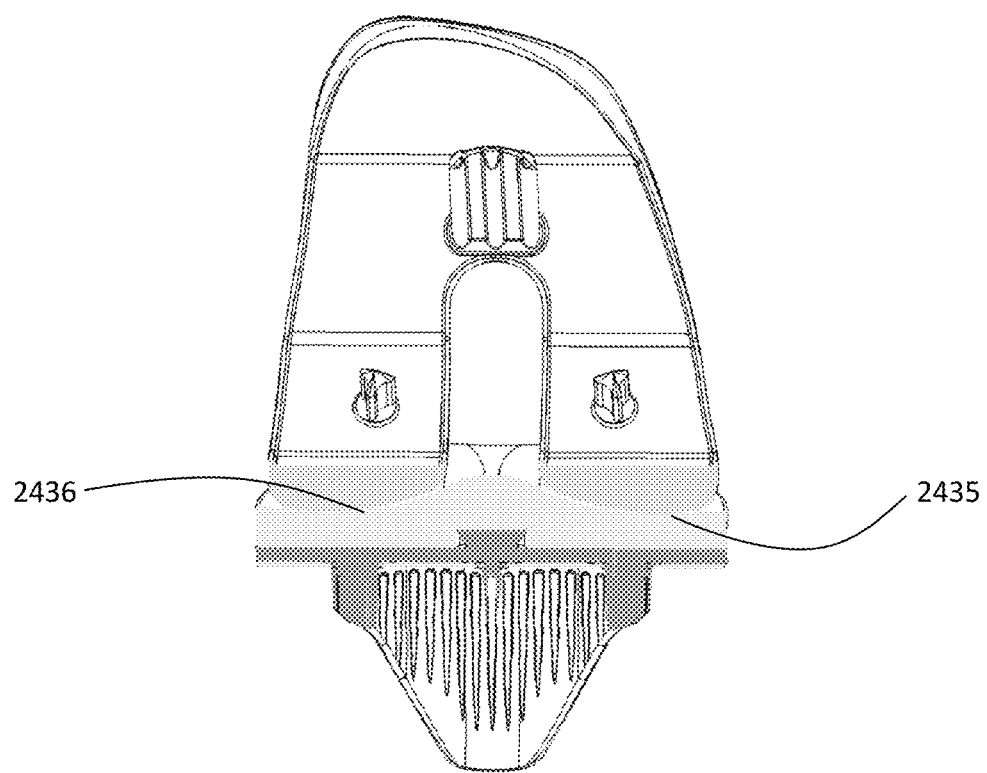
FIG. 28C is a posterior view of the knee prosthesis assembly of FIG. 28B.
Figure 28D:
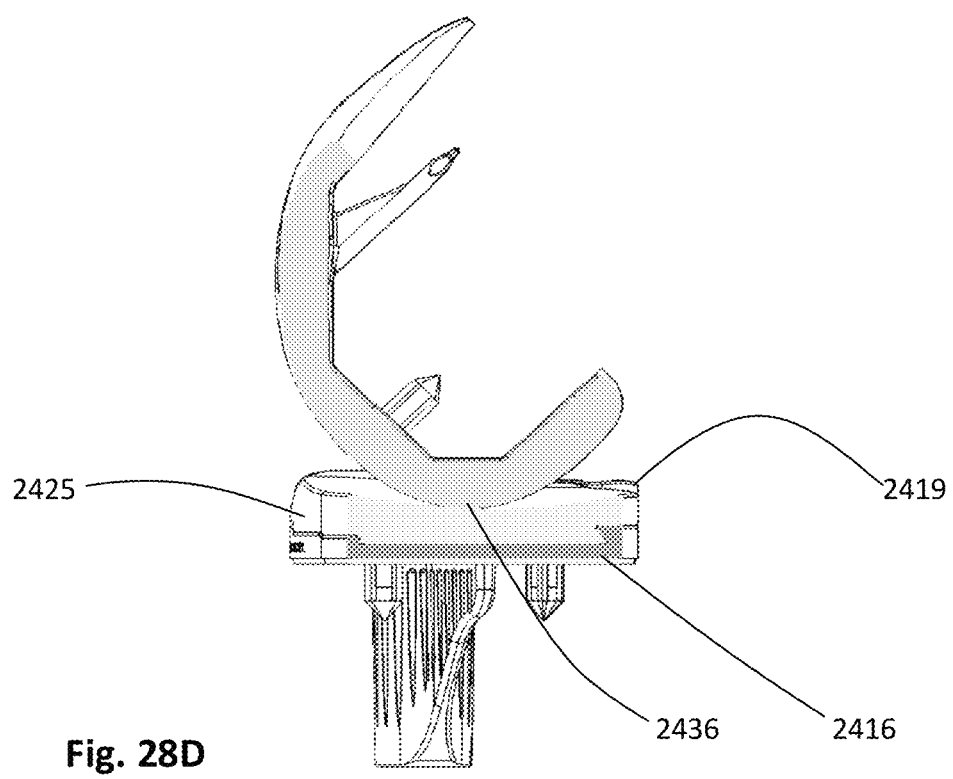
FIG. 28D is a lateral view of the knee prosthesis assembly of FIG. 28A with an anterior-posterior cross-section through the lateral articulation surface.
Figure 28E:
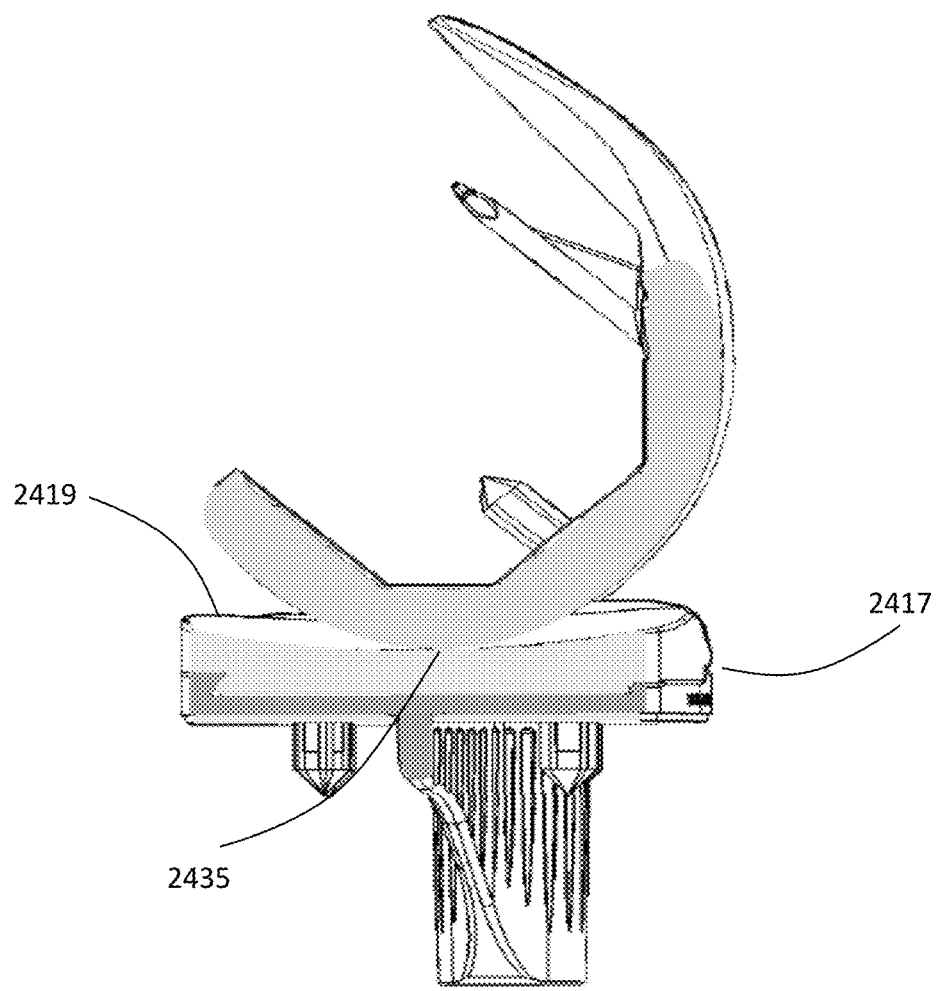
FIG. 28E is a medial view of the knee prosthesis assembly of FIG. 28A an anterior-posterior cross-section through the medial articulation surface.

FIGS. 28A-28E show a posterior view of the composed assembly 2400 in 45 degree flexion, in a left knee. FIG. 28A is a medial-lateral cross-section perspective view of the assembly 2400. The medial condylar articulation surface 2404 meets the medial articulation surface 2420 at a medial dwell point 2435. The lateral condylar articulation surface 2405 meets the lateral articulation surface 24214 at a lateral dwell point 2436. FIGS. 28B and 28C show the medial dwell point 2435 and the lateral dwell point 2436 at what may be considered a starting position, in 45 degrees flexion. FIG. 28D is an anterior-posterior cross-section through the lateral articulation side 2414 of the insert 2410. The medial ramp 2419 is visible (in the background) and shows the height difference between the medial posterior side 2415 and the lateral posterior side 2416. FIG. 28E is an anterior-posterior cross-section through the medial articulation side 2413 of the insert 2410; the medial ramp 2419 is visible and is occluding the lower lateral posterior side 2416. Relative to 0 degrees flexion, the medial dwell point 2435 has moved slightly and the lateral dwell point 2436 has not moved significantly.

Figure 29A:
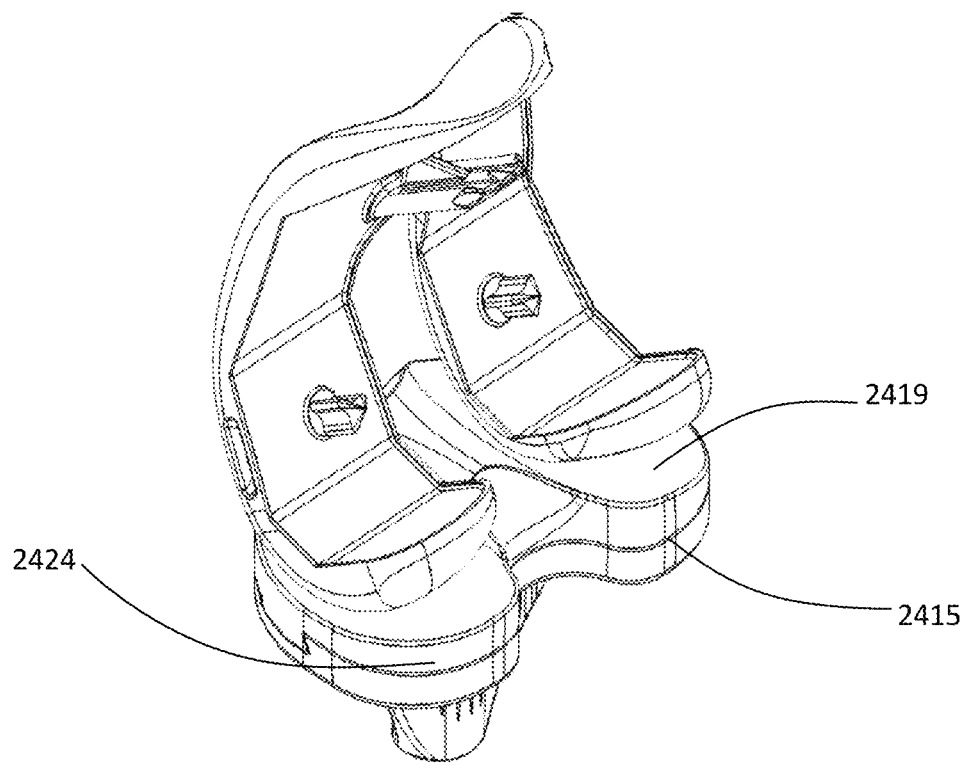
FIG. 29A is perspective posterior view of a knee prosthesis assembly in 60 degree flexion.
Figure 29B:
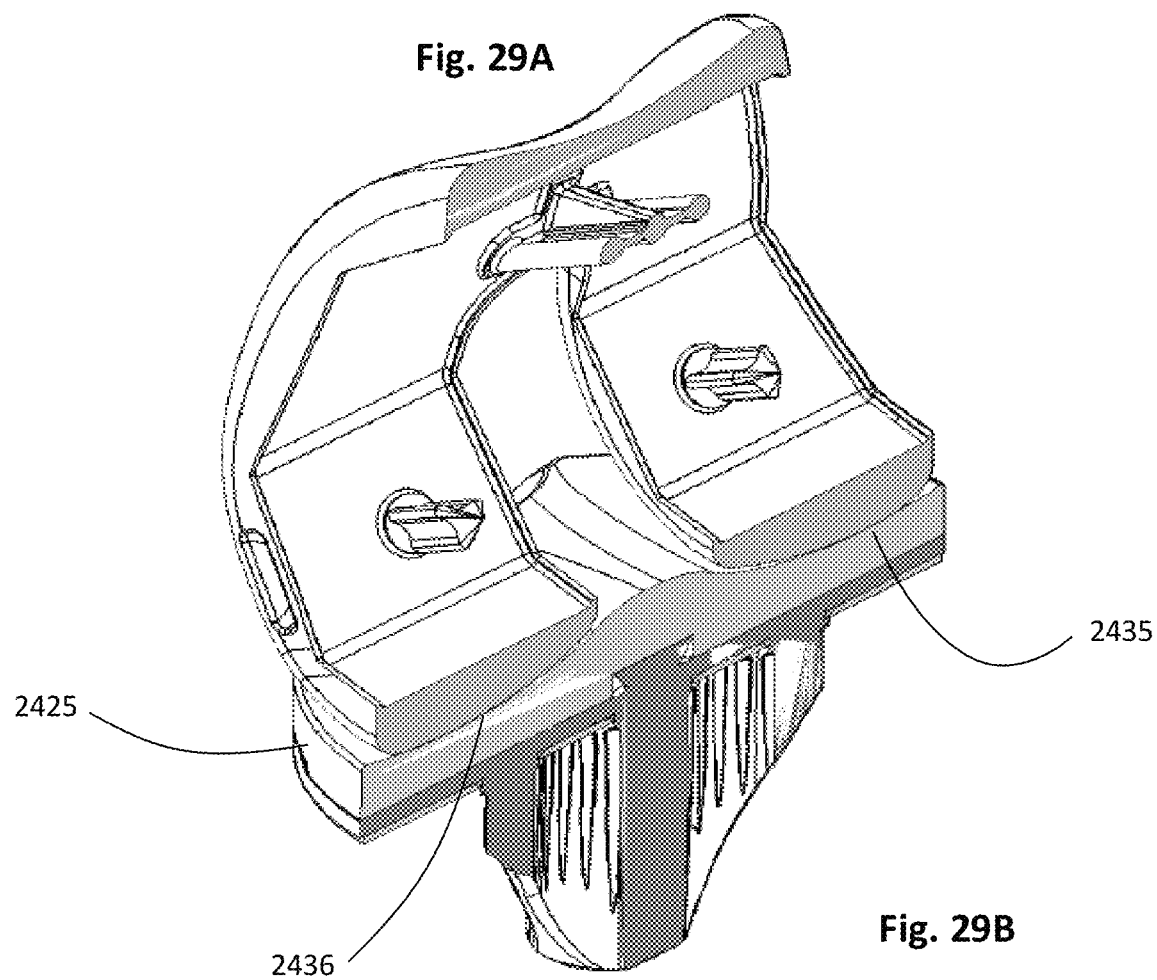
FIG. 29B is a perspective posterior view of the knee prosthesis assembly of FIG. 29A with a medial-lateral cross-section.
Figure 29C:
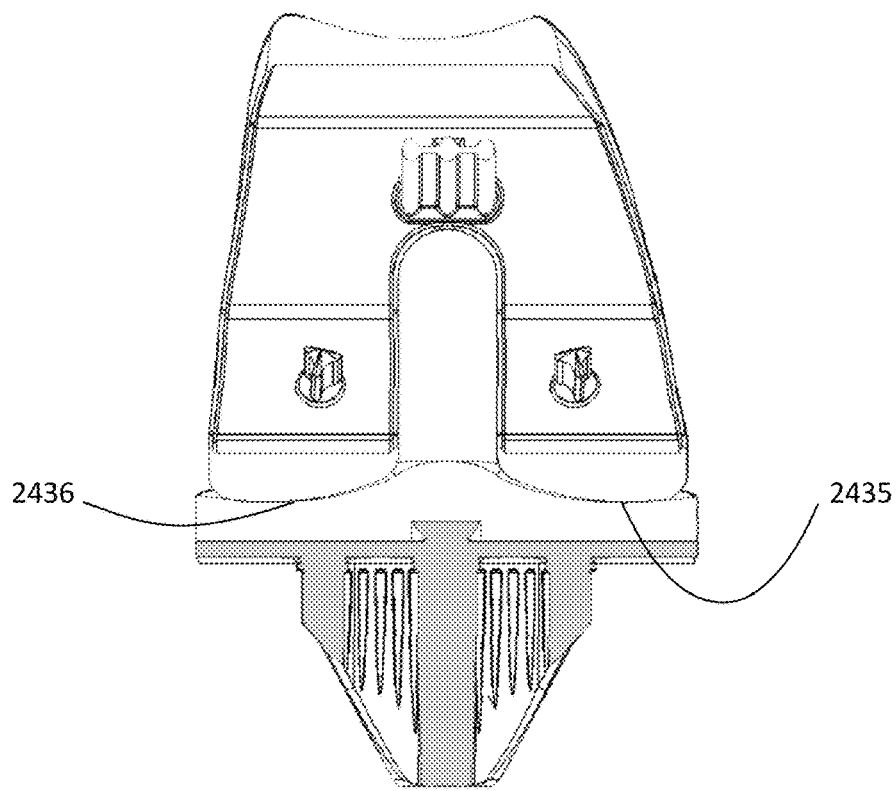
FIG. 29C is a posterior view of the knee prosthesis assembly of FIG. 29B.
Figure 29D:
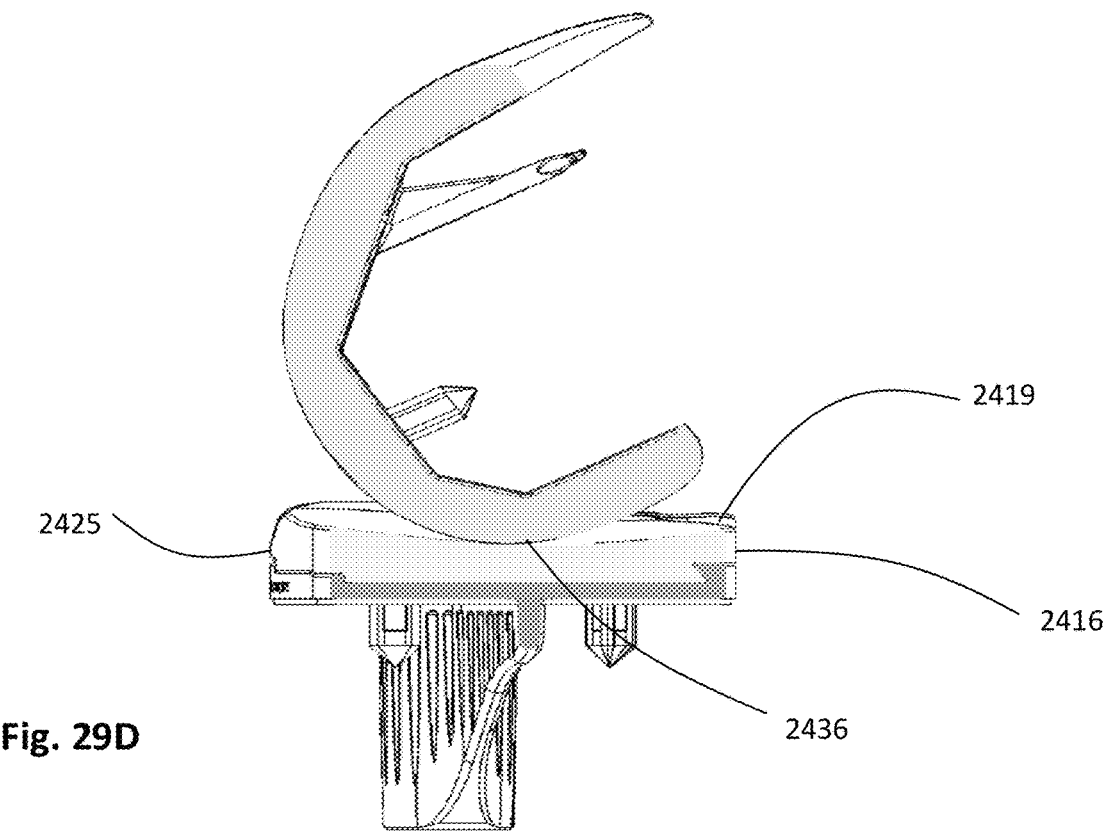
FIG. 29D is a lateral view of the knee prosthesis assembly of FIG. 29A with an anterior-posterior cross-section through the lateral articulation surface.
Figure 29E:
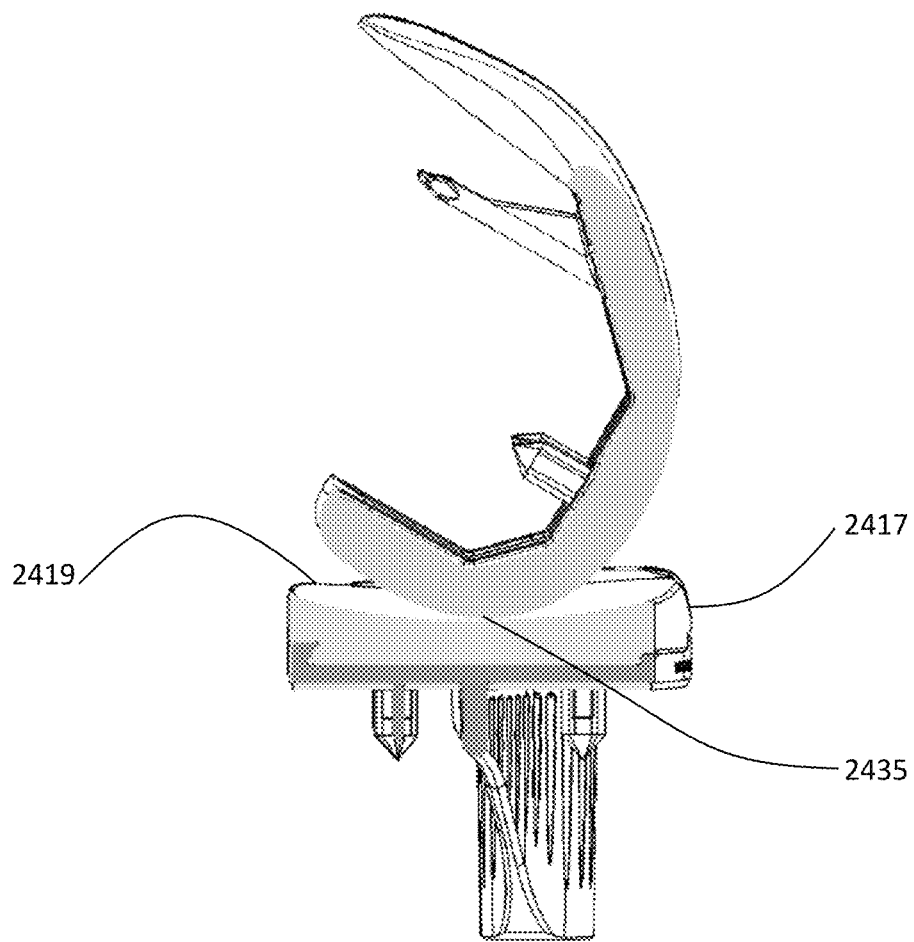
FIG. 29E is a medial view of the knee prosthesis assembly of FIG. 29A an anterior-posterior cross-section through the medial articulation surface.

FIGS. 29A-29E show a posterior view of the composed assembly 2400 in 60 degree flexion, in a left knee. FIG. 29A is a medial-lateral cross-section perspective view of the assembly 2400. The medial condylar articulation surface 2404 meets the medial articulation surface 2420 at a medial dwell point 2435. The lateral condylar articulation surface 2405 meets the lateral articulation surface 2421 at a lateral dwell point 2436. FIGS. 29B and 29C show the medial dwell point 2435 and the lateral dwell point 2436 at what may be considered a starting position, in 60 degrees flexion. FIG. 29D is an anterior-posterior cross-section through the lateral articulation side 2414 of the insert 2410. The medial ramp 2419 is visible (in the background) and shows the height difference between the medial posterior side 2415 and the lateral posterior side 2416. FIG. 29E is an anterior-posterior cross-section through the medial articulation side 2413 of the insert 2410; the medial ramp 2419 is visible and is occluding the lower lateral posterior side 2416. Relative to 0 degrees flexion, the medial dwell point 2435 has moved anteriorly and outwardly toward the medial perimeter 2426 and the lateral dwell point 2436 has not moved significantly.

Figure 30A:
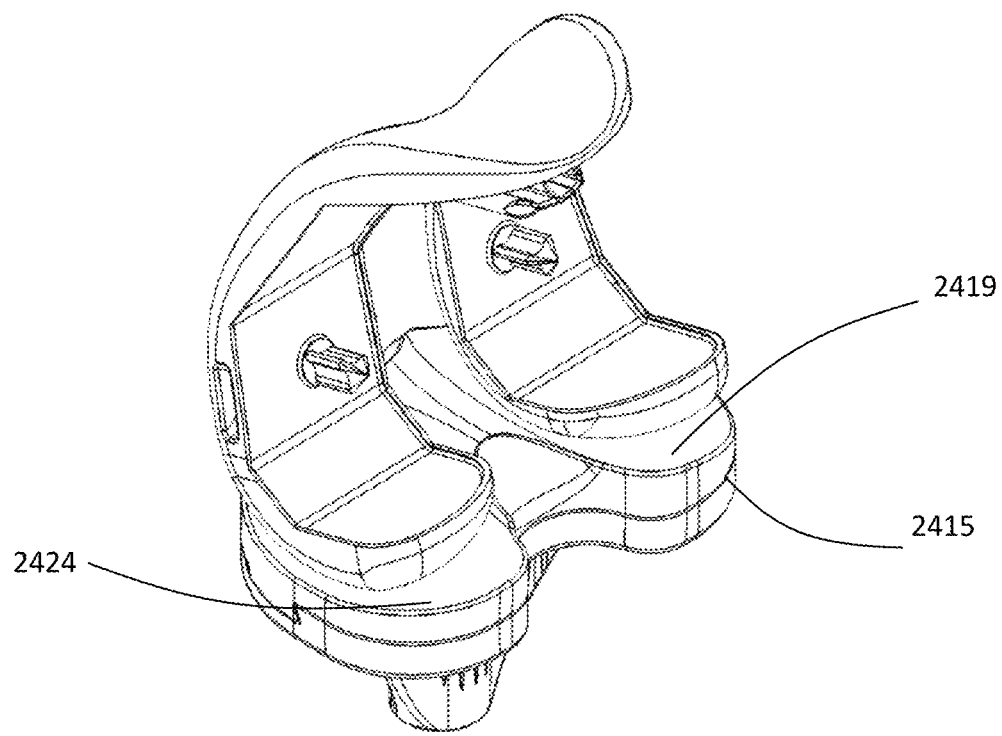
FIG. 30A is perspective posterior view of a knee prosthesis assembly in 75 degree flexion.
Figure 30B:
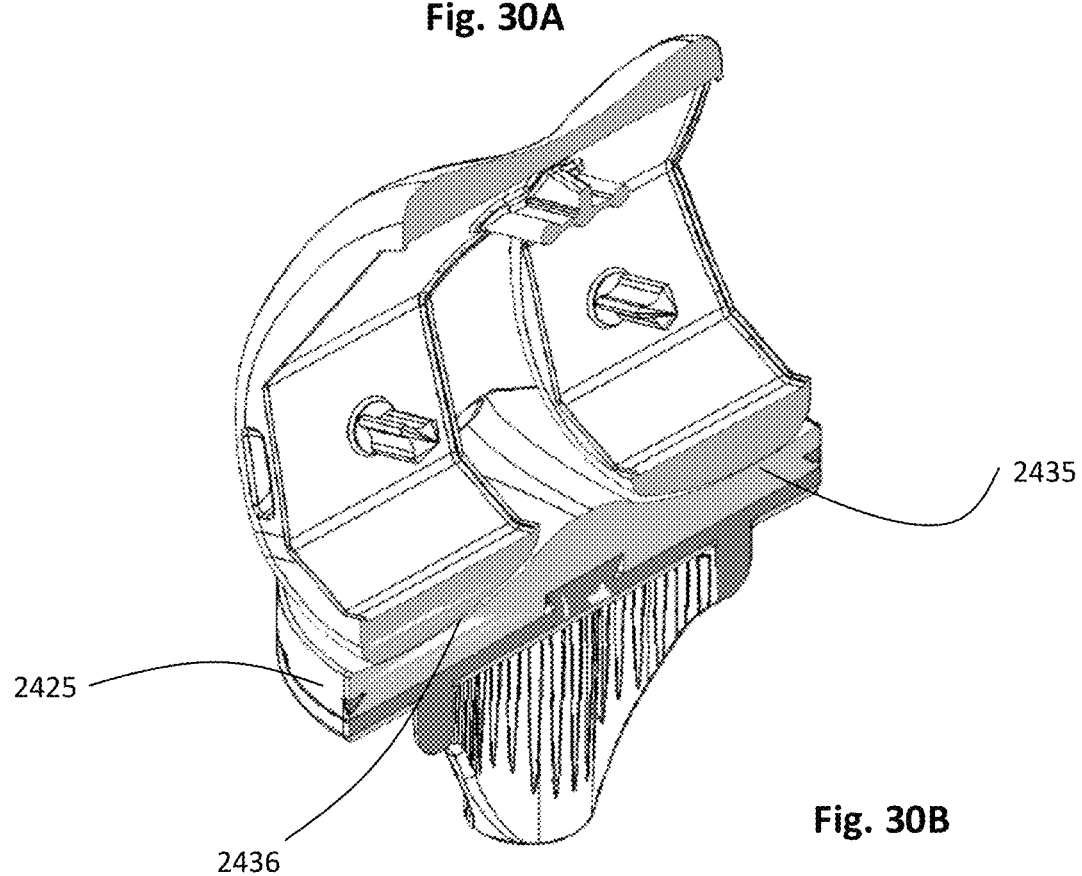
FIG. 30B is a perspective posterior view of the knee prosthesis assembly of FIG. 30A with a medial-lateral cross-section.
Figure 30C:
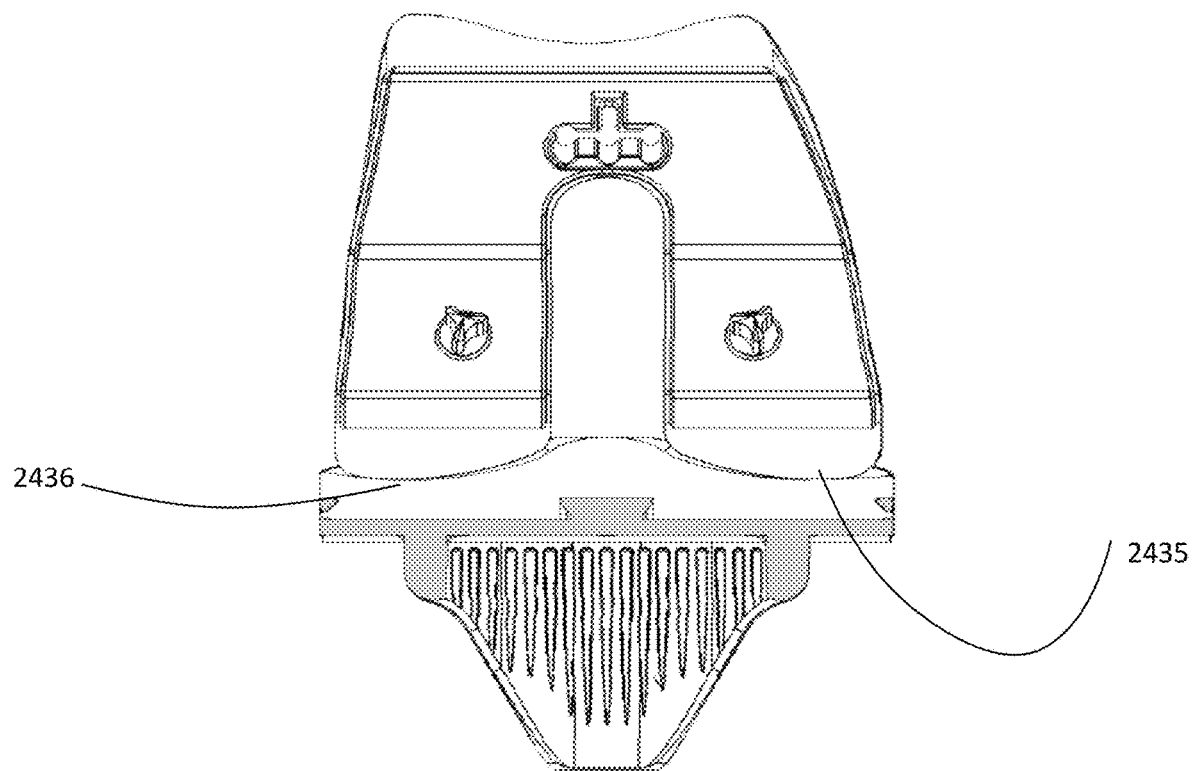
FIG. 30C is a posterior view of the knee prosthesis assembly of FIG. 30B.
Figure 30D:
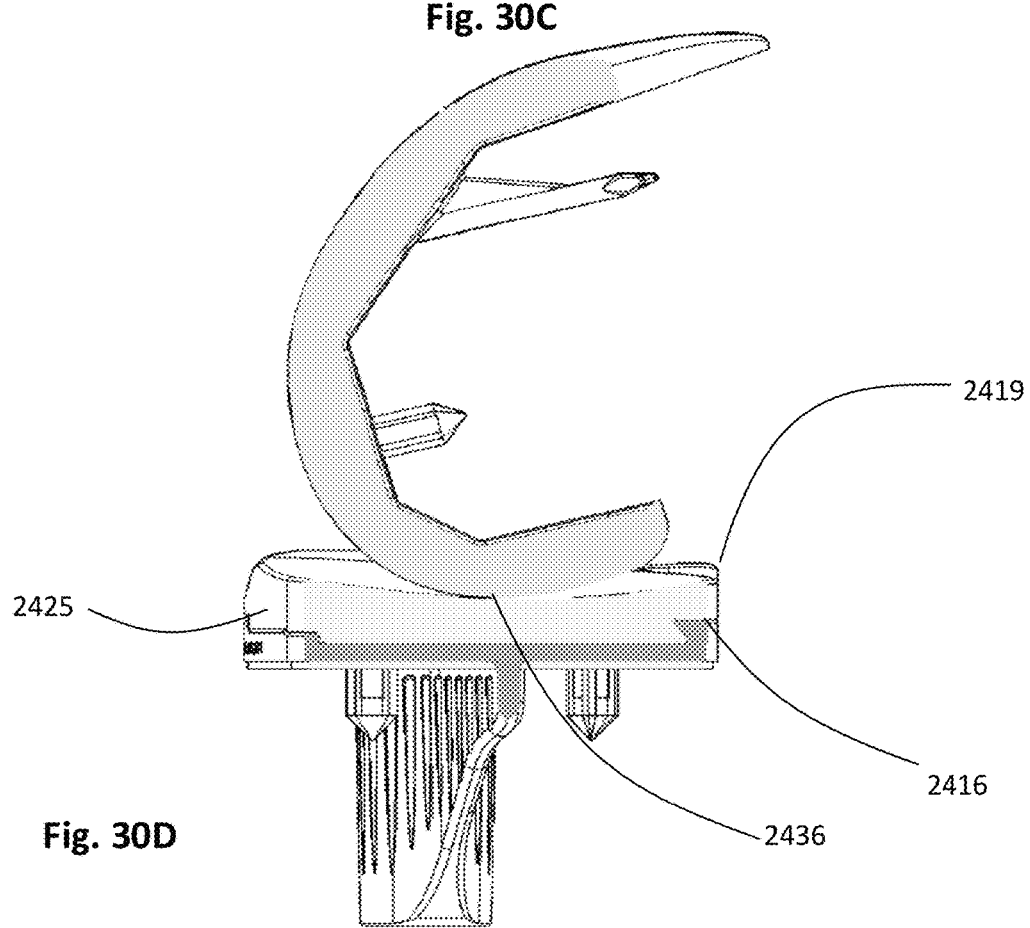
FIG. 30D is a lateral view of the knee prosthesis assembly of FIG. 30A with an anterior-posterior cross-section through the lateral articulation surface.
Figure 30E:
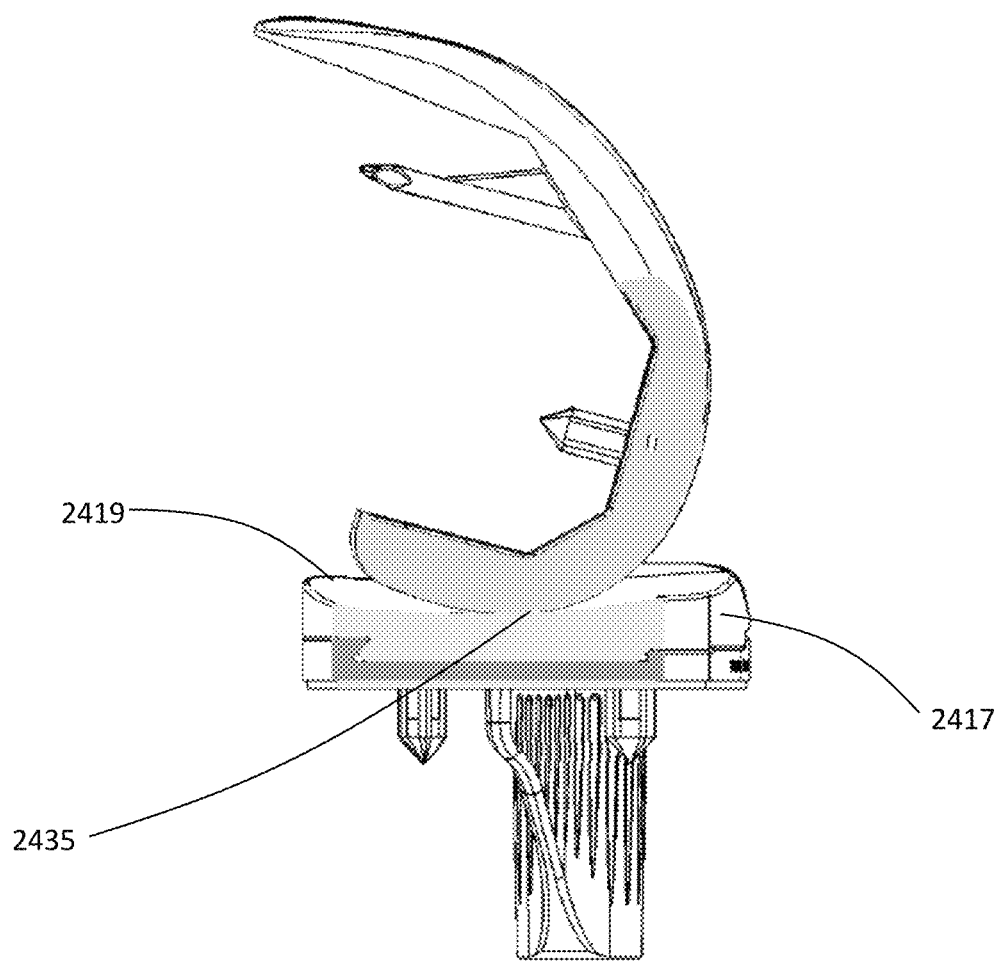
FIG. 30E is a medial view of the knee prosthesis assembly of FIG. 30A an anterior-posterior cross-section through the medial articulation surface.

FIGS. 30A-30E show a posterior view of the composed assembly 2400 in 75 degree flexion, in a left knee. FIG. 30A is a medial-lateral cross-section perspective view of the assembly 2400. The medial condylar articulation surface 2404 meets the medial articulation surface 2420 at a medial dwell point 2435. The lateral condylar articulation surface 2405 meets the lateral articulation surface 2421 at a lateral dwell point 2436. FIGS. 30B and 30C show the medial dwell point 2435 and the lateral dwell point 2436 at what may be considered a starting position, in 75 degrees flexion. FIG. 30D is an anterior-posterior cross-section through the lateral articulation side 2414 of the insert 2410. The medial ramp 2419 is visible (in the background) and shows the height difference between the medial posterior side 2415 and the lateral posterior side 2416. FIG. 30E is an anterior-posterior cross-section through the medial articulation side 2413 of the insert 2410; the medial ramp 2419 is visible and is occluding the lower lateral posterior side 2416. Relative to 0 degrees flexion, the medial dwell point 2435 has moved anteriorly and outwardly toward the medial perimeter 2426 and the lateral dwell point 2436 has not moved significantly.

Figure 31A:
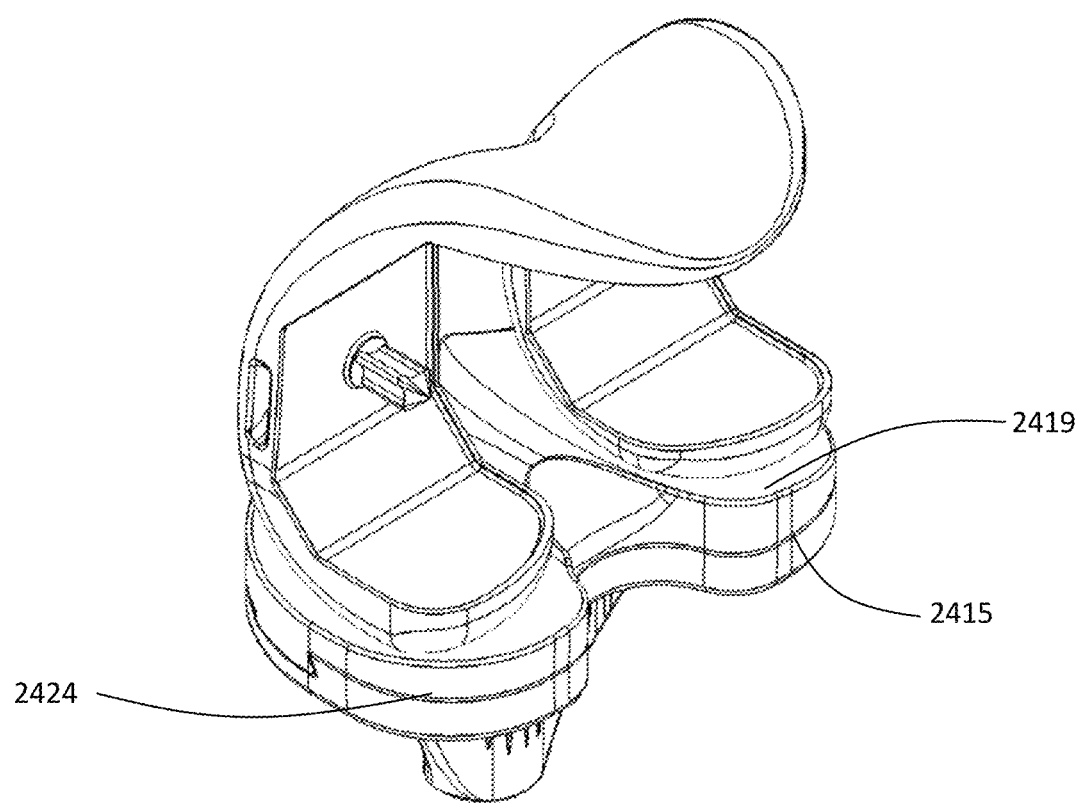
FIG. 31A is perspective posterior view of a knee prosthesis assembly in 90 degree flexion.
Figure 31B:
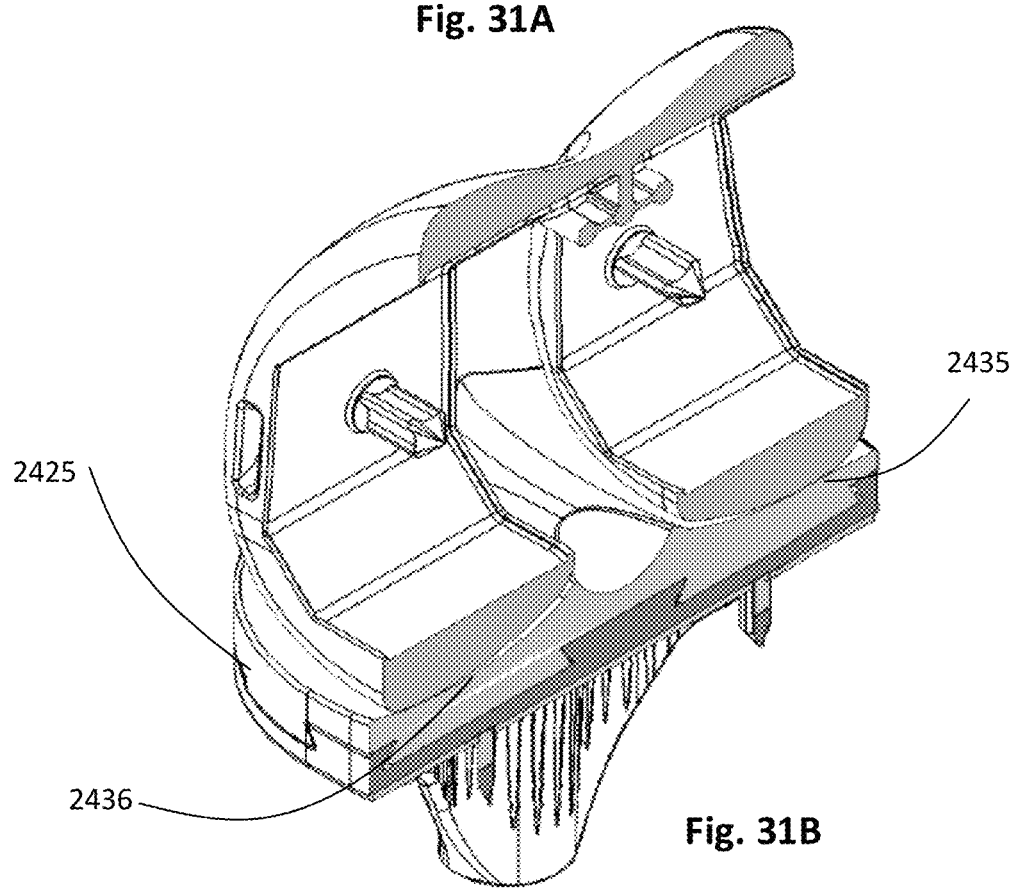
FIG. 31B is a perspective posterior view of the knee prosthesis assembly of FIG. 31A with a medial-lateral cross-section.
Figure 31C:
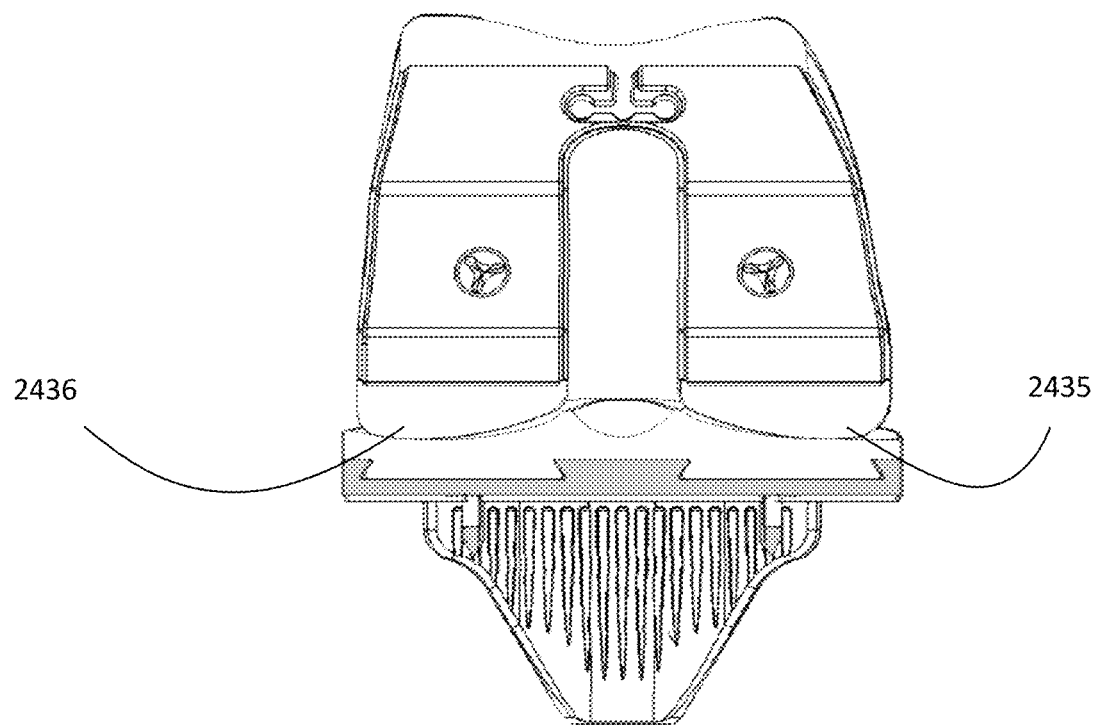
FIG. 31C is a posterior view of the knee prosthesis assembly of FIG. 31B.
Figure 31D:
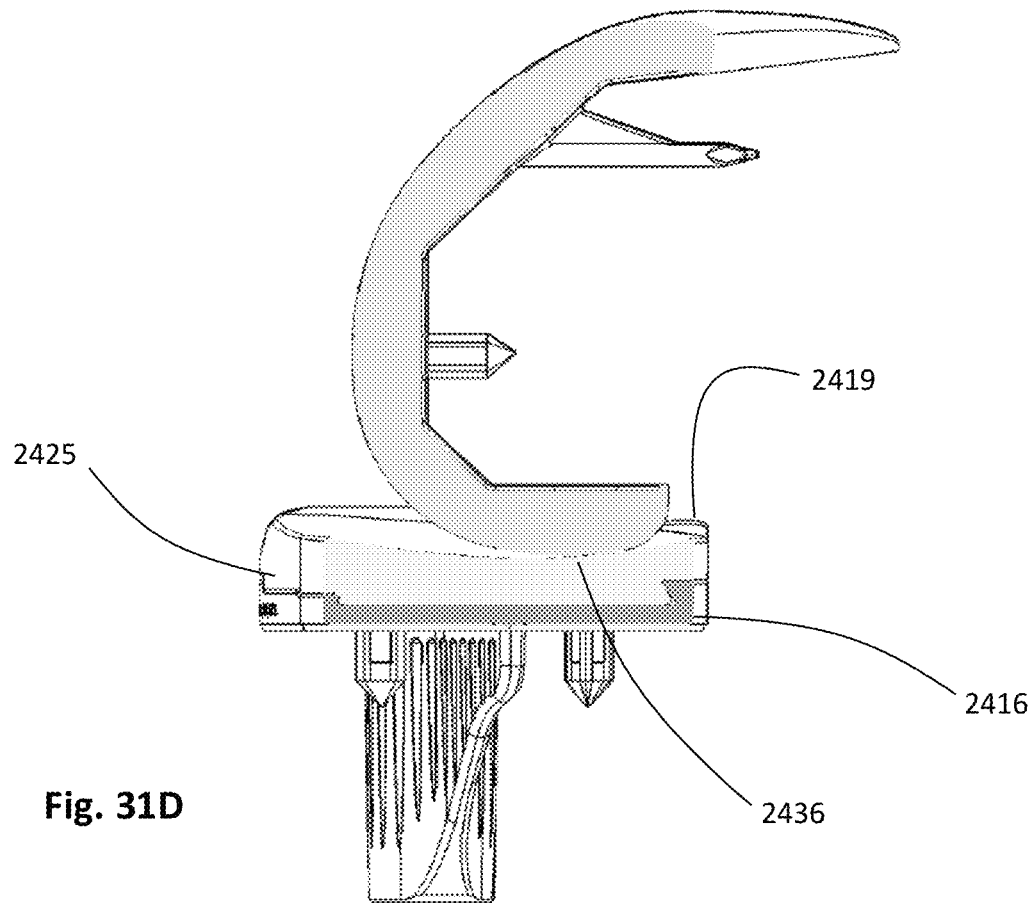
FIG. 31D is a lateral view of the knee prosthesis assembly of FIG. 31A with an anterior-posterior cross-section through the lateral articulation surface.
Figure 31E:
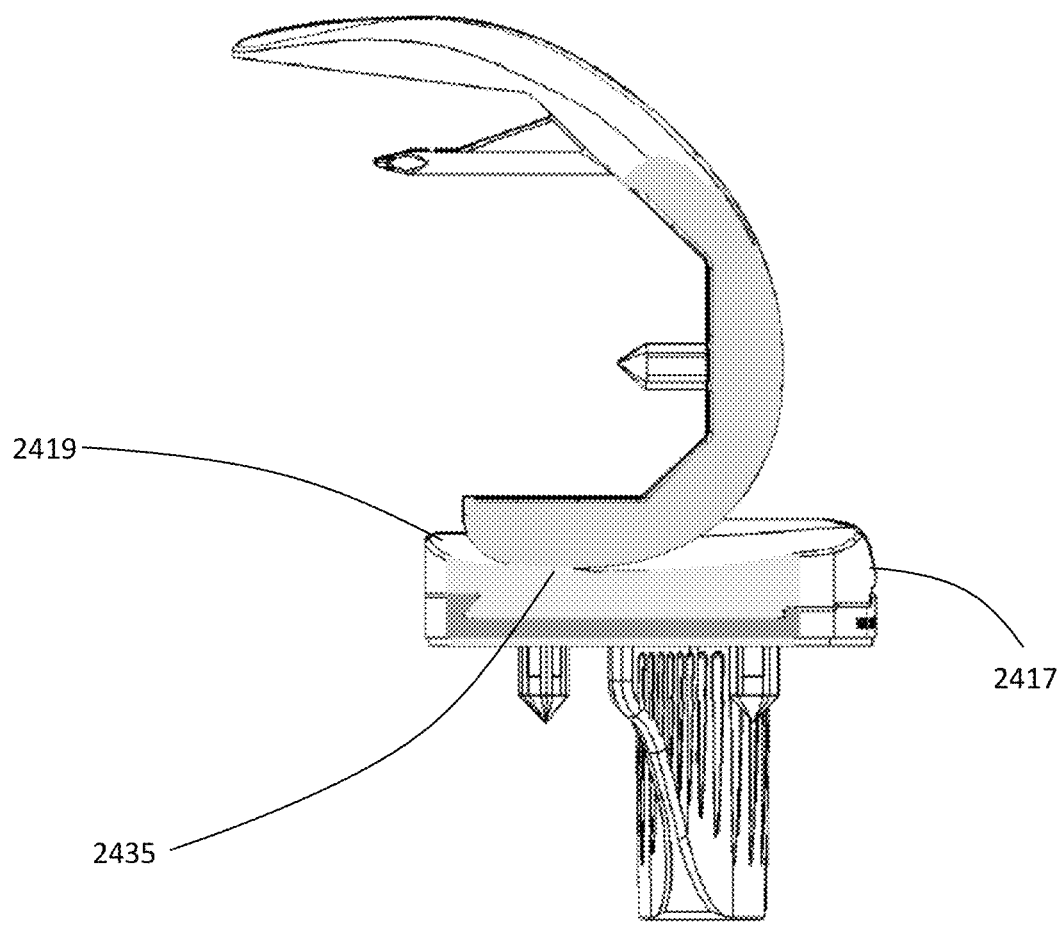
FIG. 31E is a medial view of the knee prosthesis assembly of FIG. 31A an anterior-posterior cross-section through the medial articulation surface.

FIGS. 31A-31E show a posterior view of the composed assembly 2400 in 90 degree flexion, in a left knee. FIG. 31A is a medial-lateral cross-section perspective view of the assembly 2400. The medial condylar articulation surface 2404 meets the medial articulation surface 2420 at a medial dwell point 2435. The lateral condylar articulation surface 2405 meets the lateral articulation surface 2421 at a lateral dwell point 2436. FIGS. 31B and 31C show the medial dwell point 2435 and the lateral dwell point 2436 at what may be considered a starting position, in 90 degrees flexion. FIG. 31D is an anterior-posterior cross-section through the lateral articulation side 2414 of the insert 2410. The medial ramp 2419 is visible (in the background) and shows the height difference between the medial posterior side 2415 and the lateral posterior side 2416. FIG. 31E is an anterior-posterior cross-section through the medial articulation side 2413 of the insert 2410; the medial ramp 2419 is visible and is occluding the lower lateral posterior side 2416. Relative to 0 degrees flexion, the medial dwell point 2435 has moved substantially anteriorly and outwardly toward the medial perimeter 2426 and the lateral dwell point 2436 has not moved significantly. During the transition from extension to flexion, the medial dwell point 2435 has moved anteriorly from the medial ramp 2419 toward the medial low point 2428. The lateral dwell point 2436 has not substantially moved along the lateral articulation surface 2421.

The asymmetry of the insert 2410, and particularly the medial ramp 2419, may cause greater translation of the medial dwell point 2435 compared to the lateral dwell point 2436. The medial dwell point 2436 translation, alone or in conjunction with lateral dwell point 2435 translation, causes or allows tibiofemoral rotation similar to that of a natural knee. Tibiofemoral rotation in a natural knee is the outward rotation of the tibia and lower leg relative to the femur in flexion. In natural tibiofemoral rotation, the toes point outward in flexion compared to extension. The degree of medial dwell point 2435 translation may correspond to rotation of the tibial component 2440 and insert 2410 relative to the femoral component 2401.

The resultant tibiofemoral rotation as a result of the asymmetry of the insert 2410 may provide additional joint stability in the patient. As the medial dwell point 1540 migrates medially, toward the sagittal plane, the medial collateral ligaments of the knee may maintain tension as the knee moves from extension to flexion. The tibiofemoral rotation and maintenance of tension of the medial ligaments may more accurately mimic the movement of a healthy knee. Assembly 2400 may allow a more natural biomechanical range of motion of the knee compared to knee prosthetics with symmetric medial and lateral articulation sides.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The Figures may show simplified or partial views, and the dimensions of elements in the Figures may be exaggerated or otherwise not in proportion for clarity. In addition, the singular forms "a," "an," and "the" include plural referents unless the context clearly dictates otherwise. Thus, for example, reference to a terminal includes reference to one or more terminals. In addition, where reference is made to a list of elements (e.g., elements a, b, c), such reference is intended to include any one of the listed elements by itself, any combination of less than all of the listed elements, and/or a combination of all of the listed elements.

The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As used herein, the term "proximal", "top", "up" or "upwardly" may refer to a location on the device that is closest to the clinician using the device and farthest from the patient in connection with whom the device is used when the device is used in its normal operation. Conversely, the term "distal", "bottom", "down" or "downwardly" may refer to a location on the device that is farthest from the clinician using the device and closest to the patient in connection with whom the device is used when the device is used in its normal operation. Moreover, the terms "upper" and "lower", and "top" and "bottom", "front" and "rear" may be used as relative terms herein for ease of description and understanding. It is understood that in embodiments of the disclosure, upper and lower entities may be reversed, as may top and bottom, front and rear.

As used herein, the term "in" or "inwardly" refers to a location with respect to the device that, during normal use, is toward the inside of the device. Conversely, as used herein, the term "out" or "outwardly" refers to a location with respect to the device that, during normal use, is toward the outside of the device.

As used herein, the term "sagittal" refers to a midline of a patient's anatomy, which divides the body into left or right halves. The sagittal plane may be in the center of the body, splitting it into two halves.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the methods and systems of the present disclosure set forth herein without departing from it spirit and scope.

The invention claimed is:

1. A knee joint prosthesis for implantation in a knee of a patient, the knee joint defining a junction of a femur of the patient and a tibia of the patient; the knee joint prosthesis comprising:
　a tibial baseplate configured to be implanted on the tibia, the tibial baseplate comprising an insert interface;
　a femoral component configured to be implanted on the femur, wherein the femoral component comprises a medial condyle with a medial articulation surface and a lateral condyle with a lateral articulation surface, wherein the medial articulation surface and the lateral articulation surface are shaped substantially symmetrically to each other across a femoral component plane bisecting the femoral component; and
　a tibial insert comprising a baseplate interface attachable to the insert interface of the tibial baseplate;
　wherein the tibial insert comprises an articulation surface with a medial articulation side configured to articulate with the medial articulation surface and a lateral articulation side configured to articulate with the lateral articulation surface, wherein the medial articulation side and the lateral articulation side are shaped substantially asymmetrically to each other across a tibial insert plane bisecting the tibial insert,
　wherein:
　the medial articulation side comprises a medial side height differential defined by:
　　a posterior side with a first height, and
　　an anterior side with a second height;
　the lateral articulation side comprises a lateral side height differential defined by:
　　a posterior side with a third height, and
　　an anterior side with a fourth height; and wherein
　the medial side height differential is greater than the lateral side height differential;
　wherein the medial articulation side comprises an anterior section with a maximum anterior height and a posterior section with a maximum posterior height;
　the posterior section further comprising a posterior ramp; the posterior ramp having a first height proximate a medial posterior section of the medial articulation side and a second height anterior and/or distal to the medial posterior section, wherein the first height is greater than the second height;
　wherein the lateral articulation side comprises an anterior section with a maximum anterior height and a posterior section with a maximum posterior height; wherein the maximum posterior height of the medial articulation side is greater than the maximum posterior height of the lateral articulation side;
　wherein the femoral component and the tibial insert are shaped such that, after implantation in the knee, the femoral component and the tibial insert engage at a medial dwell point and a lateral dwell point, wherein the medial dwell point migrates medially and/or the lateral dwell point migrates laterally during flexion of the knee, creating a tibiofemoral rotation between extension and flexion while the knee joint is stabilized by maintenance of tension in at least a medial collateral ligament of the knee.

2. The knee joint prosthesis of claim 1, wherein the femoral component and the tibial insert are further shaped such that, during flexion, the tibial insert pivots medially relative to the femoral component.

3. The knee joint prosthesis of claim 1, wherein the maintenance of tension further comprises maintenance of tension in a lateral collateral ligament of the knee during flexion.

* * * * *